US011718656B2

(12) United States Patent
Ostertag et al.

(10) Patent No.: US 11,718,656 B2
(45) Date of Patent: Aug. 8, 2023

(54) INDUCIBLE CASPASES AND METHODS FOR USE

(71) Applicant: Poseida Therapeutics, Inc., San Diego, CA (US)

(72) Inventors: Eric M. Ostertag, Lexington, KY (US); Devon Shedlock, San Diego, CA (US)

(73) Assignee: Poseida Therapeutics, Inc., San Diego, CA (US)

( * ) Notice: Subject to any disclaimer, the term of this patent is extended or adjusted under 35 U.S.C. 154(b) by 0 days.

(21) Appl. No.: 17/830,773

(22) Filed: Jun. 2, 2022

(65) Prior Publication Data

US 2023/0002469 A1 Jan. 5, 2023

Related U.S. Application Data

(62) Division of application No. 16/339,710, filed as application No. PCT/US2017/055661 on Oct. 6, 2017, now Pat. No. 11,377,480.

(60) Provisional application No. 62/405,184, filed on Oct. 6, 2016.

(51) Int. Cl.
| | |
|---|---|
| *C12N 15/52* | (2006.01) |
| *C07K 14/705* | (2006.01) |
| *C07K 14/47* | (2006.01) |
| *A61P 37/00* | (2006.01) |
| *A61P 31/00* | (2006.01) |
| *A61P 3/00* | (2006.01) |
| *A61P 17/02* | (2006.01) |
| *A61P 29/00* | (2006.01) |
| *A61P 35/00* | (2006.01) |
| *A61K 35/17* | (2015.01) |
| *C12N 5/0783* | (2010.01) |
| *C12N 9/50* | (2006.01) |

(52) U.S. Cl.
CPC ............ *C07K 14/705* (2013.01); *A61K 35/17* (2013.01); *A61P 3/00* (2018.01); *A61P 17/02* (2018.01); *A61P 29/00* (2018.01); *A61P 31/00* (2018.01); *A61P 35/00* (2018.01); *A61P 37/00* (2018.01); *C07K 14/47* (2013.01); *C07K 14/4747* (2013.01); *C12N 5/0636* (2013.01); *C12N 9/50* (2013.01); *C12N 15/52* (2013.01); *C12Y 304/22036* (2013.01)

(58) Field of Classification Search
None
See application file for complete search history.

(56) References Cited

U.S. PATENT DOCUMENTS

| | | | |
|---|---|---|---|
| 4,656,134 A | 4/1987 | Ringold | |
| 4,683,195 A | 7/1987 | Mullis et al. | |
| 4,683,202 A | 7/1987 | Mullis | |
| 4,766,067 A | 8/1988 | Biswas | |
| 4,795,699 A | 1/1989 | Tabor et al. | |
| 4,800,159 A | 1/1989 | Mullis et al. | |
| 4,889,818 A | 12/1989 | Gelfand et al. | |
| 4,921,794 A | 5/1990 | Tabor et al. | |
| 4,965,188 A | 10/1990 | Mullis et al. | |
| 4,994,370 A | 2/1991 | Silver et al. | |
| 5,066,584 A | 11/1991 | Gyllensten et al. | |
| 5,091,310 A | 2/1992 | Innis | |
| 5,122,464 A | 6/1992 | Wilson et al. | |
| 5,130,238 A | 7/1992 | Malek et al. | |
| 5,142,033 A | 8/1992 | Innis | |
| 5,168,062 A | 12/1992 | Stinski | |
| 5,266,491 A | 11/1993 | Nagata et al. | |
| 5,385,839 A | 1/1995 | Stinski | |
| 5,580,734 A | 12/1996 | Treco et al. | |
| 5,641,670 A | 6/1997 | Treco et al. | |
| 5,733,761 A | 3/1998 | Treco et al. | |
| 5,770,359 A | 6/1998 | Wilson et al. | |
| 5,827,739 A | 10/1998 | Wilson et al. | |
| 6,835,394 B1 | 12/2004 | Discher et al. | |
| 7,217,427 B2 | 5/2007 | Discher et al. | |
| 7,867,512 B2 | 1/2011 | Discher et al. | |
| 9,393,292 B2 | 7/2016 | Brenner | |
| 9,913,882 B2 | 3/2018 | Slawin et al. | |
| 11,377,480 B2 | 7/2022 | Ostertag et al. | |

FOREIGN PATENT DOCUMENTS

| | | |
|---|---|---|
| WO | WO 03/020759 A2 | 3/2003 |
| WO | WO 2006/133398 A2 | 12/2006 |
| WO | WO 2011/133635 A2 | 10/2011 |
| WO | WO 2011/146862 A1 | 11/2011 |
| WO | WO 2012/094679 A2 | 7/2012 |
| WO | WO 2015/134877 A1 | 9/2015 |
| WO | WO 2016/022805 A1 | 2/2016 |
| WO | WO 2016/090111 A1 | 6/2016 |
| WO | WO 2016/135470 A1 | 9/2016 |
| WO | WO 2017/004498 A1 | 1/2017 |

(Continued)

OTHER PUBLICATIONS

US 5,733,746 A, 03/1998, Treco et al. (withdrawn)
GenBank Accession No. AH002818 "*Homo sapiens* FKBP12C (FKBP12) gene, FK506-binding protein 12 (FKBP12) gene, complete cds; and FKBP12A (FKBP12) gene, complete sequence" Jun. 10, 2016, 4 pages.
Arcone, R. et al. (1988) "Identification of sequences responsible for acute-phase induction of human C-reactive protein" *Nucl Acids Res*, 16:3195-3207.
Bojak, A. et al. (2002) "Muscle specific versus ubiquitous expression of Gag based HIV-1 DNA vaccines: a comparative analysis" *Vaccine*, 20:1975-1979.

(Continued)

*Primary Examiner* — Anand U Desai
(74) *Attorney, Agent, or Firm* — Cooley LLP; Matthew Pavao; Ivor Elrifi

(57) ABSTRACT

The disclosure provides inducible caspase polypeptides, compositions comprising inducible caspase polypeptides and sequences encoding the same, cells modified to express the polypeptides and compositions of the disclosure, as well as methods of making and methods of using same for adoptive cell therapy.

10 Claims, 12 Drawing Sheets

Specification includes a Sequence Listing.

(56) References Cited

FOREIGN PATENT DOCUMENTS

| WO | WO 2017/004509 A1 | 1/2017 |
|---|---|---|
| WO | WO 2017/190091 A1 | 11/2017 |

OTHER PUBLICATIONS

Cao, Y. et al. (2009) "Construction and Characterization of Novel, Recombinant Immunotoxins Targeting the Her2/neu Oncogene Product: In vitro and In vivo Studies" Cancer Res, 69(23):8987-8995.

Cazeaux, N. et al. (2002) "Comparative study of immune responses induced after immunization with plasmids encoding the HIV-1 Nef protein under the control of the CMV-IE or the muscle-specific desmin promoter" Vaccine, 20:3322-3331.

Clarkson, T. et al. (Sep. 1998) "Redesigning an FKBP-ligand interface to generate chemical dimerizers with novel specificity" Proc Natl Acad Sci, 95(18):10437-10442.

Cunningham, B.C. and J.A. Wells (Jun. 2, 1989) "High-Resolution Epitope Mapping of hGH-Receptor Interactions by Alanine-Scanning Mutagenesis" Science, 244:1081-1085.

De Vos, A.M. et al. (1992) "Human Growth Hormone and Extracellular Domain of Its Receptor: Crystal Structure of the Complex" Science, 255:306-312.

Di Stasi (Nov. 2011) "Inducible Apoptosis as a Safety Switch for Adoptive Cell Therapy" N Engl J Med, 365(18):1673-1683. NIH Public Access Author Manuscript; available in PMC May 3, 2012, 16 pages.

Donnelly, J.J. et al. (1997) "DNA Vaccines" Annu Rev Immunol, 15:617-648.

Gossen, M. and Bujard, H. (Jun. 1992) "Tight control of gene expression in mammalian cells by tetracycline-responsive promoters" Proc Natl Acad Sci USA, 89:5547-5551.

Gossen, M. et al. (1995) "Transcriptional activation by tetracyclkines in mammalian cells" Science, 268(5218):1766-1769.

Iuliucci, J.D. et al. (2001) "Intravenous Safety and Pharmacokinetics of a Novel Dimerizer Drug, AP1903, in Healthy Volunteers" J Clin Pharmacol, 41:870-879.

Jin, Z. et al. (2011) "The hyperactive Sleeping Beauty transposase SB100X improves the genetic modification of T cells to express a chimeric antigen receptor" Gene Therapy, 18:849-856.

Kageyama, R. et al. (Feb. 15, 1987) "Differing Utilization of Homologous Transcription Initiation Sites of Rat K and T Kininogen Genes Under Inflammation Condition" J Biol Chem, 262(5):2345-2351.

Kemper, K. et al. (2012) "Targeting colorectal cancer stem cells with inducible caspase-9" Apoptosis, 17:528-537.

Maus, M.V. et al. (2014) "Antibody-modified T cells: CARs take the front seat for hematologic malignancies" Blood, 123(17):2625-2635.

Nakazawa, Y. et al. (Jan. 2013) "Evaluation of long-term transgene expression in piggyBac-modified human T lymphocytes" J Immunother, 36(1):3-10. NIH Public Access Author Manuscript; available in PMC Jan. 1, 2014, 16 pages.

Oliviero, S. et al. (1987) "The human haptoglobin gene: transcriptional regulation during development and acute phase induction" The EMBO Journal, 6(7):1905-1912.

Poli, V. et al. (Nov. 1989) "Interleukin 6 induces a liver-specific nuclear protein that binds to the promoter of acute-phase genes" Proc Natl Acad Sci USA, 86:8202-8206.

Philip, B. et al. (2014) "A highly compact epitope-based marker/suicide gene for easier and safer T-cell therapy" Blood, 124(8):1277-1287.

Prowse, K.R. and H. Baumann (Jan. 1988) "Hepatocyte-Stimulating Factor, $\beta_2$ Interferon, and Interleukin-1 Enhance Expression of the Rat $\alpha_1$-Acid Glycoprotein Gene via a Distal Upstream Regulatory Region" Mol Cell Biol, 8(I):42-51.

Quntarelli, C. et al. (Oct. 15, 2007) "Co-expression of cytokine and suicide genes to enhance the activity and safety of tumor-specific cytotoxic T lymphocytes" Blood, 110(8):2793-2802 [online]. Retrieved from the Internet: www.ncbi.nlm.nih.gov/pmc/articles/PMC2018664/?report=printable; retrieved on Apr. 1, 2019, 22 printed pages.

Ramos, C.A. et al. (2010) "An Inducible Caspase 9 Suicide Gene to Improve the Safety of Mesenchymal Stromal Cell Therapies" Stem Cells, 28:1107-1115.

Ron, D. et al. (May 1991) "Angiotensinogen Gene-Inducible Enhancer-Binding Protein 1, a Member of a New Family of Large Nuclear Proteins That Recognize Nuclear Factor kappaB-Binding Sites through a Zinc Finger Motif" Mol Cell Biol, 11(5):2887-2895.

Shan, D. et al. (1999) "Characterization of scFv-Ig Constructs Generated from the Anti-CD20 mAb 1F5 Using Linker Peptides of Varying Lengths" J Immunol, 162:6859-6595.

Smith, L.J. et al. (1992) "Human Interleukin 4. The Solution Structure of a Four-helix Bundle Protein" J Mol Biol, 244:899-904.

Sprague, J. et al. (Feb. 1983) "Expression of a Recombinant DNA Gene Coding for the Vesicular Stomatitis Virus Nucleocapsid Protein" J Virol, 45(2):773-781.

Straathof, K.C. et al. (2005) "An inducible caspase 9 safety switch for T-cell therapy" Blood, 105:4247-4254.

Tey, S-K. et al. (2007) "Inducible Caspase 9 Suicide Gene to Improve the Safety of Allodepleted T Cells after Haploidentical Stem Cell Transplantation" Biol Blood Marrow Transpl, 13:913-924.

Wilson, D.R. et al. (Dec. 1990) "A 58-Base-Pair Region of the Human C3 Gene Confers Synergistic Inducibility by Interleukin-1 and Interleukin-6" Mol Cell Biol, 10(12):6181-6191.

Xie, X. et al. (Sep. 2001) "Adenovirus-mediated Tissue-targeted Expression of a Caspase-9-based Artificial Death Switch for the Treatment of Prostate Cancer" Cancer Research, 61:6795-6804.

Zechner, R. et al. (Jun. 1988) "Recombinant Human Cachectin/Tumor Necrosis Factor but Not Interleukin-1$\alpha$ Downregulates Lipoprotein Lipase Gene Expression at the Transcriptional Level in Mouse 3T3-L1 Adipocytes" Mol Cell Biol, 8(6):2394-2401.

Zhao, H.L. et al. (Sep. 2008) "Increasing the homogeneity, stability and activity of human serum albumin and interferon-alpha2b fusion protein by linker engineering" Protein Expr Purif, 61(1):73-77.

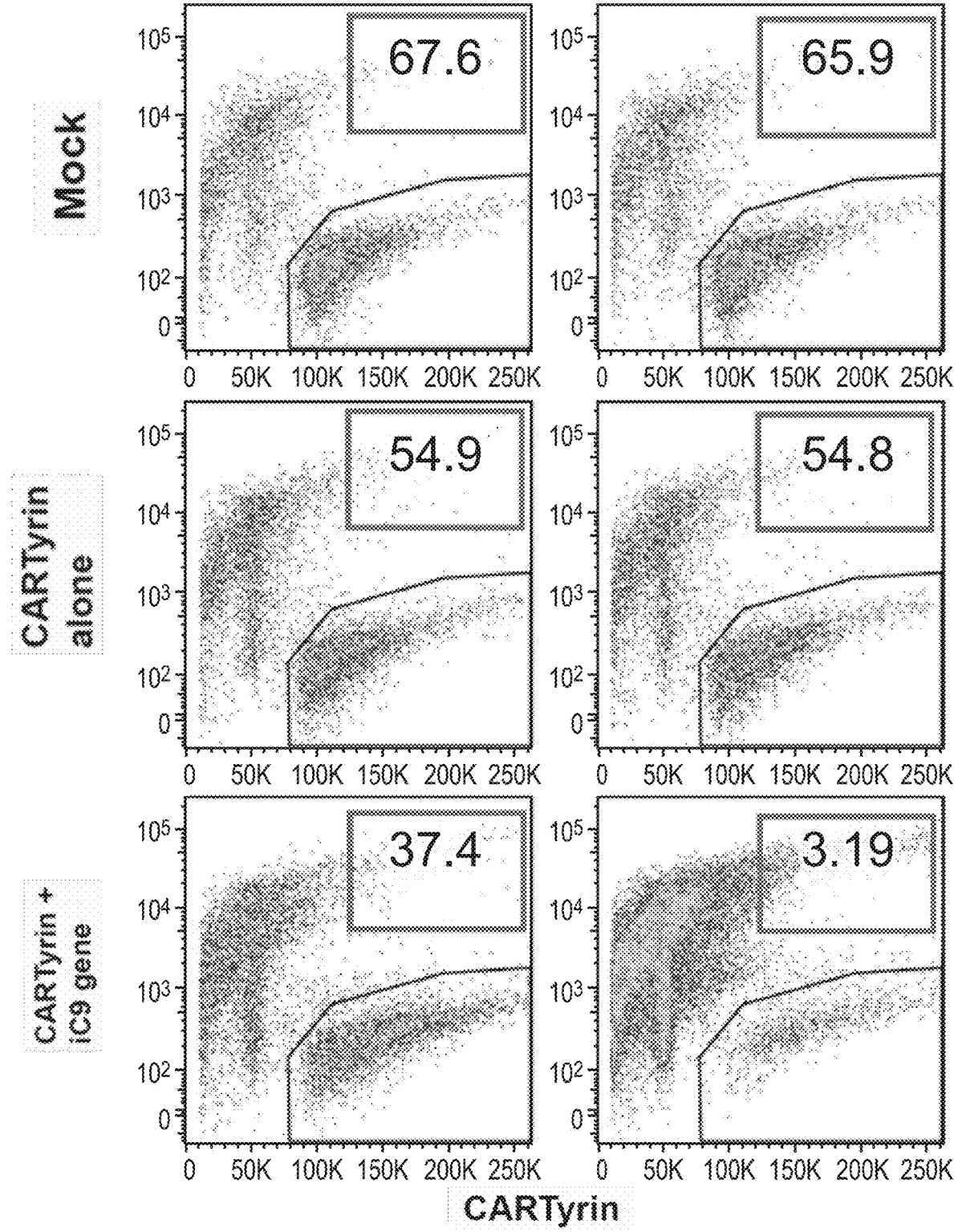

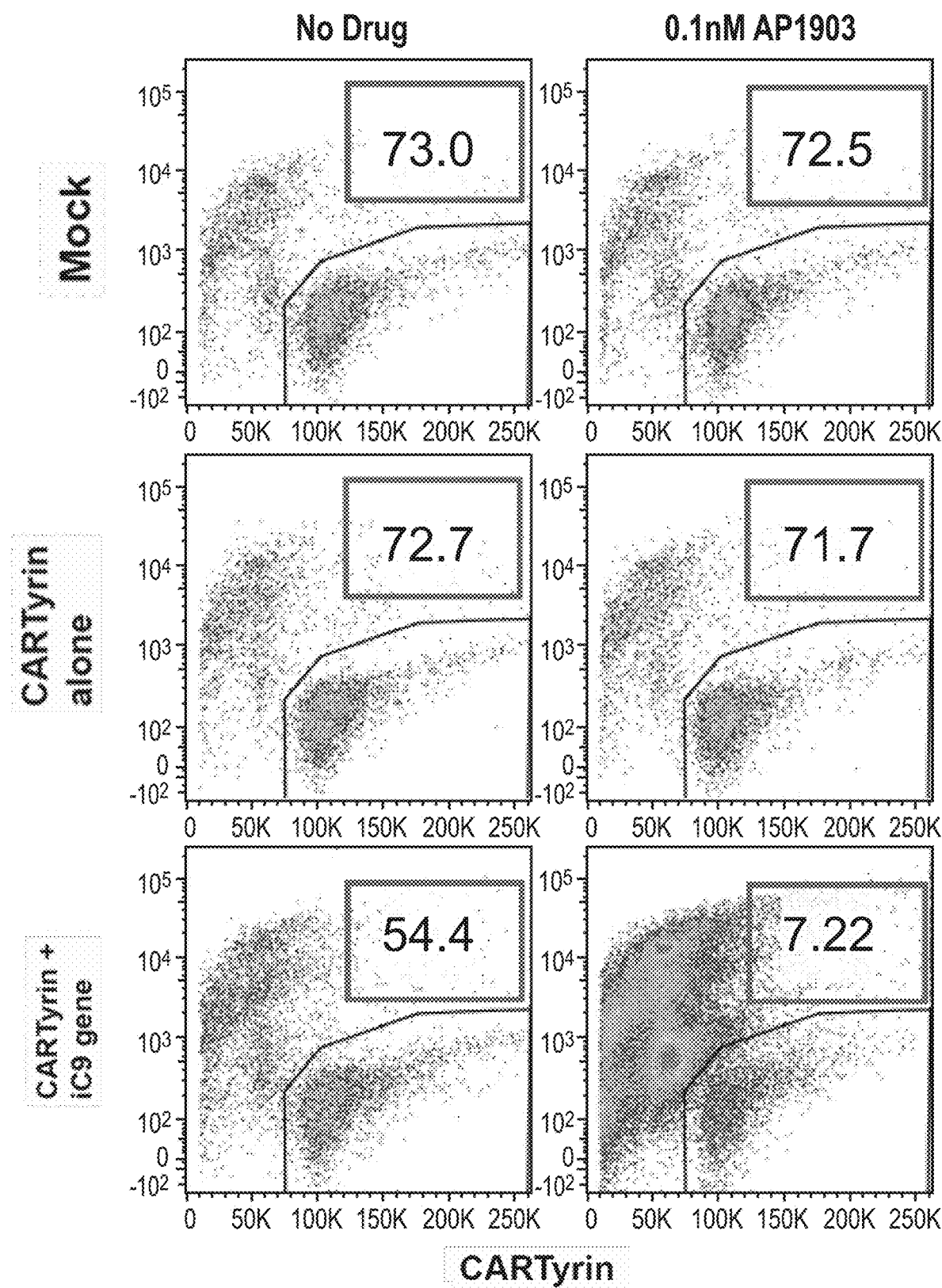

INDUCIBLE CASPASES AND METHODS FOR USE

RELATED APPLICATIONS

This application is a divisional application of U.S. patent application Ser. No. 16/339,710, filed on Apr. 4, 2019, which is a U.S. national stage application of International Patent Application No.: PCT/US2017/055661, filed on Oct. 6, 2017, which claims the benefit of priority to U.S. Provisional Patent Application No. 62/405,184, filed on Oct. 6, 2016. The contents of each of these applications are herein incorporated by reference in their entirety.

INCORPORATION OF SEQUENCE LISTING

The contents of the text filed named "POTH-011_D01US_SeqList.txt", which was created on Apr. 25, 2022 and is 62,079 bytes in size, are hereby incorporated by reference in their entirety.

FIELD OF THE DISCLOSURE

The disclosure is directed to molecular biology, and more, specifically, to compositions containing at least one sequences encoding an inducible caspase protein, as well as methods of making and using the same.

BACKGROUND

There has been a long-felt but unmet need in the art for a method of selectively inducing apoptosis in genetically modified cells, and, in particular, those modified cells intended for administration to a subject as, for example an adoptive cell therapy. The disclosure provides a solution to this long-felt but unmet need.

SUMMARY

The disclosure provides an inducible proapoptotic polypeptide operably linked to a ligand binding region that may be optimized to bind a chemical inducer of dimerization. When the ligand binding region specifically binds the induction agent, pro-apoptotic target molecules are cross-linked, and, consequently, activated to selectively induce apoptosis in a cell containing an inducible proapoptotic polypeptide of the disclosure. Preferred inducible proapoptotic polypeptides of the disclosure include, but are not limited to, inducible caspase polypeptides. Preferred inducible caspase polypeptides of the disclosure include, but are not limited to, inducible caspase 9 polypeptides. Preferred inducible caspase 9 polypeptides of the disclosure may comprise a truncated caspase 9 polypeptide encoded by a truncated or modified amino acid and/or nucleic acid sequence encoding the truncated caspase 9 polypeptide.

Inducible proapoptotic polypeptides of the disclosure are superior to existing inducible polypeptides because the inducible proapoptotic polypeptides of the disclosure are far less immunogenic. While inducible proapoptotic polypeptides of the disclosure are recombinant polypeptides, and, therefore, non-naturally occurring, the sequences that are recombined to produce the inducible proapoptotic polypeptides of the disclosure do not comprise non-human sequences that the host human immune system could recognize as "non-self" and, consequently, induce an immune response in the subject receiving an inducible proapoptotic polypeptide of the disclosure, a cell comprising the inducible proapoptotic polypeptide or a composition comprising the inducible proapoptotic polypeptide or the cell comprising the inducible proapoptotic polypeptide. Although the linker sequence is an artificial sequence, the linker sequence does not comprise a non-human sequence. For example, the linker sequence does not comprise a restriction site.

The disclosure provides an inducible proapoptotic polypeptide comprising (a) a ligand binding region, (b) a linker, and (c) a proapoptotic polypeptide, wherein the inducible proapoptotic polypeptide does not comprise a non-human sequence. In certain embodiments, the non-human sequence comprises a restriction site. In certain embodiments, the ligand binding region may be a multimeric ligand binding region.

The disclosure provides an inducible caspase polypeptide comprising (a) a ligand binding region, (b) a linker, and (c) a caspase polypeptide, wherein the inducible proapoptotic polypeptide does not comprise a non-human sequence. In certain embodiments, the non-human sequence comprises a restriction site. In certain embodiments, the ligand binding region may be a multimeric ligand binding region.

The disclosure provides an inducible caspase polypeptide comprising (a) a ligand binding region, (b) a linker, and (c) a truncated caspase 9 polypeptide, wherein the inducible proapoptotic polypeptide does not comprise a non-human sequence. In certain embodiments, the non-human sequence comprises a restriction site. In certain embodiments, the ligand binding region may be a multimeric ligand binding region.

In certain embodiments of the inducible caspase polypeptide, the ligand binding region may specifically bind an induction agent and activate transcription of the proapoptotic polypeptide (e.g. caspase polypeptide) of the disclosure. For example, the ligand binding region will not bind a therapeutic agent. Induction agents specifically bound by the ligand binding region of the inducible polypeptides of the disclosure do not directly induce transcription of endogenous genes.

Inducible proapoptotic (e.g. caspase) polypeptides of the disclosure may be under the control of one or more transcriptional regulatory elements, including, but not limited to, a promoter capable of initiating transcription of the caspase polypeptide in a cell modified to contain an inducible caspase polypeptide of the disclosure. For example, inducible caspase polypeptides of the disclosure may be under the control of one or more transcriptional regulatory elements, including, but not limited to, a mammalian promoter capable of initiating transcription of the caspase polypeptide in a mammalian cell modified to contain an inducible caspase polypeptide of the disclosure. For example, inducible caspase polypeptides of the disclosure may be under the control of one or more transcriptional regulatory elements, including, but not limited to, a heterologous or exogenous promoter capable of initiating transcription of the caspase polypeptide in a mammalian cell modified to contain an inducible caspase polypeptide of the disclosure. Preferred mammalian cells include, but are not limited to human cells.

The disclosure provides an inducible caspase polypeptide comprising (a) a ligand binding region, (b) a linker, and (c) a truncated caspase 9 polypeptide, wherein the inducible proapoptotic polypeptide does not comprise a non-human sequence. In certain embodiments, the ligand binding region may be a multimeric ligand binding region.

In certain embodiments of the inducible proapoptotic polypeptides, inducible caspase polypeptides or truncated caspase 9 polypeptides of the disclosure, the ligand binding region may comprise a FK506 binding protein 12 (FKBP12) polypeptide. In certain embodiments, the amino acid sequence of the ligand binding region that comprise a FK506 binding protein 12 (FKBP12) polypeptide may comprise a modification at position 36 of the sequence. The modification may be a substitution of valine (V) for phenylalanine (F) at position 36 (F36V). In certain embodiments, the FKBP12 polypeptide is encoded by an amino acid sequence comprising GVQVETISPGDGRTFPKRGQTCVVHYTGMLED GKKVDSSRDRNKPFKFMLGKQEVIRG WEEGVAQMSVGQRAKLTISPDYAYGATGHPGIIP-PHATLVFDVELLKLE (SEQ ID NO: 3). In certain embodiments, the FKBP12 polypeptide is encoded by a nucleic acid sequence comprising GGGGTCCAGGTCGAGACTATTT-CACCAGGGGATGGGCGAACATTTCCAAAAAGGGG CCAGACTTGCGTCGTGCATTACACCGGGATGCTG-GAGGACGGGAAGAAAGTGGACA GCTCCAGG-GATCGCAACAAGCCCTTCAAGTTCATGCTGG-GAAAGCAGGAAGTGATC CGAGGATGGGAGGAAGGCGTGGCACA-GATGTCAGTCGGCCAGCGGGCCAAACTGA CCATT-AGCCCTGACTACGCTTATGGAGCAACAGGC-CACCCAGGGATCATTCCCCCTC ATGCCACCCTGGTCTTCGAT GTGGAACTGCT-GAAGCTGGAG (SEQ ID NO: 4). In certain embodiments, the induction agent specific for the ligand binding region may comprise a FK506 binding protein 12 (FKBP12) polypeptide having a substitution of valine (V) for phenylalanine (F) at position 36 (F36V) comprises AP20187 and/or AP1903 (Rimiducid), both synthetic drugs.

In certain embodiments of the inducible proapoptotic polypeptides, inducible caspase polypeptides or truncated caspase 9 polypeptides of the disclosure, the linker region is encoded by an amino acid comprising GGGGS (SEQ ID NO: 5) or a nucleic acid sequence comprising GGAGGAG-GAGGATCC (SEQ ID NO: 6). In certain embodiments, the nucleic acid sequence encoding the linker does not comprise a restriction site.

In certain embodiments of the truncated caspase 9 polypeptides of the disclosure, the truncated caspase 9 polypeptide is encoded by an amino acid sequence that does not comprise an arginine (R) at position 87 of the sequence. Alternatively, or in addition, in certain embodiments of the inducible proapoptotic polypeptides, inducible caspase polypeptides or truncated caspase 9 polypeptides of the disclosure, the truncated caspase 9 polypeptide is encoded by an amino acid sequence that does not comprise an alanine (A) at position 282 the sequence. In certain embodiments of the inducible proapoptotic polypeptides, inducible caspase polypeptides or truncated caspase 9 polypeptides of the disclosure, the truncated caspase 9 polypeptide is encoded by an amino acid comprising GFGDVGALESLRGNAD-LAYILSMEPCGHCLIINNVNFCRESGLRTRTG-SNIDCEKLRRRF SSLHFMVEVKGDLTAKKMVLAL-LELAQQDHGALDCCVVVILSHGCQASHLQFPGAVY GTDGCPVS-
VEKIVNIFNGTSCPSLGGKPKLFFIQACGGEQKDHGFE-VASTSPEDESPGSNP EPDATPFQEGLRTFDQL-DAISSLPTPSDIFVSYSTFPGFVSWRDPKSGS WYVETLDDIFEQ WAHSEDLQSLLLRVA-NAVSVKGIYKQMPGCFNFLRKKLFFKTS (SEQ ID NO: 7) or a nucleic acid sequence comprising

```
                                        (SEQ ID NO: 8)
TTTGGGGACGTGGGGGCCCTGGAGTCTCTGCGAGGAAATGCCGATCTGG

CTTACATCCTGAGCATGGAACCCTGCGGCCACTGTCTGATCATTAACAA

TGTGAACTTCTGCAGAGAAAGCGGACTGCGAACACGGACTGGCTCCAAT

ATTGACTGTGAGAAGCTGCGGAGAAGGTTCTCTAGTCTGCACTTTATGG

TCGAAGTGAAAGGGGATCTGACCGCCAAGAAAATGGTGCTGGCCCTGCT

GGAGCTGGCTCAGCAGGACCATGGAGCTCTGGATTGCTGCGTGGTCGTG

ATCCTGTCCCACGGGTGCCAGGCTTCTCATCTGCAGTTCCCCGGAGCAG

TGTACGGAACAGACGGCTGTCCTGTCAGCGTGGAGAAGATCGTCAACAT

CTTCAACGGCACTTCTTGCCCTAGTCTGGGGGGAAAGCCAAACTGTTC

TTTATCCAGGCCTGTGGCGGGAACAGAAAGATCACGGCTTCGAGGTGG

CCAGCACCAGCCCTGAGGACGAATCACCAGGGAGCAACCCTGAACCAGA

TGCAACTCCATTCCAGGAGGGACTGAGGACCTTTGACCAGCTGGATGCT

ATCTCAAGCCTGCCCACTCCTAGTGACATTTTCGTGTCTTACAGTACCT

TCCCAGGCTTTGTCTCATGGCGCGATCCCAAGTCAGGGAGCTGGTACGT

GGAGACACTGGACGACATCTTTGAACAGTGGGCCCATTCAGAGGACCTG

CAGAGCCTGCTGCTGCGAGTGGCAAACGCTGTCTCTGTGAAGGGCATCT

ACAAACAGATGCCCGGGTGCTTCAATTTTCTGAGAAAGAAACTGTTCTT

TAAGACTTCC.
```

In certain embodiments of the inducible proapoptotic polypeptides, wherein the polypeptide comprises a truncated caspase 9 polypeptide, the inducible proapoptotic polypeptide is encoded by an amino acid sequence comprising GVQVETISPGDGRTFPKR GQTCVVHYTGMLEDGKKVDSSRDRNKPFKF MLGKQEVIRGWEEGVAQMSVGQRAKL TISPDYAY-GATGHPGIIPPHATLVFDVELLKLEGGGGSGFGDV-GALESLRGNADLAYILS MEPCGHCLI-INNVNFCRESGLRTRTGSNIDCEKLRRRFSSLHFM VEVKGDLTAKKMVLA LLELAQQDHGALDCCVV-VILSHGCQASHLQFPGAVYGTDGCPVS-VEKIVNIFNGTSCPS LGGKPKLFFIQACGGEQKDHGFEVASTSPEDESPG-SNPEPDATPFQEGLRTFDQLDAISSL PTPSDIFVSYS-TFPGFVSWRDPKSGSWYVETLD-DIFEQWAHSEDLQSLLLRVANAVSVK GIYKQMPGCFNFLRKKLFFKTS (SEQ ID NO: 9) or the nucleic acid sequence comprising GGGGTCCAGGTCGA-GACTATTTCACCAGGGGATGGGCGAACATTTC-CAAAAAGGGG CCAGACTTGCGTCGTGCATTA-CACCGGGATGCTGGAGGACGGGAAGAAAGT GGACA GCTCCAGGGATCGCAACAAGCCCTT-CAAGTTCATGCTGGGAAAGCAGGAAGTGATC CGAGGATGGGAGGAAGGCGTGGCACA-GATGTCAGTCGGCCAGCGGGCCAAACTGA CCATT-AGCCCTGACTACGCTTATGGAGCAACAGGC-CACCCAGGGATCATTCCCCCTC ATGCCACCCTGGTCTTCGATGTGGAACTGCT- GAAGCTGGAGGGAGGAGGAGGATCC GGATTGGGGACGTGGGGGCCCTGGAGTCTCTGCGAGGAAATGCCGATCTGGCTTA
CATCCTGAGCATGGAACCCTGCGGCCACTGTCTGATCATTAACAATGTGAACTTCTG
CAGAGAAAGCGGACTGCGAACACGGACTGGCTCCAATATTGACTGTGAGAAGCTGC
GGAGAAGGTTCTCTAGTCTGCACTTTATGGTCGAAGTGAAAGGGGATCTGACCGCC
AAGAAAATGGTGCTGGCCCTGCTGGAGCTGGCTCAGCAGGACCATGGAGCTCTGGA
TTGCTGCGTGGTCGTGATCCTGTCCCACGGGTGCCAGGCTTCTCATCTGCAGTTCCCC
GGAGCAGTGTACGGAACAGACGGCTGTCCTGTCAGCGTGGAGAAGATCGTCAACAT CTTCAACGGCACTTCTTGCCCTAGTCTGGGGGGAAAGCCAAAACTGTTCTTTATCCA
GGCCTGTGGCGGGGAACAGAAAGATCACGGCTTCGAGGTGGCCAGCACCAGCCCTG
AGGACGAATCACCAGGGAGCAACCCTGAACCAGATGCAACTCCATTCCAGGAGGGA
CTGAGGACCTTTGACCAGCTGGATGCTATCTCAAGCCTGCCCACTCCTAGTGACATT TTCGTGTCTTACAGTACCTTCCCAGGCTTTGTCTCATGGCGCGATCCCAAGTCAGGG
AGCTGGTACGTGGAGACACTGGACGACATCTTTGAACAGTGGGCCCATTCAGAGGA
CCTGCAGAGCCTGCTGCTGCGAGTGGC
AAACGCTGTCTCTGTGAAGGGCATCTACAA ACAGATGCCCGGGTGCTTCAATTTTCTGAGAAAGAAACTGTTCTTTAAGACTTCC (SEQ ID NO: 10).

The disclosure provides a composition comprising an inducible proapoptotic polypeptide, inducible caspase polypeptide, inducible caspase 9 polypeptide, and/or inducible truncated caspase 9 polypeptide of the disclosure.

The disclosure provides a transposon comprising an inducible proapoptotic polypeptide, inducible caspase polypeptide, inducible caspase 9 polypeptide, and/or inducible truncated caspase 9 polypeptide of the disclosure.

The disclosure provides a transposon comprising an inducible proapoptotic polypeptide, inducible caspase polypeptide, inducible caspase 9 polypeptide, and/or inducible truncated caspase 9 polypeptide of the disclosure. In certain embodiments of the transposons of the disclosure, the transposon further comprises a sequence encoding a therapeutic protein. In certain embodiments, the therapeutic protein is naturally-occurring. In certain embodiments, the therapeutic protein is an endogenous protein. In certain embodiments, the therapeutic protein is an exogenous protein.

The disclosure provides a transposon comprising an inducible proapoptotic polypeptide, inducible caspase polypeptide, inducible caspase 9 polypeptide, and/or inducible truncated caspase 9 polypeptide of the disclosure. In certain embodiments of the transposons of the disclosure, the transposon further comprises a sequence encoding a therapeutic protein. In certain embodiments, the therapeutic protein is not naturally-occurring. In certain embodiments, the therapeutic protein is an endogenous protein. In certain embodiments, the therapeutic protein is an exogenous protein. In certain embodiments, the therapeutic protein is a synthetic protein. In certain embodiments, the therapeutic protein is a chimeric or a recombinant protein. In certain embodiments, the therapeutic protein is a fusion protein. In certain embodiments, the therapeutic protein is a human protein, a wild type protein or a sequence variant thereof.

The disclosure provides a transposon comprising an inducible proapoptotic polypeptide, inducible caspase polypeptide, inducible caspase 9 polypeptide, and/or inducible truncated caspase 9 polypeptide of the disclosure. In certain embodiments of the transposons of the disclosure, the transposon further comprises a sequence encoding a therapeutic protein. In certain embodiments, the therapeutic protein comprises a cell surface protein, a membrane-bound protein, an extracellular membrane-bound protein, an intracellular membrane-bound protein, an intracellular protein, a nuclear localized protein, a nuclear protein, a cytoplasmic protein, a cytosolic protein, a secreted protein, a lysosomal protein, an endosomal protein, a vesicle-associated protein, a mitochondrial protein, an endoplasmic reticulum protein, a cytoskeletal protein, a protein involved in intracellular signaling and/or a protein involved in extracellular signaling.

The disclosure provides a transposon comprising an inducible proapoptotic polypeptide, inducible caspase polypeptide, inducible caspase 9 polypeptide, and/or inducible truncated caspase 9 polypeptide of the disclosure. In certain embodiments of the transposons of the disclosure, the transposon further comprises a sequence encoding a therapeutic protein. In certain embodiments, the therapeutic protein comprises an antigen receptor. In certain embodiments, antigen receptor comprises a T-cell receptor. In certain embodiments, antigen receptor comprises a receptor isolated or derived from a T-cell receptor. In certain embodiments, the antigen receptor comprises one or more sequence variation(s) and/or mutation(s) compared to a wild-type T-cell receptor. In certain embodiments, the T-cell receptor is a recombinant T-cell receptor.

The disclosure provides a transposon comprising an inducible proapoptotic polypeptide, inducible caspase polypeptide, inducible caspase 9 polypeptide, and/or inducible truncated caspase 9 polypeptide of the disclosure. In certain embodiments of the transposons of the disclosure, the transposon further comprises a sequence encoding a therapeutic protein. In certain embodiments, wherein the antigen receptor is a Chimeric Antigen Receptor (CAR). In certain embodiments, the CAR comprises one or more Centyrin sequence(s). In certain embodiments, the CAR is a CAR-Tyrin. In certain embodiments, the CAR comprises one or more VHH sequence(s). In certain embodiments, the CAR is a VCAR.

In certain embodiments, a transposon of the disclosure may further comprise at least one self-cleaving peptide. In certain embodiments, a transposon of the disclosure may comprise at least one self-cleaving peptide and wherein a self-cleaving peptide is located between the inducible proapoptotic polypeptide, inducible caspase polypeptide, inducible caspase 9 polypeptide, and/or inducible truncated caspase 9 polypeptide of the disclosure and another sequence in the transposon. In certain embodiments, a transposon of the disclosure may comprise at least one self-cleaving peptide and wherein a self-cleaving peptide is located upstream of the inducible proapoptotic polypeptide, inducible caspase polypeptide, inducible caspase 9 polypeptide, and/or inducible truncated caspase 9 polypeptide of the disclosure and a second self-cleaving peptide is located downstream of the inducible proapoptotic polypeptide, inducible caspase polypeptide, inducible caspase 9 polypeptide, and/or inducible truncated caspase 9 polypeptide of the disclosure. In certain embodiments, a transposon of the disclosure may comprise at least one self-cleaving peptide and wherein a self-cleaving peptide is located immediately upstream of the inducible proapoptotic polypeptide, inducible caspase polypeptide, inducible caspase 9 polypeptide, and/or inducible truncated caspase 9 polypeptide of the disclosure and a second self-cleaving peptide is located immediately downstream of the inducible proapoptotic polypeptide, inducible caspase polypeptide, inducible caspase 9 polypeptide, and/or inducible truncated caspase 9 polypeptide of the disclosure. The at least one self-cleaving peptide may comprise a T2A peptide, GSG-T2A peptide, an E2A peptide, a GSG-E2A peptide, an F2A peptide, a GSG-F2A peptide, a P2A peptide, or a GSG-P2A peptide. In certain embodiments, the T2A peptide comprises an amino acid sequence comprising EGRGSLLTCGDVEENPGP (SEQ ID NO: 11). In certain embodiments, the GSG-T2A peptide comprises an amino acid sequence comprising GSGEGRGSLLTCGDVEENPGP (SEQ ID NO: 12). In certain embodiments, the E2A peptide comprises an amino acid sequence comprising QCTNYALLKLAGDVESNPGP (SEQ ID NO: 13). In certain embodiments, the GSG-E2A peptide comprises an amino acid sequence comprising GSGQCTNYALLKLAGDVESNPGP (SEQ ID NO: 14). In certain embodiments, the F2A peptide comprises an amino acid sequence comprising VKQTLNFDLLKLAGDVESNPGP (SEQ ID NO: 15). In certain embodiments, the GSG-F2A peptide comprises an amino acid sequence comprising GSGVKQTLNFDLLKLAGDVESNPGP (SEQ ID NO: 16). In certain embodiments, the P2A peptide comprises an amino acid sequence comprising ATNFSLLKQAGDVEENPGP (SEQ ID NO: 17). In certain embodiments, the GSG-P2A peptide comprises an amino acid sequence comprising GSGATNFSLLKQAGDVEENPGP (SEQ ID NO: 18).

enzyme may be an mRNA sequence. In certain embodiments, the transposon is a piggyBac transposon. In certain embodiments, the transposon is a piggyBac transposon and the transposase is a Super piggyBac transposase.

Transposons of the disclosure may comprise piggyBac transposons. In certain embodiments of this method, the transposon is a plasmid DNA transposon with a sequence encoding the inducible caspase polypeptide of the disclosure flanked by two cis-regulatory insulator elements. In certain embodiments, the transposon is a piggyBac transposon. Transposase enzymes of the disclosure may include piggyBac transposases or compatible enzymes. In certain embodiments, and, in particular, those embodiments wherein the transposon is a piggyBac transposon, the transposase is a piggyBac™ or a Super piggyBac™ (SPB) transposase. In certain embodiments, and, in particular, those embodiments wherein the transposase is a Super piggyBac™ (SPB) transposase, the sequence encoding the transposase enzyme is an mRNA sequence.

In certain embodiments of the methods of the disclosure, the transposase enzyme is a piggyBac™ (PB) transposase enzyme. The piggyBac (PB) transposase enzyme may comprise or consist of an amino acid sequence at least 75%, 80%, 85%, 90%, 95%, 99% or any percentage in between identical to:

```
                                                         (SEQ ID NO: 1)
  1   MGSSLDDEHI LSALLQSDDE LVGEDSDSEI SDHVSEDDVQ SDTEEAFIDE VHEVQPTSSG

61   SEILDEQNVI EQPGSSLASN RILTLPQRTI RGKNKHCWST SKSTRRSRVS ALNIVRSQRG

121   PTRMCRNIYD PLLCFKLFFT DEIISEIVKW TNAEISLKRR ESMTGATFRD TNEDEIYAFF

181   GILVMTAVRK DNHMSTDDLF DRSLSMVYVS VMSRDRFDFL IRCLRMDDKS IRPTLRENDV

241   FTPVRKIWDL FIHQCIQNYT PGAHLTIDEQ LLGFRGRCPF RMYIPNKPSK YGIKILMMCD

301   SGTKYMINGM PYLGRGTQTN GVPLGEYYVK ELSKPVHGSC RNITCDNWFT SIPLAKNLLQ

361   EPYKLTIVGT VRSNKREIPE VLKNSRSRPV GTSMFCFDGP LTLVSYKPKP AKMVYLLSSC

421   DEDASINEST GKPQMVMYYN QTKGGVDTLD QMCSVMTCSR KTNRWPMALL YGMINIACIN

481   SFIIYSHNVS SKGEKVQSRK KFMRNLYMSL TSSFMRKRLE APTLKRYLRD NISNILPNEV

541   PGTSDDSTEE PVMKKRTYCT YCPSKIRRKA NASCKKCKKV ICREHNIDMC QSCF.
```

The disclosure provides a composition comprising a transposon of the disclosure. In certain embodiments of the compositions comprising a transposon, the composition may further comprise a plasmid comprising a sequence encoding a transposase enzyme. The sequence encoding a transposase In certain embodiments of the methods of the disclosure, the transposase enzyme is a piggyBac™ (PB) transposase enzyme that comprises or consists of an amino acid sequence having an amino acid substitution at one or more of positions 30, 165, 282, or 538 of the sequence:

```
                                                         (SEQ ID NO: 1)
  1   MGSSLDDEHI LSALLQSDDE LVGEDSDSEI SDHVSEDDVQ SDTEEAFIDE VHEVQPTSSG

61   SEILDEQNVI EQPGSSLASN RILTLPQRTI RGKNKHCWST SKSTRRSRVS ALNIVRSQRG

121   PTRMCRNIYD PLLCFKLFFT DEIISEIVKW TNAEISLKRR ESMTGATFRD TNEDEIYAFF

181   GILVMTAVRK DNHMSTDDLF DRSLSMVYVS VMSRDRFDFL IRCLRMDDKS IRPTLRENDV

241   FTPVRKIWDL FIHQCIQNYT PGAHLTIDEQ LLGFRGRCPF RMYIPNKPSK YGIKILMMCD

301   SGTKYMINGM PYLGRGTQTN GVPLGEYYVK ELSKPVHGSC RNITCDNWFT SIPLAKNLLQ
```

```
361    EPYKLTIVGT  VRSNKREIPE  VLKNSRSRPV  GTSMFCFDGP  LTLVSYKPKP  AKMVYLLSSC

421    DEDASINEST  GKPQMVMYYN  QTKGGVDTLD  QMCSVMTCSR  KTNRWPMALL  YGMINIACIN

481    SFIIYSHNVS  SKGEKVQSRK  KFMRNLYMSL  TSSFMRKRLE  APTLKRYLRD  NISNILPNEV

541    PGTSDDSTEE  PVMKKRTYCT  YCPSKIRRKA  NASCKKCKKV  ICREHNIDMC  QSCF.
```

In certain embodiments, the transposase enzyme is a piggyBac™ (PB) transposase enzyme that comprises or consists of an amino acid sequence having an amino acid substitution at two or more of positions 30, 165, 282, or 538 of the sequence of SEQ ID NO: 1. In certain embodiments, the transposase enzyme is a piggyBac™ (PB) transposase enzyme that comprises or consists of an amino acid sequence having an amino acid substitution at three or more of positions 30, 165, 282, or 538 of the sequence of SEQ ID NO: 1. In certain embodiments, the transposase enzyme is a piggyBac™ (PB) transposase enzyme that comprises or consists of an amino acid sequence having an amino acid substitution at each of the following positions 30, 165, 282, and 538 of the sequence of SEQ ID NO: 1. In certain embodiments, the amino acid substitution at position 30 of the sequence of SEQ ID NO: 1 is a substitution of a valine (V) for an isoleucine (I). In certain embodiments, the amino acid substitution at position 165 of the sequence of SEQ ID NO: 1 is a substitution of a serine (S) for a glycine (G). In certain embodiments, the amino acid substitution at position 282 of the sequence of SEQ ID NO: 1 is a substitution of a valine (V) for a methionine (M). In certain embodiments, the amino acid substitution at position 538 of the sequence of SEQ ID NO: 1 is a substitution of a lysine (K) for an asparagine (N).

In certain embodiments of the methods of the disclosure, the transposase enzyme is a Super piggyBac™ (SPB) transposase enzyme. In certain embodiments, the Super piggyBac™ (SPB) transposase enzymes of the disclosure may comprise or consist of the amino acid sequence of the sequence of SEQ ID NO: 1 wherein the amino acid substitution at position 30 is a substitution of a valine (V) for an isoleucine (I), the amino acid substitution at position 165 is a substitution of a serine (S) for a glycine (G), the amino acid substitution at position 282 is a substitution of a valine (V) for a methionine (M), and the amino acid substitution at position 538 is a substitution of a lysine (K) for an aspara- gine (N). In certain embodiments, the Super piggyBac™ (SPB) transposase enzyme may comprise or consist of an amino acid sequence at least 75%, 80%, 85%, 90%, 95%, 99% or any percentage in between identical to:

```
                                                                (SEQ ID NO: 2)
  1    MGSSLDDEHI  LSALLQSDDE  LVGEDSDSEV  SDHVSEDDVQ  SDTEEAFIDE  VHEVQPTSSG

61    SEILDEQNVI  EQPGSSLASN  RILTLPQRTI  RGKNKHCWST  SKSTRRSRVS  ALNIVRSQRG

121    PTRMCRNIYD  PLLCFKLFFT  DEIISEIVKW  TNAEISLKRR  ESMTSATFRD  TNEDEIYAFF

181    GILVMTAVRK  DNHMSTDDLF  DRSLSMVYVS  VMSRDRFDFL  IRCLRMDDKS  IRPTLRENDV

241    FTPVRKIWDL  FIHQCIQNYT  PGAHLTIDEQ  LLGFRGRCPF  RVYIPNKPSK  YGIKILMMCD

301    SGTKYMINGM  PYLGRGTQTN  GVPLGEYYVK  ELSKPVHGSC  RNITCDNWFT  SIPLAKNLLQ

361    EPYKLTIVGT  VRSNKREIPE  VLKNSRSRPV  GTSMFCFDGP  LTLVSYKPKP  AKMVYLLSSC

421    DEDASINEST  GKPQMVMYYN  QTKGGVDTLD  QMCSVMTCSR  KTNRWPMALL  YGMINIACIN

481    SFIIYSHNVS  SKGEKVQSRK  KFMRNLYMSL  TSSFMRKRLE  APTLKRYLRD  NISNILPKEV

541    PGTSDDSTEE  PVMKKRTYCT  YCPSKIRRKA  NASCKKCKKV  ICREHNIDMC  QSCF.
```

In certain embodiments of the methods of the disclosure, including those embodiments wherein the transposase comprises the above-described mutations at positions 30, 165, 282 and/or 538, the piggyBac™ or Super piggyBac™ transposase enzyme may further comprise an amino acid substitution at one or more of positions 3, 46, 82, 103, 119, 125, 177, 180, 185, 187, 200, 207, 209, 226, 235, 240, 241, 243, 258, 296, 298, 311, 315, 319, 327, 328, 340, 421, 436, 456, 470, 486, 503, 552, 570 and 591 of the sequence of SEQ ID NO: 1 or SEQ ID NO: 2. In certain embodiments, including those embodiments wherein the transposase comprises the above-described mutations at positions 30, 165, 282 and/or 538, the piggyBac™ or Super piggyBac™ transposase enzyme may further comprise an amino acid substitution at one or more of positions 46, 119, 125, 177, 180, 185, 187, 200, 207, 209, 226, 235, 240, 241, 243, 296, 298, 311, 315, 319, 327, 328, 340, 421, 436, 456, 470, 485, 503, 552 and 570. In certain embodiments, the amino acid substitution at position 3 of SEQ ID NO: 1 or SEQ ID NO: 2 is a substitution of an asparagine (N) for a serine (S). In certain embodiments, the amino acid substitution at position 46 of SEQ ID NO: 1 or SEQ ID NO: 2 is a substitution of a serine (S) for an alanine (A). In certain embodiments, the amino acid substitution at position 46 of SEQ ID NO: 1 or SEQ ID NO: 2 is a substitution of a threonine (T) for an alanine (A). In certain embodiments, the amino acid substitution at position 82 of SEQ ID NO: 1 or SEQ ID NO: 2 is a substitution of a tryptophan (W) for an isoleucine (I). In certain embodiments, the amino acid substitution at position 103 of SEQ ID NO: 1 or SEQ ID NO: 2 is a substitution of a proline (P) for a serine (S). In certain embodiments, the amino acid substitution at position 119 of SEQ ID NO: 1 or SEQ ID NO: 2 is a substitution of a proline (P) for an arginine (R). In certain embodiments, the amino acid substitution at position 125 of SEQ ID NO: 1 or SEQ ID NO: 2 is a substitution of an alanine (A) a cysteine (C). In certain embodiments, the amino acid substitution at position 125 of SEQ ID NO: 1 or SEQ ID NO: 2 is a substitution of a leucine (L) for a cysteine (C). In certain embodiments, the amino acid substitution at position 177 of SEQ ID NO: 1 or SEQ ID NO: 2 is a substitution of a lysine (K) for a tyrosine (Y). In certain embodiments, the amino acid substitution at position 177 of SEQ ID NO: 1 or SEQ ID NO: 2 is a substitution of a histidine (H) for a tyrosine (Y). In certain embodiments, the amino acid substitution at position 180 of SEQ ID NO: 1 or SEQ ID NO: 2 is a substitution of a leucine (L) for a phenylalanine (F). In certain embodiments, the amino acid substitution at position 180 of SEQ ID NO: 1 or SEQ ID NO: 2 is a substitution of an isoleucine (I) for a phenylalanine (F). In certain embodiments, the amino acid substitution at position 180 of SEQ ID NO: 1 or SEQ ID NO: 2 is a substitution of a valine (V) for a phenylalanine (F). In certain embodiments, the amino acid substitution at position 185 of SEQ ID NO: 1 or SEQ ID NO: 2 is a substitution of a leucine (L) for a methionine (M). In certain embodiments, the amino acid substitution at position 187 of SEQ ID NO: 1 or SEQ ID NO: 2 is a substitution of a glycine (G) for an alanine (A). In certain embodiments, the amino acid substitution at position 200 of SEQ ID NO: 1 or SEQ ID NO: 2 is a substitution of a tryptophan (W) for a phenylalanine (F). In certain embodiments, the amino acid substitution at position 207 of SEQ ID NO: 1 or SEQ ID NO: 2 is a substitution of a proline (P) for a valine (V). In certain embodiments, the amino acid substitution at position 209 of SEQ ID NO: 1 or SEQ ID NO: 2 is a substitution of a phenylalanine (F) for a valine (V). In certain embodiments, the amino acid substitution at position 226 of SEQ ID NO: 1 or SEQ ID NO: 2 is a substitution of a phenylalanine (F) for a methionine (M). In certain embodiments, the amino acid substitution at position 235 of SEQ ID NO: 1 or SEQ ID NO: 2 is a substitution of an arginine (R) for a leucine (L). In certain embodiments, the amino acid substitution at position 240 of SEQ ID NO: 1 or SEQ ID NO: 1 is a substitution of a lysine (K) for a valine (V). In certain embodiments, the amino acid substitution at position 241 of SEQ ID NO: 1 or SEQ ID NO: 2 is a substitution of a leucine (L) for a phenylalanine (F). In certain embodiments, the amino acid substitution at position 243 of SEQ ID NO: 1 or SEQ ID NO: 2 is a substitution of a lysine (K) for a proline (P). In certain embodiments, the amino acid substitution at position 258 of SEQ ID NO: 1 or SEQ ID NO: 2 is a substitution of a serine (S) for an asparagine (N). In certain embodiments, the amino acid substitution at position 296 of SEQ ID NO: 1 or SEQ ID NO: 2 is a substitution of a tryptophan (W) for a leucine (L). In certain embodiments, the amino acid substitution at position 296 of SEQ ID NO: 1 or SEQ ID NO: 2 is a substitution of a tyrosine (Y) for a leucine (L). In certain embodiments, the amino acid substitution at position 296 of SEQ ID NO: 1 or SEQ ID NO: 2 is a substitution of a phenylalanine (F) for a leucine (L). In certain embodiments, the amino acid substitution at position 298 of SEQ ID NO: 1 or SEQ ID NO: 2 is a substitution of a leucine (L) for a methionine (M). In certain embodiments, the amino acid substitution at position 298 of SEQ ID NO: 1 or SEQ ID NO: 2 is a substitution of an alanine (A) for a methionine (M). In certain embodiments, the amino acid substitution at position 298 of SEQ ID NO: 1 or SEQ ID NO: 2 is a substitution of a valine (V) for a methionine (M). In certain embodiments, the amino acid substitution at position 311 of SEQ ID NO: 1 or SEQ ID NO: 2 is a substitution of an isoleucine (I) for a proline (P). In certain embodiments, the amino acid substitution at position 311 of SEQ ID NO: 1 or SEQ ID NO: 2 is a substitution of a valine for a proline (P). In certain embodiments, the amino acid substitution at position 315 of SEQ ID NO: 1 or SEQ ID NO: 2 is a substitution of a lysine (K) for an arginine (R). In certain embodiments, the amino acid substitution at position 319 of SEQ ID NO: 1 or SEQ ID NO: 2 is a substitution of a glycine (G) for a threonine (T). In certain embodiments, the amino acid substitution at position 327 of SEQ ID NO: 1 or SEQ ID NO: 2 is a substitution of an arginine (R) for a tyrosine (Y). In certain embodiments, the amino acid substitution at position 328 of SEQ ID NO: 1 or SEQ ID NO: 2 is a substitution of a valine (V) for a tyrosine (Y). In certain embodiments, the amino acid substitution at position 340 of SEQ ID NO: 1 or SEQ ID NO: 2 is a substitution of a glycine (G) for a cysteine (C). In certain embodiments, the amino acid substitution at position 340 of SEQ ID NO: 1 or SEQ ID NO: 2 is a substitution of a leucine (L) for a cysteine (C). In certain embodiments, the amino acid substitution at position 421 of SEQ ID NO: 1 or SEQ ID NO: 2 is a substitution of a histidine (H) for the aspartic acid (D). In certain embodiments, the amino acid substitution at position 436 of SEQ ID NO: 1 or SEQ ID NO: 2 is a substitution of an isoleucine (I) for a valine (V). In certain embodiments, the amino acid substitution at position 456 of SEQ ID NO: 1 or SEQ ID NO: 2 is a substitution of a tyrosine (Y) for a methionine (M). In certain embodiments, the amino acid substitution at position 470 of SEQ ID NO: 1 or SEQ ID NO: 2 is a substitution of a phenylalanine (F) for a leucine (L). In certain embodiments, the amino acid substitution at position 485 of SEQ ID NO: 1 or SEQ ID NO: 2 is a substitution of a lysine (K) for a serine (S). In certain embodiments, the amino acid substitution at position 503 of SEQ ID NO: 1 or SEQ ID NO: 2 is a substitution of a leucine (L) for a methionine (M). In certain embodiments, the amino acid substitution at position 503 of SEQ ID NO: 1 or SEQ ID NO: 2 is a substitution of an isoleucine (I) for a methionine (M). In certain embodiments, the amino acid substitution at position 552 of SEQ ID NO: 1 or SEQ ID NO: 2 is a substitution of a lysine (K) for a valine (V). In certain embodiments, the amino acid substitution at position 570 of SEQ ID NO: 1 or SEQ ID NO: 2 is a substitution of a threonine (T) for an alanine (A). In certain embodiments, the amino acid substitution at position 591 of SEQ ID NO: 1 or SEQ ID NO: 2 is a substitution of a proline (P) for a glutamine (Q). In certain embodiments, the amino acid substitution at position 591 of SEQ ID NO: 1 or SEQ ID NO: 2 is a substitution of an arginine (R) for a glutamine (Q).

In certain embodiments of the methods of the disclosure, including those embodiments wherein the transposase comprises the above-described mutations at positions 30, 165, 282 and/or 538, the piggyBac™ transposase enzyme may comprise or the Super piggyBac™ transposase enzyme may further comprise an amino acid substitution at one or more of positions 103, 194, 372, 375, 450, 509 and 570 of the sequence of SEQ ID NO: 1 or SEQ ID NO: 2. In certain embodiments of the methods of the disclosure, including those embodiments wherein the transposase comprises the above-described mutations at positions 30, 165, 282 and/or 538, the piggyBac™ transposase enzyme may comprise or the Super piggyBac™ transposase enzyme may further comprise an amino acid substitution at two, three, four, five, six or more of positions 103, 194, 372, 375, 450, 509 and 570 of the sequence of SEQ ID NO: 1 or SEQ ID NO: 2. In certain embodiments, including those embodiments wherein the transposase comprises the above-described mutations at positions 30, 165, 282 and/or 538, the piggyBac™ transposase enzyme may comprise or the Super piggyBac™ transposase enzyme may further comprise an amino acid substitution at positions 103, 194, 372, 375, 450, 509 and 570 of the sequence of SEQ ID NO: 1 or SEQ ID NO: 2. In certain embodiments, the amino acid substitution at position 103 of SEQ ID NO: 1 or SEQ ID NO: 2 is a substitution of a proline (P) for a serine (S). In certain embodiments, the amino acid substitution at position 194 of SEQ ID NO: 1 or SEQ ID NO: 2 is a substitution of a valine (V) for a methionine (M). In certain embodiments, the amino acid substitution at position 372 of SEQ ID NO: 1 or SEQ ID NO: 2 is a substitution of an alanine (A) for an arginine (R). In certain embodiments, the amino acid substitution at position 375 of SEQ ID NO: 1 or SEQ ID NO: 2 is a substitution of an alanine (A) for a lysine (K). In certain embodiments, the amino acid substitution at position 450 of SEQ ID NO: 1 or SEQ ID NO: 2 is a substitution of an asparagine (N) for an aspartic acid (D). In certain embodiments, the amino acid substitution at position 509 of SEQ ID NO: 1 or SEQ ID NO: 2 is a substitution of a glycine (G) for a serine (S). In certain embodiments, the amino acid substitution at position 570 of SEQ ID NO: 1 or SEQ ID NO: 2 is a substitution of a serine (S) for an asparagine (N). In certain embodiments, the piggyBac™ transposase enzyme may comprise a substitution of a valine (V) for a methionine (M) at position 194 of SEQ ID NO: 1. In certain embodiments, including those embodiments wherein the piggyBac™ transposase enzyme may comprise a substitution of a valine (V) for a methionine (M) at position 194 of SEQ ID NO: 1, the piggyBac™ transposase enzyme may further comprise an amino acid substitution at positions 372, 375 and 450 of the sequence of SEQ ID NO: 1 or SEQ ID NO: 2. In certain embodiments, the piggyBac™ transposase enzyme may comprise a substitution of a valine (V) for a methionine (M) at position 194 of SEQ ID NO: 1, a substitution of an alanine (A) for an arginine (R) at position 372 of SEQ ID NO: 1, and a substitution of an alanine (A) for a lysine (K) at position 375 of SEQ ID NO: 1. In certain embodiments, the piggyBac™ transposase enzyme may comprise a substitution of a valine (V) for a methionine (M) at position 194 of SEQ ID NO: 1, a substitution of an alanine (A) for an arginine (R) at position 372 of SEQ ID NO: 1, a substitution of an alanine (A) for a lysine (K) at position 375 of SEQ ID NO: 1 and a substitution of an asparagine (N) for an aspartic acid (D) at position 450 of SEQ ID NO: 1.

The disclosure provides a composition comprising a transposon of the disclosure. In certain embodiments of this method, the transposon is a plasmid DNA transposon with a sequence encoding the inducible caspase polypeptide of the disclosure flanked by two cis-regulatory insulator elements. In certain embodiments of the compositions comprising a transposon, the composition may further comprise a plasmid comprising a sequence encoding a transposase enzyme. The sequence encoding a transposase enzyme may be an mRNA sequence. In certain embodiments, the transposon is a Sleeping Beauty transposon. In certain embodiments, the transposon is a Sleeping Beauty transposon and the transposase is a Sleeping Beauty transposase or a hyperactive Sleeping Beauty (SB100X) transposase.

Transposons of the disclosure may comprise Sleeping Beauty transposons. In certain embodiments, and, in particular, those embodiments wherein the transposon is a Sleeping Beauty transposon, the composition further comprises a plasmid comprising a sequence encoding a transposase enzyme. In certain embodiments, the sequence encoding the transposase enzyme is a sequence encoding a Sleeping Beauty transposase or a hyperactive Sleeping Beauty (SB100X) transposase. In certain embodiments, the sequence encoding the transposase enzyme is an mRNA sequence.

In certain embodiments of the methods of the disclosure, the Sleeping Beauty transposase enzyme comprises an amino acid sequence at least 75%, 80%, 85%, 90%, 95%, 99% or any percentage in between identical to:

```
                                                      (SEQ ID NO: 19)
  1    MGKSKEISQD LRKKIVDLHK SGSSLGAISK RLKVPRSSVQ TIVRKYKHHG TTQPSYRSGR

61    RRVLSPRDER TLVRKVQINP RTTAKDLVKM LEETGTKVSI STVKRVLYRH NLKGRSARKK

121    PLLQNRHKKA RLRFATAHGD KDRTFWRNVL WSDETKIELF GHNDHRYVWR KKGEACKPKN

181    TIPTVKHGGG SIMLWGCFAA GGTGALHKID GIMRKENYVD ILKQHLKTSV RKLKLGRKWV

241    FQMDNDPKHT SKVVAKWLKD NKVKVLEWPS QSPDLNPIEN LWAELKKRVR ARRPTNLTQL

301    HQLCQEEWAK IHPTYCGKLV EGYPKRLTQV KQFKGNATKY.
```

In certain embodiments of the methods of the disclosure, the hyperactive Sleeping Beauty (SB100X) transposase enzyme comprises an amino acid sequence at least 75%, 80%, 85%, 90%, 95%, 99% or any percentage in between identical to:

```
                                                      (SEQ ID NO: 20)
  1    MGKSKEISQD LRKRIVDLHK SGSSLGAISK RLAVPRSSVQ TIVRKYKHHG TTQPSYRSGR

61    RRVLSPRDER TLVRKVQINP RTTAKDLVKM LEETGTKVSI STVKRVLYRH NLKGHSARKK

121    PLLQNRHKKA RLRFATAHGD KDRTFWRNVL WSDETKIELF GHNDHRYVWR KKGEACKPKN

181    TIPTVKHGGG SIMLWGCFAA GGTGALHKID GIMDAVQYVD ILKQHLKTSV RKLKLGRKWV

241    FQHDNDPKHT SKVVAKWLKD NKVKVLEWPS QSPDLNPIEN LWAELKKRVR ARRPTNLTQL

301    HQLCQEEWAK IHPNYCGKLV EGYPKRLTQV KQFKGNATKY.
```

The disclosure provides a composition comprising a transposon of the disclosure. In certain embodiments of this method, the transposon is a plasmid DNA transposon with a sequence encoding the inducible caspase polypeptide of the disclosure flanked by two cis-regulatory insulator elements. In certain embodiments of the compositions comprising a transposon, the composition may further comprise a plasmid comprising a sequence encoding a transposase enzyme. The sequence encoding a transposase enzyme may be an mRNA sequence. In certain embodiments, the transposon is a Helraiser transposon. In certain embodiments, the transposon is a Helraiser transposon and the transposase is a Helitron transposase.

Transposons of the disclosure may comprise Helraiser transposons. In certain embodiments of this method, the transposon is a plasmid DNA transposon with a sequence encoding the inducible caspase polypeptide of the disclosure flanked by two cis-regulatory insulator elements. In certain embodiments of this method, the transposon is a Helraiser transposon. In certain embodiments, and, in particular, those embodiments wherein the transposon is a Helraiser transposon, the composition further comprises a plasmid comprising a sequence encoding a transposase enzyme. In certain embodiments, the sequence encoding the transposase enzyme comprises a sequence encoding a Helitron transposase. In certain embodiments, the sequence encoding the transposase enzyme is an mRNA sequence.

In certain embodiments, the transposase is a Helitron transposase. Helitron transposases mobilize the Helraiser transposon, an ancient element from the bat genome that was active about 30 to 36 million years ago. An exemplary Helraiser transposon of the disclosure includes Helibat1, which comprises a nucleic acid sequence comprising:

```
                                                           (SEQ ID NO: 21)
   1 TCCTATATAA TAAAAGAGAA ACATGCAAAT TGACCATCCC TCCGCTACGC TCAAGCCACG

61 CCCACCAGCC AATCAGAAGT GACTATGCAA ATTAACCCAA CAAAGATGGC AGTTAAATTT

121 GCATACGCAG GTGTCAAGCG CCCCAGGAGG CAACGGCGGC CGCGGGCTCC CAGGACCTTC

181 GCTGGCCCCG GGAGGCGAGG CCGGCCGCGC CTAGCCACAC CCGCGGGCTC CCGGGACCTT

241 CGCCAGCAGA GAGCAGAGCG GGAGAGCGGG CGGAGAGCGG GAGGTTTGGA GGACTTGGCA

301 GAGCAGGAGG CCGCTGGACA TAGAGCAGAG CGAGAGAGAG GGTGGCTTGG AGGGCGTGGC

361 TCCCTCTGTC ACCCCAGCTT CCTCATCACA GCTGTGGAAA CTGACAGCAG GGAGGAGGAA

421 GTCCCACCCC CACAGAATCA GCCAGAATCA GCCGTTGGTC AGACAGCTCT CAGCGGCCTG

481 ACAGCCAGGA CTCTCATTCA CCTGCATCTC AGACCGTGAC AGTAGAGAGG TGGGACTATG

541 TCTAAAGAAC AACTGTTGAT ACAACGTAGC TCTGCAGCCG AAAGATGCCG GCGTTATCGA

601 CAGAAAATGT CTGCAGAGCA ACGTGCGTCT GATCTTGAAA GAAGGCGGCG CCTGCAACAG

661 AATGTATCTG AAGAGCAGCT ACTGGAAAAA CGTCGCTCTG AAGCCGAAAA ACAGCGGCGT

721 CATCGACAGA AAATGTCTAA AGACCAACGT GCCTTTGAAG TTGAAAGAAG GCGGTGGCGA

781 CGACAGAATA TGTCTAGAGA ACAGTCATCA ACAAGTACTA CCAATACCGG TAGGAACTGC

841 CTTCTCAGCA AAAATGGAGT ACATGAGGAT GCAATTCTCG AACATAGTTG TGGTGGAATG

901 ACTGTTCGAT GTGAATTTTG CCTATCACTA AATTTCTCTG ATGAAAAACC ATCCGATGGG

961 AAATTTACTC GATGTTGTAG CAAAGGGAAA GTCTGTCCAA ATGATATACA TTTTCCAGAT

1021 TACCCGGCAT ATTTAAAAAG ATTAATGACA AACGAAGATT CTGACAGTAA AAATTTCATG

1081 GAAAATATTC GTTCCATAAA TAGTTCTTTT GCTTTTGCTT CCATGGGTGC AAATATTGCA

1141 TCGCCATCAG GATATGGGCC ATACTGTTTT AGAATACACG GACAAGTTTA TCACCGTACT

1201 GGAACTTTAC ATCCTTCGGA TGGTGTTTCT CGGAAGTTTG CTCAACTCTA TATTTTGGAT

1261 ACAGCCGAAG CTACAAGTAA AAGATTAGCA ATGCCAGAAA ACCAGGGCTG CTCAGAAAGA

1321 CTCATGATCA ACATCAACAA CCTCATGCAT GAAATAAATG AATTAACAAA ATCGTACAAG

1381 ATGCTACATG AGGTAGAAAA GGAAGCCCAA TCTGAAGCAG CAGCAAAAGG TATTGCTCCC

1441 ACAGAAGTAA CAATGGCGAT TAAATACGAT CGTAACAGTG ACCCAGGTAG ATATAATTCT

1501 CCCCGTGTAA CCGAGGTTGC TGTCATATTC AGAAACGAAG ATGGAGAACC TCCTTTTGAA

1561 AGGGACTTGC TCATTCATTG TAAACCAGAT CCCAATAATC CAAATGCCAC TAAAATGAAA

1621 CAAATCAGTA TCCTGTTTCC TACATTAGAT GCAATGACAT ATCCTATTCT TTTTCCACAT

1681 GGTGAAAAAG CTGGGGAAC AGATATTGCA TTAAGACTCA GAGACAACAG TGTAATCGAC

1741 AATAATACTA GACAAAATGT AAGGACACGA GTCACACAAA TGCAGTATTA TGGATTTCAT
```

-continued

```
1801  CTCTCTGTGC GGGACACGTT CAATCCTATT TTAAATGCAG GAAAATTAAC TCAACAGTTT

1861  ATTGTGGATT CATATTCAAA AATGGAGGCC AATCGGATAA ATTTCATCAA AGCAAACCAA

1921  TCTAAGTTGA GAGTTGAAAA ATATAGTGGT TTGATGGATT ATCTCAAATC TAGATCTGAA

1981  AATGACAATG TGCCGATTGG TAAAATGATA ATACTTCCAT CATCTTTTGA GGGTAGTCCC

2041  AGAAATATGC AGCAGCGATA TCAGGATGCT ATGGCAATTG TAACGAAGTA TGGCAAGCCC

2101  GATTTATTCA TAACCATGAC ATGCAACCCC AAATGGGCAG ATATTACAAA CAATTTACAA

2161  CGCTGGCAAA AGTTGAAAA CAGACCTGAC TTGGTAGCCA GAGTTTTTAA TATTAAGCTG

2221  AATGCTCTTT TAAATGATAT ATGTAAATTC CATTTATTTG GCAAAGTAAT AGCTAAAATT

2281  CATGTCATTG AATTTCAGAA ACGCGGACTG CCTCACGCTC ACATATTATT GATATTAGAT

2341  AGTGAGTCCA AATTACGTTC AGAAGATGAC ATTGACCGTA TAGTTAAGGC AGAAATTCCA

2401  GATGAAGACC AGTGTCCTCG ACTTTTTCAA ATTGTAAAAT CAAATATGGT ACATGGACCA

2461  TGTGGAATAC AAAATCCAAA TAGTCCATGT ATGGAAAATG GAAAATGTTC AAAGGGATAT

2521  CCAAAAGAAT TTCAAAATGC GACCATTGGA AATATTGATG GATATCCCAA ATACAAACGA

2581  AGATCTGGTA GCACCATGTC TATTGGAAAT AAAGTTGTCG ATAACACTTG GATTGTCCCT

2641  TATAACCCGT ATTTGTGCCT TAAATATAAC TGTCATATAA ATGTTGAAGT CTGTGCATCA

2701  ATTAAAAGTG TCAAATATTT ATTTAAATAC ATCTATAAAG GGCACGATTG TGCAAATATT

2761  CAAATTTCTG AAAAAATAT TATCAATCAT GACGAAGTAC AGGACTTCAT TGACTCCAGG

2821  TATGTGAGCG CTCCTGAGGC TGTTTGGAGA CTTTTTGCAA TGCGAATGCA TGACCAATCT

2881  CATGCAATCA CAAGATTAGC TATTCATTTG CCAAATGATC AGAATTTGTA TTTTCATACC

2941  GATGATTTTG CTGAAGTTTT AGATAGGGCT AAAAGGCATA ACTCGACTTT GATGGCTTGG

3001  TTCTTATTGA ATAGAGAAGA TTCTGATGCA CGTAATTATT ATTATTGGGA GATTCCACAG

3061  CATTATGTGT TTAATAATTC TTTGTGGACA AAACGCCGAA AGGGTGGGAA TAAAGTATTA

3121  GGTAGACTGT TCACTGTGAG CTTTAGAGAA CCAGAACGAT ATTACCTTAG ACTTTTGCTT

3181  CTGCATGTAA AAGGTGCGAT AAGTTTTGAG GATCTGCGAA CTGTAGGAGG TGTAACTTAT

3241  GATACATTTC ATGAAGCTGC TAAACACCGA GGATTATTAC TTGATGACAC TATCTGGAAA

3301  GATACGATTG ACGATGCAAT CATCCTTAAT ATGCCCAAAC AACTACGGCA ACTTTTTGCA

3361  TATATATGTG TGTTTGGATG TCCTTCTGCT GCAGACAAAT TATGGGATGA GAATAAATCT

3421  CATTTTATTG AAGATTTCTG TTGGAAATTA CACCGAAGAG AAGGTGCCTG TGTGAACTGT

3481  GAAATGCATG CCCTTAACGA AATTCAGGAG GTATTCACAT TGCATGGAAT GAAATGTTCA

3541  CATTTCAAAC TTCCGGACTA TCCTTTATTA ATGAATGCAA ATACATGTGA TCAATTGTAC

3601  GAGCAACAAC AGGCAGAGGT TTTGATAAAT TCTCTGAATG ATGAACAGTT GGCAGCCTTT

3661  CAGACTATAA CTTCAGCCAT CGAAGATCAA ACTGTACACC CCAAATGCTT TTTCTTGGAT

3721  GGTCCAGGTG GTAGTGGAAA ACATATCTG TATAAAGTTT TAACACATTA TATTAGAGGT

3781  CGTGGTGGTA CTGTTTTACC CACAGCATCT ACAGGAATTG CTGCAAATTT ACTTCTTGGT

3841  GGAAGAACCT TTCATTCCCA ATATAAATTA CCAATTCCAT TAAATGAAAC TTCAATTTCT

3901  AGACTCGATA TAAAGAGTGA AGTTGCTAAA ACCATTAAAA AGGCCCAACT TCTCATTATT

3961  GATGAATGCA CCATGGCATC CAGTCATGCT ATAAACGCCA TAGATAGATT ACTAAGAGAA

4021  ATTATGAATT TGAATGTTGC ATTTGGTGGG AAAGTTCTCC TTCTCGGAGG GGATTTTCGA

4081  CAATGTCTCA GTATTGTACC ACATGCTATG CGATCGGCCA TAGTACAAAC GAGTTTAAAG

4141  TACTGTAATG TTTGGGGATG TTTCAGAAAG TTGTCTCTTA AACAAATAT GAGATCAGAG

4201  GATTCTGCTT ATAGTGAATG GTTAGTAAAA CTTGGAGATG GCAAACTTGA TAGCAGTTTT
```

```
-continued
4261  CATTTAGGAA TGGATATTAT TGAAATCCCC CATGAAATGA TTTGTAACGG ATCTATTATT

4321  GAAGCTACCT TTGGAAATAG TATATCTATA GATAATATTA AAAATATATC TAAACGTGCA

4381  ATTCTTTGTC CAAAAAATGA GCATGTTCAA AAATTAAATG AAGAAATTTT GGATATACTT

4441  GATGGAGATT TTCACACATA TTTGAGTGAT GATTCCATTG ATTCAACAGA TGATGCTGAA

4501  AAGGAAAATT TTCCCATCGA ATTTCTTAAT AGTATTACTC CTTCGGGAAT GCCGTGTCAT

4561  AAATTAAAAT TGAAAGTGGG TGCAATCATC ATGCTATTGA GAAATCTTAA TAGTAAATGG

4621  GGTCTTTGTA ATGGTACTAG ATTTATTATC AAAAGATTAC GACCTAACAT TATCGAAGCT

4681  GAAGTATTAA CAGGATCTGC AGAGGGAGAG GTTGTTCTGA TTCCAAGAAT TGATTTGTCC

4741  CCATCTGACA CTGGCCTCCC ATTTAAATTA ATTCGAAGAC AGTTTCCCGT GATGCCAGCA

4801  TTTGCGATGA CTATTAATAA ATCACAAGGA CAAACTCTAG ACAGAGTAGG AATATTCCTA

4861  CCTGAACCCG TTTTCGCACA TGGTCAGTTA TATGTTGCTT TCTCTCGAGT TCGAAGAGCA

4921  TGTGACGTTA AAGTTAAAGT TGTAAATACT TCATCACAAG GGAAATTAGT CAAGCACTCT

4981  GAAAGTGTTT TTACTCTTAA TGTGGTATAC AGGGAGATAT TAGAATAAGT TTAATCACTT

5041  TATCAGTCAT TGTTTGCATC AATGTTGTTT TTATATCATG TTTTTGTTGT TTTTATATCA

5101  TGTCTTTGTT GTTGTTATAT CATGTTGTTA TTGTTTATTT ATTAATAAAT TTATGTATTA

5161  TTTTCATATA CATTTTACTC ATTTCCTTTC ATCTCTCACA CTTCTATTAT AGAGAAAGGG

5221  CAAATAGCAA TATTAAAATA TTTCCTCTAA TTAATTCCCT TTCAATGTGC ACGAATTTCG

5281  TGCACCGGGC CACTAG.
```

Unlike other transposases, the Helitron transposase does not contain an RNase-H like catalytic domain, but instead comprises a RepHel motif made up of a replication initiator domain (Rep) and a DNA helicase domain. The Rep domain is a nuclease domain of the HUH superfamily of nucleases.

An exemplary Helitron transposase of the disclosure comprises an amino acid sequence comprising:

```
                                                            (SEQ ID NO 22)
  1  MSKEQLLIQR SSAAERCRRY RQKMSAEQRA SDLERRRRLQ QNVSEEQLLE KRRSEAEKQR

61  RHRQKMSKDQ RAFEVERRRW RRQNMSREQS STSTTNTGRN CLLSKNGVHE DAILEHSCGG

121  MTVRCEFCLS LNFSDEKPSD GKFTRCCSKG KVCPNDIHFP DYPAYLKRLM TNEDSDSKNF

181  MENIRSINSS FAFASMGANI ASPSGYGPYC FRIHGQVYHR TGTLHPSDGV SRKFAQLYIL

241  DTAEATSKRL AMPENQGCSE RLMININNLM HEINELTKSY KMLHEVEKEA QSEAAAKGIA

301  PTEVTMAIKY DRNSDPGRYN SPRVTEVAVI FRNEDGEPPF ERDLLIHCKP DPNNPNATKM

361  KQISILFPTL DAMTYPILFP HGEKGWGTDI ALRLRDNSVI DNNTRQNVRT RVTQMQYYGF

421  HLSVRDTFNP ILNAGKLTQQ FIVDSYSKME ANRINFIKAN QSKLRVEKYS GLMDYLKSRS

481  ENDNVPIGKM IILPSSFEGS PRNMQQRYQD AMAIVTKYGK PDLFITMTCN PKWADITNNL

541  QRWQKVENRP DLVARVFNIK LNALLNDICK FHLFGKVIAK IHVIEFQKRG LPHAHILLIL

601  DSESKLRSED DIDRIVKAEI PDEDQCPRLF QIVKSNMVHG PCGIQNPNSP CMENGKCSKG

661  YPKEFQNATI GNIDGYPKYK RRSGSTMSIG NKVVDNTWIV PYNPYLCLKY NCHINVEVCA

721  SIKSVKYLFK YIYKGHDCAN IQISEKNIIN HDEVQDFIDS RYVSAPEAVW RLFAMRMHDQ

781  SHAITRLAIH LPNDQNLYFH TDDFAEVLDR AKRHNSTLMA WFLLNREDSD ARNYYYWEIP

841  QHYVFNNSLW TKRRKGGNKV LGRLFTVSFR EPERYYLRLL LLHVKGAISF EDLRTVGGVT

901  YDTFHEAAKH RGLLLDDTIW KDTIDDAIIL NMPKQLRQLF AYICVFGCPS AADKLWDENK
```

-continued

```
 961  SHFIEDFCWK LHRREGACVN CEMHALNEIQ EVFTLHGMKC SHFKLPDYPL LMNANTCDQL

1021  YEQQQAEVLI NSLNDEQLAA FQTITSAIED QTVHPKCFFL DGPGGSGKTY LYKVLTHYIR

1081  GRGGTVLPTA STGIAANLLL GGRTFHSQYK LPIPLNETSI SRLDIKSEVA KTIKKAQLLI

1141  IDECTMASSH AINAIDRLLR EIMNLNVAFG GKVLLLGGDF RQCLSIVPHA MRSAIVQTSL

1201  KYCNVWGCFR KLSLKTNMRS EDSAYSEWLV KLGDGKLDSS FHLGMDIIEI PHEMICNGSI

1261  IEATFGNSIS IDNIKNISKR AILCPKNEHV QKLNEEILDI LDGDFHTYLS DDSIDSTDDA

1321  EKENFPIEFL NSITPSGMPC HKLKLKVGAI IMLLRNLNSK WGLCNGTRFI IKRLRPNIIE

1381  AEVLTGSAEG EVVLIPRIDL SPSDTGLPFK LIRRQFPVMP AFAMTINKSQ GQTLDRVGIF

1441  LPEPVFAHGQ LYVAFSRVRR ACDVKVKVVN TSSQGKLVKH SESVFTLNVV YREILE.
```

In Helitron transpositions, a hairpin close to the 3' end of the transposon functions as a terminator. However, this hairpin can be bypassed by the transposase, resulting in the transduction of flanking sequences. In addition, Helraiser transposition generates covalently closed circular intermediates. Furthermore, Helitron transpositions can lack target site duplications. In the Helraiser sequence, the transposase is flanked by left and right terminal sequences termed LTS and RTS. These sequences terminate with a conserved 5'-TC/CTAG-3' motif. A 19 bp palindromic sequence with the potential to form the hairpin termination structure is located 11 nucleotides upstream of the RTS and consists of the sequence (SEQ ID NO: 23)
GTGCACGAATTTCGTGCACCGGGCCACTAG.

The disclosure provides a composition comprising a transposon of the disclosure. In certain embodiments of this method, the transposon is a plasmid DNA transposon with a sequence encoding the inducible caspase polypeptide of the disclosure flanked by two cis-regulatory insulator elements. In certain embodiments of the compositions comprising a transposon, the composition may further comprise a plasmid comprising a sequence encoding a transposase enzyme. The sequence encoding a transposase enzyme may be an mRNA sequence. In certain embodiments, the transposon is a Tol2 transposon. In certain embodiments, the transposon is a Tol2 transposon and the transposase is a Tol2 transposase.

Transposons of the disclosure may comprise Tol2 transposons. In certain embodiments of this method, the transposon is a plasmid DNA transposon with a sequence encoding the inducible caspase polypeptide of the disclosure flanked by two cis-regulatory insulator elements. In certain embodiments of this method, the transposon is a Tol2 transposon. In certain embodiments, and, in particular, those embodiments wherein the transposon is a Tol2 transposon, the composition further comprises a plasmid comprising a sequence encoding a transposase enzyme. In certain embodiments, the sequence encoding the transposase enzyme comprises a sequence encoding a Tol2 transposase. In certain embodiments, the sequence encoding the transposase enzyme is an mRNA sequence.

Tol2 transposons may be isolated or derived from the genome of the medaka fish, and may be similar to transposons of the hAT family. Exemplary Tol2 transposons of the disclosure are encoded by a sequence comprising about 4.7 kilobases and contain a gene encoding the Tol2 transposase, which contains four exons. An exemplary Tol2 transposase of the disclosure comprises an amino acid sequence comprising the following:

```
                                                           (SEQ ID NO: 24)
  1   MEEVCDSSAA ASSTVQNQPQ DQEHPWPYLR EFFSLSGVNK DSFKMKCVLC LPLNKEISAF

61   KSSPSNLRKH IERMHPNYLK NYSKLTAQKR KIGTSTHASS SKQLKVDSVF PVKHVSPVTV

121   NKAILRYIIQ GLHPFSTVDL PSFKELISTL QPGISVITRP TLRSKIAEAA LIMKQKVTAA

181   MSEVEWIATT TDCWTARRKS FIGVTAHWIN PGSLERHSAA LACKRLMGSH TFEVLASAMN

241   DIHSEYEIRD KVVCTTTDSG SNFMKAFRVF GVENNDIETE ARRCESDDTD SEGCGEGSDG

301   VEFQDASRVL DQDDGFEFQL PKHQKCACHL LNLVSSVDAQ KALSNEHYKK LYRSVFGKCQ

361   ALWNKSSRSA LAAEAVESES RLQLLRPNQT RWNSTFMAVD RILQICKEAG EGALRNICTS

421   LEVPMFNPAE MLFLTEWANT MRPVAKVLDI LQAETNTQLG WLLPSVHQLS LKLQRLHHSL

481   RYCDPLVDAL QQGIQTRFKH MFEDPEIIAA AILLPKFRTS WTNDETIIKR GMDYIRVHLE

541   PLDHKKELAN SSSDDEDFFA SLKPTTHEAS KELDGYLACV SDTRESLLTF PAICSLSIKT

601   NTPLPASAAC ERLFSTAGLL FSPKRARLDT NNFENQLLLK LNLRFYNFE.
```

An exemplary Tol2 transposon of the disclosure, including inverted repeats, subterminal sequences and the Tol2 transposase, is encoded by a nucleic acid sequence comprising the following:

(SEQ ID NO: 25)

```
   1 CAGAGGTGTA AAGTACTTGA GTAATTTTAC TTGATTACTG TACTTAAGTA TTATTTTTGG
  61 GGATTTTTAC TTTACTTGAG TACAATTAAA AATCAATACT TTTACTTTTA CTTAATTACA
 121 TTTTTTTAGA AAAAAAGTA CTTTTTACTC CTTACAATTT TATTTACAGT CAAAAAGTAC
 181 TTATTTTTTG GAGATCACTT CATTCTATTT TCCCTTGCTA TTACCAAACC AATTGAATTG
 241 CGCTGATGCC CAGTTTAATT TAAATGTTAT TTATTCTGCC TATGAAAATC GTTTTCACAT
 301 TATATGAAAT TGGTCAGACA TGTTCATTGG TCCTTTGGAA GTGACGTCAT GTCACATCTA
 361 TTACCACAAT GCACAGCACC TTGACCTGGA AATTAGGGAA ATTATAACAG TCAATCAGTG
 421 GAAGAAAATG GAGGAAGTAT GTGATTCATC AGCAGCTGCG AGCAGCACAG TCCAAAATCA
 481 GCCACAGGAT CAAGAGCACC CGTGGCCGTA TCTTCGCGAA TTCTTTTCTT TAAGTGGTGT
 541 AAATAAAGAT TCATTCAAGA TGAAATGTGT CCTCTGTCTC CCGCTTAATA AAGAAATATC
 601 GGCCTTCAAA AGTTCGCCAT CAAACCTAAG GAAGCATATT GAGGTAAGTA CATTAAGTAT
 661 TTTGTTTTAC TGATAGTTTT TTTTTTTTTT TTTTTTTTTT TTTTGGGTG TGCATGTTTT
 721 GACGTTGATG GCGCGCCTTT TATATGTGTA GTAGGCCTAT TTTCACTAAT GCATGCGATT
 781 GACAATATAA GGCTCACGTA ATAAAATGCT AAAATGCATT TGTAATTGGT AACGTTAGGT
 841 CCACGGGAAA TTTGGCGCCT ATTGCAGCTT TGAATAATCA TTATCATTCC GTGCTCTCAT
 901 TGTGTTTGAA TTCATGCAAA ACACAAGAAA ACCAAGCGAG AAATTTTTTT CCAAACATGT
 961 TGTATTGTCA AAACGGTAAC ACTTTACAAT GAGGTTGATT AGTTCATGTA TTAACTAACA
1021 TTAAATAACC ATGAGCAATA CATTTGTTAC TGTATCTGTT AATCTTTGTT AACGTTAGTT
1081 AATAGAAATA CAGATGTTCA TTGTTTGTTC ATGTTAGTTC ACAGTGCATT AACTAATGTT
1141 AACAAGATAT AAAGTATTAG TAAATGTTGA AATTAACATG TATACGTGCA GTTCATTATT
1201 AGTTCATGTT AACTAATGTA GTTAACTAAC GAACCTTATT GTAAAAGTGT TACCATCAAA
1261 ACTAATGTAA TGAAATCAAT TCACCCTGTC ATGTCAGCCT TACAGTCCTG TGTTTTTGTC
1321 AATATAATCA GAAATAAAAT TAATGTTTGA TTGTCACTAA ATGCTACTGT ATTTCTAAAA
1381 TCAACAAGTA TTTAACATTA TAAAGTGTGC AATTGGCTGC AAATGTCAGT TTTATTAAAG
1441 GGTTAGTTCA CCCAAAAATG AAAATAATGT CATTAATGAC TCGCCCTCAT GTCGTTCCAA
1501 GCCCGTAAGA CCTCCGTTCA TCTTCAGAAC ACAGTTTAAG ATATTTAGA TTTAGTCCGA
1561 GAGCTTTCTG TGCCTCCATT GAGAATGTAT GTACGGTATA CTGTCCATGT CCAGAAAGGT
1621 AATAAAAACA TCAAAGTAGT CCATGTGACA TCAGTGGGTT AGTTAGAATT TTTTGAAGCA
1681 TCGAATACAT TTTGGTCCAA AAATAACAAA ACCTACGACT TTATTCGGCA TTGTATTCTC
1741 TTCCGGGTCT GTTGTCAATC CGCGTTCACG ACTTCGCAGT GACGCTACAA TGCTGAATAA
1801 AGTCGTAGGT TTTGTTATTT TTGGACCAAA ATGTATTTTC GATGCTTCAA ATAATTCTAC
1861 CTAACCCACT GATGTCACAT GGACTACTTT GATGTTTTTA TTACCTTTCT GGACATGGAC
1921 AGTATACCGT ACATACATTT TCAGTGGAGG GACAGAAAGC TCTCGGACTA AATCTAAAAT
1981 ATCTTAAACT GTGTTCCGAA GATGAACGGA GGTGTTACGG GCTTGGAACG ACATGAGGGT
2041 GAGTCATTAA TGACATCTTT TCATTTTTGG GTGAACTAAC CCTTTAATGC TGTAATCAGA
2101 GAGTGTATGT GTAATTGTTA CATTTATTGC ATACAATATA AATATTTATT TGTTGTTTTT
2161 ACAGAGAATG CACCCAAATT ACCTCAAAAA CTACTCTAAA TTGACAGCAC AGAAGAGAAA
```

-continued

```
2221 GATCGGGACC TCCACCCATG CTTCCAGCAG TAAGCAACTG AAAGTTGACT CAGTTTTCCC

2281 AGTCAAACAT GTGTCTCCAG TCACTGTGAA CAAAGCTATA TTAAGGTACA TCATTCAAGG

2341 ACTTCATCCT TTCAGCACTG TTGATCTGCC ATCATTTAAA GAGCTGATTA GTACACTGCA

2401 GCCTGGCATT TCTGTCATTA CAAGGCCTAC TTTACGCTCC AAGATAGCTG AAGCTGCTCT

2461 GATCATGAAA CAGAAAGTGA CTGCTGCCAT GAGTGAAGTT GAATGGATTG CAACCACAAC

2521 GGATTGTTGG ACTGCACGTA GAAAGTCATT CATTGGTGTA ACTGCTCACT GGATCAACCC

2581 TGGAAGTCTT GAAAGACATT CCGCTGCACT TGCCTGCAAA AGATTAATGG GCTCTCATAC

2641 TTTTGAGGTA CTGGCCAGTG CCATGAATGA TATCCACTCA GAGTATGAAA TACGTGACAA

2701 GGTTGTTTGC ACAACCACAG ACAGTGGTTC AACTTTATG AAGGCTTTCA GAGTTTTTGG

2761 TGTGGAAAAC AATGATATCG AGACTGAGGC AAGAAGGTGT GAAAGTGATG ACACTGATTC

2821 TGAAGGCTGT GGTGAGGGAA GTGATGGTGT GGAATTCCAA GATGCCTCAC GAGTCCTGGA

2881 CCAAGACGAT GGCTTCGAAT TCCAGCTACC AAAACATCAA AAGTGTGCCT GTCACTTACT

2941 TAACCTAGTC TCAAGCGTTG ATGCCCAAAA AGCTCTCTCA ATGAACACT ACAAGAAACT

3001 CTACAGATCT GTCTTTGGCA AATGCCAAGC TTTATGGAAT AAAAGCAGCC GATCGGCTCT

3061 AGCAGCTGAA GCTGTTGAAT CAGAAAGCCG GCTTCAGCTT TTAAGGCCAA ACCAAACGCG

3121 GTGGAATTCA ACTTTTATGG CTGTTGACAG AATTCTTCAA ATTTGCAAAG AAGCAGGAGA

3181 AGGCGCACTT CGGAATATAT GCACCTCTCT TGAGGTTCCA ATGTAAGTGT TTTTCCCCTC

3241 TATCGATGTA AACAAATGTG GGTTGTTTTT GTTTAATACT CTTTGATTAT GCTGATTTCT

3301 CCTGTAGGTT TAATCCAGCA GAAATGCTGT TCTTGACAGA GTGGGCCAAC ACAATGCGTC

3361 CAGTTGCAAA AGTACTCGAC ATCTTGCAAG CGGAAACGAA TACACAGCTG GGGTGGCTGC

3421 TGCCTAGTGT CCATCAGTTA AGCTTGAAAC TTCAGCGACT CCACCATTCT CTCAGGTACT

3481 GTGACCCACT TGTGGATGCC CTACAACAAG GAATCCAAAC ACGATTCAAG CATATGTTTG

3541 AAGATCCTGA GATCATAGCA GCTGCCATCC TTCTCCCTAA ATTTCGGACC TCTTGGACAA

3601 ATGATGAAAC CATCATAAAA CGAGGTAAAT GAATGCAAGC AACATACACT TGACGAATTC

3661 TAATCTGGGC AACCTTTGAG CCATACCAAA ATTATTCTTT TATTTATTTA TTTTTGCACT

3721 TTTTAGGAAT GTTATATCCC ATCTTTGGCT GTGATCTCAA TATGAATATT GATGTAAAGT

3781 ATTCTTGCAG CAGGTTGTAG TTATCCCTCA GTGTTTCTTG AAACCAAACT CATATGTATC

3841 ATATGTGGTT TGGAAATGCA GTTAGATTTT ATGCTAAAAT AAGGGATTTG CATGATTTTA

3901 GATGTAGATG ACTGCACGTA AATGTAGTTA ATGACAAAAT CCATAAAATT TGTTCCCAGT

3961 CAGAAGCCCC TCAACCAAAC TTTTCTTTGT GTCTGCTCAC TGTGCTTGTA GGCATGGACT

4021 ACATCAGAGT GCATCTGGAG CCTTTGGACC ACAAGAAGGA ATTGGCCAAC AGTTCATCTG

4081 ATGATGAAGA TTTTTTCGCT TCTTTGAAAC CGACAACACA TGAAGCCAGC AAAGAGTTGG

4141 ATGGATATCT GGCCTGTGTT TCAGACACCA GGGAGTCTCT GCTCACGTTT CCTGCTATTT

4201 GCAGCCTCTC TATCAAGACT AATACACCTC TTCCCGCATC GGCTGCCTGT GAGAGGCTTT

4261 TCAGCACTGC AGGATTGCTT TTCAGCCCCA AAAGAGCTAG GCTTGACACT AACAATTTTG

4321 AGAATCAGCT TCTACTGAAG TTAAATCTGA GGTTTTACAA CTTTGAGTAG CGTGTACTGG

4381 CATTAGATTG TCTGTCTTAT AGTTTGATAA TTAAATACAA ACAGTTCTAA AGCAGGATAA

4441 AACCTTGTAT GCATTTCATT TAATGTTTTT TGAGATTAAA AGCTTAAACA AGAATCTCTA
```

```
-continued
4501  GTTTTCTTTC TTGCTTTTAC TTTTACTTCC TTAATACTCA AGTACAATTT TAATGGAGTA

4561  CTTTTTTACT TTTACTCAAG TAAGATTCTA GCCAGATACT TTTACTTTTA ATTGAGTAAA

4621  ATTTTCCCTA AGTACTTGTA CTTTCACTTG AGTAAAATTT TTGAGTACTT TTTACACCTC

4681  TG.
```

The disclosure provides a vector comprising the inducible proapoptotic polypeptide, inducible caspase polypeptide, inducible caspase 9 polypeptide, and/or inducible truncated caspase 9 polypeptide of the disclosure. In certain embodiments, the vector is a viral vector.

Viral vectors of the disclosure may comprise a sequence isolated or derived from a retrovirus, a lentivirus, an adenovirus, an adeno-associated virus (AAV) or any combination thereof. In certain embodiments, the viral vector comprises a sequence isolated or derived from a retrovirus. In certain embodiments, the retrovirus is a gammaretrovirus. In certain embodiments, the retrovirus is a lentivirus. In certain embodiments, viral vectors of the disclosure may be recombinant vectors.

Viral vectors of the disclosure may comprise a sequence isolated or derived from an adeno-associated virus. In certain embodiments, the AAV comprises an AAV of a serotype AAV1, AAV2, AAV3, AAV4, AAV5, AAV6, AAV7, AAV8, AAV9, AAV10 or AAV11. In certain embodiments, the AAV comprises a sequence from one or more of AAV1, AAV2, AAV3, AAV4, AAV5, AAV6, AAV7, AAV8, AAV9, AAV10 or AAV11. In certain embodiments, the AAV comprises a sequence isolated, derived, or recombined from one or more of AAV1, AAV2, AAV3, AAV4, AAV5, AAV6, AAV7, AAV8, AAV9, AAV10 or AAV11. In certain embodiments, the AAV comprises a sequence isolated, derived, or recombined from AAV2. In certain embodiments, including those in which the vector crosses the blood brain barrier (BBB), the AAV comprises a sequence isolated, derived, or recombined from AAV9. Exemplary adeno-associated viruses and recombinant adeno-associated viruses of the disclosure include, but are not limited to, self-complementary AAV (scAAV) and AAV hybrids containing the genome of one serotype and the capsid of another serotype (e.g. AAV2/5, AAV-DJ and AAV-DJ8). Exemplary adeno-associated viruses and recombinant adeno-associated viruses of the disclosure include, but are not limited to, rAAV-LK03, rAAV-NP59 and rAAV-NP84. In certain embodiments, the AAV comprises a sequence isolated or derived from rAAV-LK03, rAAV-NP59 or rAAV-NP84. In certain embodiments, viral vectors of the disclosure may be recombinant vectors.

The disclosure provides a vector comprising the inducible proapoptotic polypeptide, inducible caspase polypeptide, inducible caspase 9 polypeptide, and/or inducible truncated caspase 9 polypeptide of the disclosure. In certain embodiments, the vector is a nanoparticle vector.

Nanoparticle vectors of the disclosure may comprise a nucleic acid, an amino acid, a polymer, a micelle, lipid, an organic molecule, an inorganic molecule or any combination thereof. Nanoparticles may be comprised of polymers disclosed in, for example, International Patent Publication No. WO 2012/094679, International Patent Publication No. WO 2016/022805, International Patent Publication No. WO/2011/133635, International Patent Publication No. WO/2016/090111, International Patent Publication No. WO/2017/004498, WO/2017/004509, International Patent Application No. PCT/US2017/030271, U.S. Pat. Nos. 6,835,394, 7,217,427, and 7,867,512.

Nanoparticle vectors of the disclosure may further comprise at least one self-cleaving peptide. In certain embodiments, a nanoparticle vector of the disclosure may comprise at least one self-cleaving peptide and wherein a self-cleaving peptide is located between the inducible proapoptotic polypeptide, inducible caspase polypeptide, inducible caspase 9 polypeptide, and/or inducible truncated caspase 9 polypeptide of the disclosure and another sequence linked to the nanoparticle. In certain embodiments, a nanoparticle vector of the disclosure may comprise at least one self-cleaving peptide and wherein a self-cleaving peptide is located upstream of the inducible proapoptotic polypeptide, inducible caspase polypeptide, inducible caspase 9 polypeptide, and/or inducible truncated caspase 9 polypeptide of the disclosure and a second self-cleaving peptide is located downstream of the inducible proapoptotic polypeptide, inducible caspase polypeptide, inducible caspase 9 polypeptide, and/or inducible truncated caspase 9 polypeptide of the disclosure. The at least one self-cleaving peptide may comprise a T2A peptide, GSG-T2A peptide, an E2A peptide, a GSG-E2A peptide, an F2A peptide, a GSG-F2A peptide, a P2A peptide, or a GSG-P2A peptide. In certain embodiments, the T2A peptide comprises an amino acid sequence comprising EGRGSLLTCGDVEENPGP (SEQ ID NO: 11). In certain embodiments, the GSG-T2A peptide comprises an amino acid sequence comprising GSGEGRGSLLTCGDVEENPGP (SEQ ID NO: 12). In certain embodiments, the E2A peptide comprises an amino acid sequence comprising QCTNYALLKLAGDVESNPGP (SEQ ID NO: 13). In certain embodiments, the GSG-E2A peptide comprises an amino acid sequence comprising GSGQCTNYALLKLAGDVESNPGP (SEQ ID NO: 14). In certain embodiments, the F2A peptide comprises an amino acid sequence comprising VKQTLNFDLLKLAGDVESNPGP (SEQ ID NO: 15). In certain embodiments, the GSG-F2A peptide comprises an amino acid sequence comprising GSGVKQTLNFDLLKLAGDVESNPGP (SEQ ID NO: 16). In certain embodiments, the P2A peptide comprises an amino acid sequence comprising ATNFSLLKQAGDVEENPGP (SEQ ID NO: 17). In certain embodiments, the GSG-P2A peptide comprises an amino acid sequence comprising GSGATNFSLLKQAGDVEENPGP (SEQ ID NO: 18).

The disclosure provides a composition comprising a vector of the disclosure.

The disclosure provides a cell comprising an inducible proapoptotic polypeptide, an inducible caspase polypeptide, an inducible caspase 9 polypeptide, and/or an inducible truncated caspase 9 polypeptide of the disclosure. The disclosure provides a cell comprising a transposon of the disclosure. The disclosure provides a cell comprising a vector of the disclosure. In certain embodiments, the cell expresses the inducible caspase protein of the disclosure following contact with an induction agent.

In certain embodiments, cells of the disclosure that comprise a polypeptide, transposon or vector of the disclosure may be human cells.

In certain embodiments, cells of the disclosure that comprise a polypeptide, transposon or vector of the disclosure may be immune cells. Examples of immune cells include, but are not limited to, T-cells, Natural Killer (NK) cells, Natural Killer (NK)-like cells, hematopoietic progenitor cells, peripheral blood (PB) derived T cells and umbilical cord blood (UCB) derived T-cells. In certain embodiments, cells of the disclosure that comprise a polypeptide, transposon or vector of the disclosure may be T-cells. In certain embodiments, cells of the disclosure that comprise a polypeptide, transposon or vector of the disclosure may be activated T-cells. In certain embodiments, cells of the disclosure that comprise a polypeptide, transposon or vector of the disclosure may be activated T-cells that express an iC9 sequence of the disclosure. In certain embodiments, cells of the disclosure that comprise a polypeptide, transposon or vector of the disclosure may be artificial antigen presenting cells (APCs). Immune cells of the disclosure may further include any commercially-available cell line or modified cell line, including, but not limited to, cell lines of dendritic cells, B cells, macrophages and monocytes.

In certain embodiments, cells of the disclosure that comprise a polypeptide, transposon or vector of the disclosure may be immune cells. Examples of immune cells include, but are not limited to, T-cells, Natural Killer (NK) cells, Natural Killer (NK)-like cells, hematopoietic progenitor cells, peripheral blood (PB) derived T cells and umbilical cord blood (UCB) derived T-cells. In certain embodiments, cells of the disclosure that comprise a polypeptide, transposon or vector of the disclosure may be T-cells. In certain embodiments, the cell is an artificial antigen presenting cell.

In certain embodiments, cells of the disclosure that comprise a polypeptide, transposon or vector of the disclosure may be stem cells. Stem cells of the disclosure may be human stem cells. Stem cells of the disclosure may be embryonic or adult stem cells. Stem cells of the disclosure may be totipotent, pluripotent, or multipotent. In certain embodiments, stem cells of the disclosure may be induced pluripotent stem cell (iPSC).

In certain embodiments, cells of the disclosure that comprise a polypeptide, transposon or vector of the disclosure may be somatic cells. Somatic cells of the disclosure may be isolated or derived from any part of a body, and preferably a human body, including, but not limited to, a human heart; skeletal or smooth muscle; blood vessel, vein or capillary; spleen; thyroid; lymph node or lymph vessel; bone or bone marrow; skin or endothelium; adrenal gland; esophagus; larynx; brain or spinal cord; peripheral nervous system; eye; hypothalamus; liver; olfactory tissue; prostate; stomach; large or small intestine; lung or bronchi; kidney; pancreas; thymus gland; ureter or urethrae; bladder; auditory tissue; bladder; parathyroid gland; salivary gland; or trachea. Somatic cells of the disclosure may be isolated or derived from a precursor or stem cell that may differentiate into any part of a body, and preferably a human body including, but not limited to, a human heart; skeletal or smooth muscle; blood vessel, vein or capillary; spleen; thyroid; lymph node or lymph vessel; bone or bone marrow; skin or endothelium; adrenal gland; esophagus; larynx; brain or spinal cord; peripheral nervous system; eye; hypothalamus; liver; olfactory tissue; prostate; stomach; large or small intestine; lung or bronchi; kidney; pancreas; thymus gland; ureter or urethrae; bladder; auditory tissue; bladder; parathyroid gland; salivary gland; or trachea. Somatic cells of the disclosure may be isolated or derived from transdifferentiated cells.

The disclosure provides a composition comprising a cell of the disclosure comprising a polypeptide, transposon, or vector of the disclosure.

The disclosure provides a use of the compositions of the disclosure for an adoptive cell therapy. In certain embodiments, the cells of the composition may be autologous. In certain embodiments, the cells of the composition may be allogeneic.

The disclosure provides a use of the compositions of the disclosure for an ex vivo gene therapy. In certain embodiments, the cells of the composition may be autologous. In certain embodiments, the cells of the composition may be allogeneic.

The disclosure provides a use for the composition comprising a cell of the disclosure for an ex vivo gene therapy. In certain embodiments of the use of the composition comprising the cells of the disclosure, the cell is autologous. In certain embodiments, the cell is allogenic.

The disclosure provides a method of modifying a cell therapy in a subject in need thereof, comprising administering to the subject a composition comprising a cell comprising a therapeutic agent and an inducible caspase polypeptide of the disclosure, wherein apoptosis may be selectively induced in the cell by contacting the cell with an induction agent.

The disclosure provides a method of modifying a cell therapy in a subject in need thereof, comprising administering to the subject a composition comprising a cell comprising a therapeutic agent and a composition of the disclosure, wherein apoptosis may be selectively induced in the cell by contacting the cell with an induction agent.

The disclosure provides a method of modifying a cell therapy in a subject in need thereof, comprising administering to the subject a composition comprising a cell comprising a therapeutic agent, a transposon of the disclosure and a composition comprising a transposase of the disclosure, wherein apoptosis may be selectively induced in the cell by contacting the cell with an induction agent.

The disclosure provides a method of modifying a cell therapy in a subject in need thereof, comprising administering to the subject a composition comprising a cell comprising a therapeutic agent and a vector of the disclosure, wherein apoptosis may be selectively induced in the cell by contacting the cell with an induction agent.

In certain embodiments of the methods of modifying a cell therapy of the disclosure, the cells of the composition may be autologous. In certain embodiments, the cells of the composition may be allogeneic. In certain embodiments of this method, the cell therapy is an adoptive cell therapy. In certain embodiments, the therapeutic agent has been introduced by ex vivo gene therapy. In certain embodiments, the therapeutic agent is a sequence encoding a modified endogenous gene, an exogenous gene, or a portion thereof. In certain embodiments of this method, the modifying of the cell therapy is a termination of the cell therapy. In certain embodiments of this method, the modifying of the cell therapy is a depletion of a portion of the cells provided in the cell therapy. This depletion may be transient or may be maintained for a period of time, for example, during a period of remission of a disease or disorder. In certain embodiments, the method further comprises the step of administering an inhibitor of the induction agent to inhibit modification of the cell therapy, thereby restoring the function and/or efficacy of the cell therapy. For example, should a disease or disorder return following a remission or a subject's adverse reaction subside, the cell therapy may be resumed by administering to the subject an inhibitor of the induction agent.

Methods of modifying a cell therapy of the disclosure may be used to terminate or dampen a therapy in response to, for example, a sign of recovery or a sign of decreasing disease severity/progression, a sign of disease remission/cessation, and/or the occurrence of an adverse event. Cell therapies of the disclosure may be resumed by inhibiting the induction agent should a sign or symptom of the disease reappear or increase in severity and/or an adverse event is resolved.

In certain embodiments, a composition comprising a cell of the disclosure or a modified cell of the disclosure is administered to a patient via injection or intravenous infusion. In certain embodiments, a therapeutically effective dose of a composition of the disclosure or of compositions comprising modified cells of the disclosure comprises between $2 \times 10^5$ and $5 \times 10^8$ cells per kg of body weight of the patient per administration, or any range, value or fraction thereof.

In certain embodiments, a composition comprising a cell of the disclosure or a modified cell of the disclosure is administered to a patient via injection or intravenous infusion. In certain embodiments, a therapeutically effective dose of a composition of the disclosure or of compositions comprising modified cells of the disclosure comprises between $0.2 \times 10^6$ to $20 \times 10^6$ cells per kg of body weight of the patient per administration. In certain embodiments, a therapeutically effective dose of a composition of the disclosure or of compositions comprising modified cells of the disclosure comprises $0.2 \times 10^6$ cells per kg of body weight of the patient per administration, $2 \times 10^6$ cells per kg of body weight of the patient per administration, $20 \times 10^6$ cells per kg of body weight of the patient per administration, or any cells per kg of body weight of the patient per administration in between.

In certain embodiments, a composition comprising a cell of the disclosure or a modified cell of the disclosure is administered to a patient via injection or intravenous infusion. In certain embodiments, a therapeutically effective dose of a composition of the disclosure or of compositions comprising modified cells of the disclosure comprises $1 \times 10^6$ cells or about $1 \times 10^6$ cells per kg of body weight of the patient per administration.

In certain embodiments, a composition comprising a cell of the disclosure or a modified cell of the disclosure is administered to a patient via injection or intravenous infusion. In certain embodiments, a therapeutically effective dose of a composition of the disclosure or of compositions comprising modified cells of the disclosure comprises $3 \times 10^6$ cells or about $3 \times 10^6$ cells per kg of body weight of the patient per administration.

In certain embodiments, a composition comprising a cell of the disclosure or a modified cell of the disclosure is administered to a patient via injection or intravenous infusion. In certain embodiments, a therapeutically effective dose of a composition of the disclosure or of compositions comprising modified cells of the disclosure comprises between $0.7 \times 10^6$ to $6.7 \times 10^6$ cells per kg of body weight of the patient per administration. In certain embodiments, a therapeutically effective dose of a composition of the disclosure or of compositions comprising modified cells of the disclosure comprises $0.7 \times 10^6$ cells per kg of body weight of the patient per administration, $6.7 \times 10^6$ cells per kg of body weight of the patient per administration or any cells per kg of body weight of the patient per administration in between.

In certain embodiments, a composition comprising a cell of the disclosure or a modified cell of the disclosure is administered to a patient via injection or intravenous infusion. In certain embodiments, a therapeutically effective dose of a composition of the disclosure or of compositions comprising modified cells of the disclosure comprises between $0.7 \times 10^6$ to $16 \times 10^6$ cells per kg of body weight of the patient per administration. In certain embodiments, a therapeutically effective dose of a composition of the disclosure or of compositions comprising modified cells of the disclosure comprises $0.7 \times 10^6$ cells per kg of body weight of the patient per administration, $2 \times 10^6$ cells per kg of body weight of the patient per administration, $6 \times 10^6$ cells per kg of body weight of the patient per administration, $10.7 \times 10^6$ cells per kg of body weight of the patient per administration, $16 \times 10^6$ cells per kg of body weight of the patient per administration or any cells per kg of body weight of the patient per administration in between.

In certain embodiments, a composition comprising a cell of the disclosure or a modified cell of the disclosure is administered to a patient via injection or intravenous infusion. In certain embodiments, a therapeutically effective dose of a composition of the disclosure or of compositions comprising modified cells of the disclosure comprises $1.2 \times 10^6$ to $7.1 \times 10^6$ cells per kg of body weight of the patient per administration. In certain embodiments, a therapeutically effective dose of a composition of the disclosure or of compositions comprising modified cells of the disclosure comprises $1.2 \times 10^6$ cells per kg of body weight of the patient per administration, $7.1 \times 10^6$ cells per kg of body weight of the patient per administration or any number of cells per kg of body weight of the patient per administration. In certain embodiments, a therapeutically effective dose of a composition of the disclosure or of compositions comprising modified cells of the disclosure comprises between $2 \times 10^6$ to $3 \times 10^6$ cells per kg of body weight of the patient per administration.

In certain embodiments, a composition comprising a cell of the disclosure or a modified cell of the disclosure is administered to a patient via injection or intravenous infusion. In certain embodiments, a therapeutically effective dose of a composition of the disclosure or of compositions comprising modified cells of the disclosure comprises $1 \times 10^6$ to $2 \times 10^6$ cells per kg of body weight of the patient per administration. In certain embodiments, a therapeutically effective dose of a composition of the disclosure or of compositions comprising modified cells of the disclosure comprises $1 \times 10^6$ cells per kg of body weight of the patient per administration, $2 \times 10^6$ cells per kg of body weight of the patient per administration or any number of cells per kg of body weight of the patient per administration in between. In certain embodiments of the disclosure, modified cells of the disclosure are delivered to a patient via injection or intravenous infusion. In certain embodiments, a therapeutically effective dose of a composition of the disclosure or of compositions comprising modified cells of the disclosure comprises $0.7 \times 10^6$ to $1.3 \times 10^6$ cells per kg of body weight of the patient per administration. In certain embodiments, a therapeutically effective dose of a composition of the disclosure or of compositions comprising modified cells of the disclosure comprises $0.7 \times 10^6$ cells per kg of body weight of the patient per administration, $1.3 \times 10^6$ cells per kg of body weight of the patient per administration or any number of cells per kg of body weight of the patient per administration in between.

In certain embodiments, a composition comprising a cell of the disclosure or a modified cell of the disclosure is administered to a patient via injection or intravenous infusion. In certain embodiments, a therapeutically effective dose of a composition of the disclosure or of compositions comprising modified cells of the disclosure comprises a single or multiple doses. In certain embodiments, a therapeutically effective dose of a composition of the disclosure or of compositions comprising modified cells of the disclosure comprises a split dose. In certain embodiments, a therapeutically effective dose of a composition of the disclosure or of compositions comprising modified cells of the disclosure comprises an initial dose and a maintenance dose.

The disclosure provides a method of treating a disease or disorder in a subject in need thereof comprising administering to the subject a composition comprising a cell comprising a kinetic agent and an inducible caspase polypeptide of the disclosure, wherein apoptosis may be selectively induced in the cell by contacting the cell with an induction agent, and wherein the cell comprising the kinetic agent induces local tissue toxicity within a target tissue of the subject, and selectively inducing apoptosis in the cell comprising the kinetic agent prior to induction of toxicity in a non-target tissue of the subject, thereby treating eliminating the target tissue, preserving non-target tissue and treating the disease or disorder in the subject.

As used herein, a kinetic agent is meant to describe a therapeutic agent having specificity for a target tissue and either known/intentional or unknown/unintentional toxicity towards non-target tissue, which, in either case, may be controlled or limited such that the toxicity does not significantly affect non-target tissues. Kinetic agents specifically target a tissue, specifically and locally induce toxicity, but before a kinetic agent can induce significant toxicity or damage to a non-target tissue, an induction agent of the disclosure may be administered to reduce or prevent non-target tissue toxicity. The extent to which any toxicity affects off-target tissues (e.g. damage to non-target tissues) may be limited by the administration of the induction agent and may correspond to a duration of exposure of the non-target tissue to the kinetic agent. In certain embodiments of the disclosure, cells comprising a therapeutic agent may react to both on-target on-tumor cells and on-target off-tumor cells at the same time and in multiple different tissues. The on-target off-tumor cells are preserved through the activation of the inducible caspase polypeptides of the disclosure in the cells comprising a therapeutic agent to eliminate the cells comprising the inducible caspase polypeptides of the disclosure, for example, after the tumor is eliminated. In certain embodiments, off-tumor off-target effects may be due to cross-reactivity of the kinetic agent. In certain embodiments, if the off-target effects are too great, the toxicity off the kinetic agent may be limited or eliminated by administration of an induction agent before the treatment of a disease of the subject is complete.

The disclosure provides a method of treating a disease or disorder in a subject in need thereof comprising administering to the subject a composition comprising a cell comprising a kinetic agent and a composition of the disclosure, wherein apoptosis may be selectively induced in the cell by contacting the cell with an induction agent, and wherein the cell comprising the kinetic agent induces local tissue toxicity within a target tissue of the subject, and selectively inducing apoptosis in the cell comprising the kinetic agent prior to induction of significant toxicity in a non-target tissue of the subject, thereby treating eliminating the target tissue, preserving non-target tissue and treating the disease or disorder in the subject.

The disclosure provides a method of treating a disease or disorder in a subject in need thereof comprising administering to the subject a composition comprising a cell comprising a kinetic agent, a transposon of the disclosure and a composition comprising a transposase of the disclosure, wherein apoptosis may be selectively induced in the cell by contacting the cell with an induction agent, and wherein the cell comprising the kinetic agent induces local tissue toxicity within a target tissue of the subject, and selectively inducing apoptosis in the cell comprising the kinetic agent prior to induction of significant toxicity in a non-target tissue of the subject, thereby treating eliminating the target tissue, preserving non-target tissue and treating the disease or disorder in the subject.

The disclosure provides a method of treating a disease or disorder in a subject in need thereof comprising administering to the subject a composition comprising a cell comprising a kinetic agent and a vector of the disclosure, wherein apoptosis may be selectively induced in the cell by contacting the cell with an induction agent, and wherein the cell comprising the kinetic agent induces local tissue toxicity within a target tissue of the subject, and selectively inducing apoptosis in the cell comprising the kinetic agent prior to induction of significant toxicity in a non-target tissue of the subject, thereby treating eliminating the target tissue, preserving non-target tissue and treating the disease or disorder in the subject.

The term "significant toxicity in a non-target tissue" may described a level of toxicity in which the cells of the tissue are dead (e.g. have died as a result of necrosis or apoptosis), have otherwise become not viable or have ceased to perform one or more essential physiological function(s). In certain embodiments, significant toxicity denotes permanent damage to a cell or a tissue. In certain embodiments, significant toxicity denotes a transient loss of a function of a cell or a tissue. In certain embodiments, significant toxicity induces symptoms in a subject that are recognizable as such by one skilled in the art. In certain embodiments, significant toxicity leads to death, a reduced life span, or a reduced quality of life of a subject.

In certain embodiments of the methods of treating a disease or disorder of the disclosure, the disease or disorder is a proliferative disorder or cancer. In certain embodiments, the target tissue comprises a tumor. In certain embodiments, the tumor is benign. In certain embodiments, the tumor is malignant. In certain embodiments, the target tissue comprises an exposed tissue or margin of a resected tumor. In certain embodiments, the target tissue comprises a site of probable metastasis. In certain embodiments, the site of metastasis comprise one or more of a lymph node, lymph fluid, peripheral circulating blood, local circulating blood, a bone, a bone marrow and cerebral spinal fluid (CSF).

In certain embodiments of the methods of treating a disease or disorder of the disclosure, the disease or disorder is an inflammatory disease or disorder. In certain embodiments, the target tissue comprises a site of inflammation.

In certain embodiments of the methods of treating a disease or disorder of the disclosure, the disease or disorder is an immune or autoimmune disease or disorder. In certain embodiments, the target tissue comprises a site of exposed or infected tissue. In certain embodiments, the target tissue comprises a burned or a wounded tissue.

In certain embodiments of the methods of treating a disease or disorder of the disclosure, the disease or disorder is an infectious disease or disorder. In certain embodiments, the target tissue comprises an infected tissue.

In certain embodiments of the methods of treating a disease or disorder of the disclosure, the disease or disorder is a genetic or epigenetic disease or disorder. In certain embodiments, the target tissue comprises one or more cells comprising the genetic or epigenetic modification when compared to a wild type cell.

In certain embodiments of the methods of treating a disease or disorder of the disclosure, the disease or disorder is a metabolic disorder. In certain embodiments, the target tissue comprises one or more cells with the metabolic disorder.

In certain embodiments of the methods of treating a disease or disorder of the disclosure, the disease or disorder is a vascular disorder. In certain embodiments, the target tissue comprises one or more cells of a vein, blood vessel, capillary or a component of circulating blood.

In certain embodiments of the methods of treating a disease or disorder of the disclosure, the disease or disorder is a respiratory disorder. In certain embodiments, the target tissue comprises one or more cells of a nasal passage, esophagus, or lung.

In certain embodiments of the methods of treating a disease or disorder of the disclosure, the disease or disorder is a fibrotic disorder. In certain embodiments, the target tissue comprises a fibroid mass or a cell in proximity to the fibroid mass.

In certain embodiments of the methods of treating a disease or disorder of the disclosure, an adoptive cell therapy comprises the cell comprising the kinetic agent. In certain embodiments, the cell comprising the kinetic agent is autologous. In certain embodiments, the cell comprising the kinetic agent is allogeneic. In certain embodiments, the cell comprising the kinetic agent is a T-cell. In certain embodiments, the kinetic agent is a non-naturally occurring receptor. In certain embodiments, the non-naturally occurring receptor is a synthetic, modified, recombinant or chimeric receptor. In certain embodiments, the chimeric receptor is a chimeric antigen receptor (CAR).

In certain embodiments of the methods of treating a disease or disorder of the disclosure, the disease or disorder is a proliferative disorder or a cancer. In certain embodiments, the target tissue comprises a tumor. In certain embodiments, treatment of the tumor comprises a composition comprising a cell comprising an inducible caspase polypeptide of the disclosure. In certain embodiments, the composition comprising a cell comprising an inducible caspase polypeptide of the disclosure further comprises a chimeric antigen receptor (CAR). In certain embodiments, the chimeric antigen receptor (CAR) specifically binds a sequence expressed on a cell of a tumor, thereby conferring specificity of the CAR for the tumor cell. In certain embodiments, the cell expressing the CAR that specifically binds a tumor cell is a T-cell, thereby making a CAR-T that specifically binds a tumor cell. In certain embodiments, compositions comprising CAR-T cells specifically target tumor cells will selectively kill only those tumor cells expressing the antigen sequence. However, in certain embodiments, the tumor antigen may be expressed in other normal tissues leading to on-target off-tumor activity of the CAR-T cells in non-target tissues. For example, the antigen may be CD19 and CD19 is expressed almost exclusively in B cells. In the case of CD19, off target activity of anti-CD19 CAR-T cells is minimal. However, if, for example, the antigen is PSMA (folate hydrolase 1) and PSMA is expressed in several normal cell types, anti-PSMA CAR-T cells may target normal cells in addition to the pathological target cells in an activity called on-target off-tumor toxicity. In certain embodiments, once the pathological target cells of the disclosure (for example, the tumor cells) are eradicated by the anti-PSMA CAR-T cells, treating the subject with the induction agent of the disclosure to induce programmed cell death in the anti-PSMA CAR-T cells using the inducible caspase polypeptides of the disclosure eliminates on-target off-tumor effects.

In certain methods of the disclosure, including those wherein an adoptive cell therapy comprises the cell comprising the kinetic agent, the kinetic agent comprises an anti-cancer agent. In certain embodiments, the anti-cancer agent comprises an anti-CD19 agent. In certain embodiments, the anti-cancer agent comprises an anti-BCMA agent. In certain embodiments, the anti-cancer agent comprises an anti-PSMA agent. In certain embodiments, the anti-cancer agent comprises an anti-Muc1 agent. In certain embodiments, the kinetic agent comprises a non-naturally occurring receptor. In certain embodiments, the non-naturally occurring receptor comprises a synthetic, modified, recombinant or chimeric receptor. In certain embodiments, the chimeric receptor is a chimeric antigen receptor (CAR). In certain embodiments, the CAR comprises one or more VHH sequence(s). In certain embodiments, the CAR is a VCAR. In certain embodiments, the kinetic agent induces an aplasia. In certain embodiments, the aplasia is not fatal. In certain embodiments, the induction agent eliminates the cell comprising the kinetic agent. In certain embodiments, the cell is a T-cell. In certain embodiments, the induction agent eliminates or reduces a sign or a symptom of the aplasia. In certain embodiments, the CAR-T therapy eliminates the malignancy, but continues to target healthy B cells such that the subject must be treated with IVIG infusions. In certain embodiments, anti-BCMA CAR-T therapy eliminates the subject's own unmutated plasma cells such that the subject must also be treated with IVIG. In certain embodiments, the CAR-T causing the aplasia may be eliminated through the caspase 9 polypeptides of the disclosure and the induction agent. In certain embodiments, treatment of the subject with the induction agent of the disclosure alleviates a sign or a symptom of the aplasia.

BRIEF DESCRIPTION OF THE DRAWINGS

FIG. 6 shows the presence of CARTyrin cells in blood, spleen, and bone marrow following AP1903 Treatment. Blood, spleen, and bone marrow cells were analyzed by flow cytometry for the presence of huCD45$^+$ cells. The relative viability was determined by: ((# of huCD45 cells/# of msCD45 cells)/(Average of huCD45/msCD45 in no treatment group))*100% per 1,500 bead events for each sample. Each data point represents a different mouse. On the x-axis is plotted percent Relative CAR-T Viability from 0 to 175 in increments of 25. On the y axis, from left to right for each panel, blood, spleen and bone marrow following AP1903 (Rimiducid) treatment. AP1903 (Rimiducid) increase by panel from left to right in the following order: 0 mg/kg, 0.005 mg/kg, 0.05 mg/kg, 0.5 mg·kg, 5 mg/kg and 5 mg/kg in the absence of the iC9 gene.

DETAILED DESCRIPTION

Figure 1:
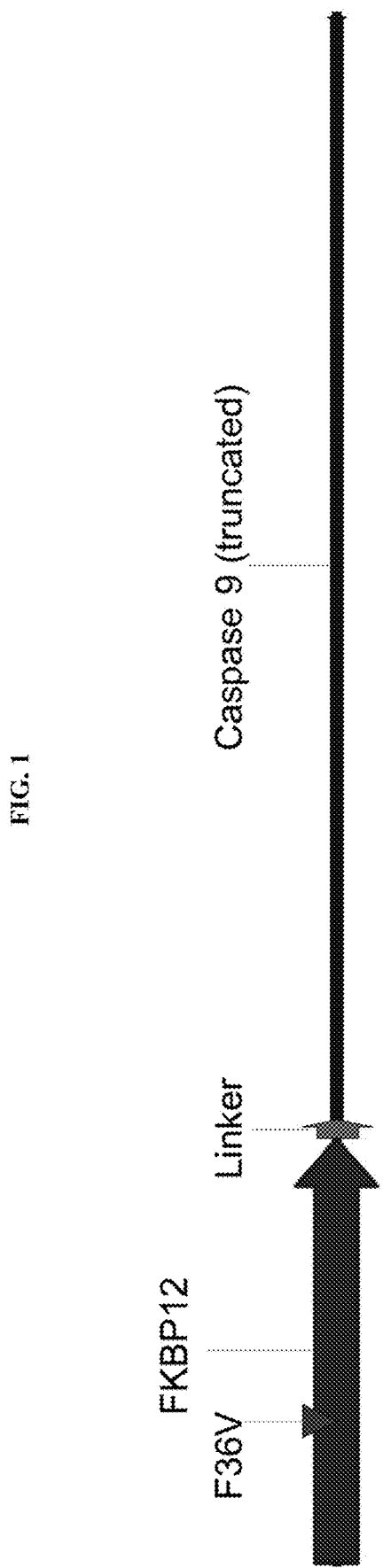
FIG. 1 is a schematic diagram depicting an exemplary inducible truncated caspase 9 polypeptide of the disclosure.

The disclosure provides inducible proapoptotic polypeptides as well as transposons, vectors, and cells comprising inducible proapoptotic polypeptides of the disclosure. Inducible proapoptotic polypeptides of the disclosure may be introduced into a cell simultaneously or sequentially with a therapeutic agent. For example, inducible proapoptotic polypeptides of the disclosure may be introduced into a cell simultaneously or sequentially with one or more sequences that encode a chimeric antigen receptor to produce a modified cell of the disclosure. Modified cells of the disclosure may be used in cell-based therapies. To control activity of modified cells of the disclosure comprising an inducible proapoptotic polypeptide, and, optionally, a therapeutic agent, the cell and/or the inducible proapoptotic polypeptide may contact an induction agent that specifically binds to the ligand binding region of the inducible proapoptotic polypeptide and ultimately causes initiation of apoptosis in the cell comprising the inducible proapoptotic polypeptide. When a modified cell of the disclosure is used as a cell therapy, the induction agent may be administered locally or systemically to the subject who received the cell therapy. An inhibitor of the induction agent may be administered locally or systemically to the subject who received the cell therapy and the induction agent.

As used herein, the term "therapeutic agent" may refer to any molecule, organic or inorganic, that, when introduced into a cell intended for cell therapy, modified an activity, a signaling pathway, a signaling outcome, and/or an interaction of that cell with the cell's internal or external environment, including, but not limited to, neighboring cells, extracellular ligands and signaling molecules, immune system of the cell's host or a component thereof, infection of host, a diseased cell (e.g. a cancer cell) of the host, intracellular ligands and signaling molecules, epigenetic regulation, gene transcription, gene regulation, transcriptome, DNA/RNA translation, protein processing or secretion processes, and proteome. Therapeutic agents include, but are not limited to, recombinant and/or chimeric cell surface receptors, recombinant and/or chimeric transmembrane receptors, recombinant and/or chimeric ion channels, and recombinant and/or chimeric antigen receptors. In certain embodiments, the therapeutic agent is a chimeric antigen receptor (CAR), and, optionally, a chimeric antigen receptor in which the antigen recognition region comprises at least one Centyrin. As used throughout the disclosure, a CAR comprising a Centyrin is referred to as a CARTyrin.

The disclosure provides inducible proapoptotic polypeptides comprising a ligand binding region, a linker, and a proapoptotic peptide, wherein the inducible proapoptotic polypeptide does not comprise a non-human sequence. In certain embodiments, the non-human sequence comprises a restriction site. Inducible proapoptotic polypeptides of the disclosure dimerize through interaction with an induction agent. Dimerization of a first inducible proapoptotic polypeptide and a second inducible proapoptotic polypeptide facilitates or activates an interaction, a cross-linking, a cross-activation, or an activation of the caspase polypeptides. The interaction, cross-linking, cross-activation, or activation of the caspase polypeptides initiates apoptosis in a cell comprising the inducible proapoptotic polypeptides of the disclosure or a sequence encoding the inducible proapoptotic polypeptides of the disclosure. Inducible proapoptotic polypeptides of the disclosure do not initiate apoptosis unless and the inducible proapoptotic polypeptide of the disclosure contacts an induction agent. Contact between an induction agent and an inducible proapoptotic polypeptides of the disclosure may occur in vivo, ex vivo, or in vitro. Contact between an induction agent and an inducible proapoptotic polypeptides of the disclosure may occur intracellularly.

With respect to cell therapies, the disclosure provides modified T cells for adoptive cell therapies comprising an inducible proapoptotic polypeptide or a sequence encoding an inducible proapoptotic polypeptide of the disclosure.

Modified T cells for adoptive cell therapies may be autologous or allogeneic. The term "allogeneic" as used herein, refers to HLA or MEW loci that are antigenically distinct. Cells or tissue transferred from the same species can be antigenically distinct. Syngeneic mice can differ at one or more loci (congenics) and allogeneic mice can have the same background.

Modified T cells for adoptive cell therapies may include activated T cells. T cells (also referred to as T lymphocytes) belong to a group of white blood cells referred to as lymphocytes. Lymphocytes generally are involved in cell-mediated immunity. The "T" in "T cells" refers to cells derived from or whose maturation is influence by the thymus. T cells can be distinguished from other lymphocytes types such as B cells and Natural Killer (NK) cells by the presence of cell surface proteins known as T cell receptors. The term "activated T cells" as used herein, refers to T cells that have been stimulated to produce an immune response (e.g., clonal expansion of activated T cells) by recognition of an antigenic determinant presented in the context of a Class II major histocompatibility (MHC) marker. T-cells are activated by the presence of an antigenic determinant, cytokines and/or lymphokines and cluster of differentiation cell surface proteins (e.g., CD3, CD4, CD8, the like and combinations thereof). Cells that express a cluster of differential protein often are said to be "positive" for expression of that protein on the surface of T-cells (e.g., cells positive for CD3 or CD4 expression are referred to as CD3+ or CD4+). CD3 and CD4 proteins are cell surface receptors or co-receptors that may be directly and/or indirectly involved in signal transduction in T cells.

Modified T cells for adoptive cell therapies may include "pan T cells". As used herein, pan T-cells include all T lymphocytes isolated from a biological sample, without sorting by subtype, activation status, maturation state, or cell-surface marker expression.

Modified T cells for adoptive cell therapies may be obtained and/or prepared from, for example, whole blood, peripheral blood, umbilical cord blood, lymph fluid, lymph node tissue, bone marrow, and cerebral spinal fluid (CSF). By "obtained or prepared" as, for example, in the case of cells, is meant that the cells or cell culture are isolated, purified, or partially purified from the source, where the source may be, for example, umbilical cord blood, bone marrow, or peripheral blood. The terms may also apply to the case where the original source, or a cell culture, has been cultured and the cells have replicated, and where the progeny cells are now derived from the original source. The term "peripheral blood" as used herein, refers to cellular components of blood (e.g., red blood cells, white blood cells and platelets), which are obtained or prepared from the circulating pool of blood and not sequestered within the lymphatic system, spleen, liver or bone marrow. Umbilical cord blood is distinct from peripheral blood and blood sequestered within the lymphatic system, spleen, liver or bone marrow. The terms "umbilical cord blood", "umbilical blood" or "cord blood", which can be used interchangeably, refers to blood that remains in the placenta and in the attached umbilical cord after child birth. Cord blood often contains stem cells including hematopoietic cells.

The disclosure provides inducible proapoptotic polypeptides comprising a ligand binding region, a linker, and a proapoptotic peptide, wherein the inducible proapoptotic polypeptide does not comprise a non-human sequence. In certain embodiments, the non-human sequence comprises a restriction site. In certain embodiments, the proapoptotic peptide is a caspase polypeptide. In certain embodiments, the caspase polypeptide is a caspase 9 polypeptide. In certain embodiments, the caspase 9 polypeptide is a truncated caspase 9 polypeptide. Inducible proapoptotic polypeptides of the disclosure may be non-naturally occurring.

Caspase polypeptides of the disclosure include, but are not limited to, caspase 1, caspase 2, caspase 3, caspase 4, caspase 5, caspase 6, caspase 7, caspase 8, caspase 9, caspase 10, caspase 11, caspase 12, and caspase 14. Caspase polypeptides of the disclosure include, but are not limited to, those caspase polypeptides associated with apoptosis including caspase 2, caspase 3, caspase 6, caspase 7, caspase 8, caspase 9, and caspase 10. Caspase polypeptides of the disclosure include, but are not limited to, those caspase polypeptides that initiate apoptosis, including caspase 2, caspase 8, caspase 9, and caspase 10. Caspase polypeptides of the disclosure include, but are not limited to, those caspase polypeptides that execute apoptosis, including caspase 3, caspase 6, and caspase 7.

Caspase polypeptides of the disclosure may be encoded by an amino acid or a nucleic acid sequence having one or more modifications compared to a wild type amino acid or a nucleic acid sequence. The nucleic acid sequence encoding a caspase polypeptide of the disclosure may be codon optimized. The one or more modifications to an amino acid and/or nucleic acid sequence of a caspase polypeptide of the disclosure may increase an interaction, a cross-linking, a cross-activation, or an activation of the caspase polypeptide of the disclosure compared to a wild type amino acid or a nucleic acid sequence. Alternatively, or in addition, the one or more modifications to an amino acid and/or nucleic acid sequence of a caspase polypeptide of the disclosure may decrease the immunogenicity of the caspase polypeptide of the disclosure compared to a wild type amino acid or a nucleic acid sequence.

Caspase polypeptides of the disclosure may be truncated compared to a wild type caspase polypeptide. For example, a caspase polypeptide may be truncated to eliminate a sequence encoding a Caspase Activation and Recruitment Domain (CARD) to eliminate or minimize the possibility of activating a local inflammatory response in addition to initiating apoptosis in the cell comprising an inducible caspase polypeptide of the disclosure. The nucleic acid sequence encoding a caspase polypeptide of the disclosure may be spliced to form a variant amino acid sequence of the caspase polypeptide of the disclosure compared to a wild type caspase polypeptide. Caspase polypeptides of the disclosure may be encoded by recombinant and/or chimeric sequences. Recombinant and/or chimeric caspase polypeptides of the disclosure may include sequences from one or more different caspase polypeptides. Alternatively, or in addition, recombinant and/or chimeric caspase polypeptides of the disclosure may include sequences from one or more species (e.g. a human sequence and a non-human sequence). Caspase polypeptides of the disclosure may be non-naturally occurring.

The ligand binding region of an inducible proapoptotic polypeptide of the disclosure may include any polypeptide sequence that facilitates or promotes the dimerization of a first inducible proapoptotic polypeptide of the disclosure with a second inducible proapoptotic polypeptide of the disclosure, the dimerization of which activates or induces cross-linking of the proapoptotic polypeptides and initiation of apoptosis in the cell.

The ligand-binding ("dimerization") region may comprise any polypeptide or functional domain thereof that will allow for induction using a natural or unnatural ligand (i.e. and induction agent), for example, an unnatural synthetic ligand. The ligand-binding region may be internal or external to the cellular membrane, depending upon the nature of the inducible proapoptotic polypeptide and the choice of ligand (i.e. induction agent). A wide variety of ligand-binding polypeptides and functional domains thereof, including receptors, are known. Ligand-binding regions of the disclosure may include one or more sequences from a receptor. Of particular interest are ligand-binding regions for which ligands (for example, small organic ligands) are known or may be readily produced. These ligand-binding regions or receptors may include, but are not limited to, the FKBPs and cyclophilin receptors, the steroid receptors, the tetracycline receptor, and the like, as well as "unnatural" receptors, which can be obtained from antibodies, particularly the heavy or light chain subunit, mutated sequences thereof, random amino acid sequences obtained by stochastic procedures, combinatorial syntheses, and the like. In certain embodiments, the ligand-binding region is selected from the group consisting of a FKBP ligand-binding region, a cyclophilin receptor ligand-binding region, a steroid receptor ligand-binding region, a cyclophilin receptors ligand-binding region, and a tetracycline receptor ligand-binding region.

The ligand-binding regions comprising one or more receptor domain(s) may be at least about 50 amino acids, and fewer than about 350 amino acids, usually fewer than 200 amino acids, either as the natural domain or truncated active portion thereof. The binding region may, for example, be small (<25 kDa, to allow efficient transfection in viral vectors), monomeric, nonimmunogenic, have synthetically accessible, cell permeable, nontoxic ligands that can be configured for dimerization.

The ligand-binding regions comprising one or more receptor domain(s) may be intracellular or extracellular depending upon the design of the inducible proapoptotic polypeptide and the availability of an appropriate ligand (i.e. induction agent). For hydrophobic ligands, the binding region can be on either side of the membrane, but for hydrophilic ligands, particularly protein ligands, the binding region will usually be external to the cell membrane, unless there is a transport system for internalizing the ligand in a form in which it is available for binding. For an intracellular receptor, the inducible proapoptotic polypeptide or a transposon or vector comprising the inducible proapoptotic polypeptide may encode a signal peptide and transmembrane domain 5' or 3' of the receptor domain sequence or may have a lipid attachment signal sequence 5' of the receptor domain sequence. Where the receptor domain is between the signal peptide and the transmembrane domain, the receptor domain will be extracellular.

Antibodies and antibody subunits, e.g., heavy or light chain, particularly fragments, more particularly all or part of the variable region, or fusions of heavy and light chain to create high-affinity binding, can be used as a ligand binding region of the disclosure. Antibodies that are contemplated include ones that are an ectopically expressed human product, such as an extracellular domain that would not trigger an immune response and generally not expressed in the periphery (i.e., outside the CNS/brain area). Such examples, include, but are not limited to low affinity nerve growth factor receptor (LNGFR), and embryonic surface proteins (i.e., carcinoembryonic antigen). Yet further, antibodies can be prepared against haptenic molecules, which are physiologically acceptable, and the individual antibody subunits screened for binding affinity. The cDNA encoding the subunits can be isolated and modified by deletion of the constant region, portions of the variable region, mutagenesis of the variable region, or the like, to obtain a binding protein domain that has the appropriate affinity for the ligand. In this way, almost any physiologically acceptable haptenic compound can be employed as the ligand or to provide an epitope for the ligand. Instead of antibody units, natural receptors can be employed, where the binding region or domain is known and there is a useful or known ligand for binding.

For multimerizing the receptor, the ligand for the ligand-binding region/receptor domains of the inducible proapoptotic polypeptides may be multimeric in the sense that the ligand can have at least two binding sites, with each of the binding sites capable of binding to a ligand receptor region (i.e. a ligand having a first binding site capable of binding the ligand-binding region of a first inducible proapoptotic polypeptide and a second binding site capable of binding the ligand-binding region of a second inducible proapoptotic polypeptide, wherein the ligand-binding regions of the first and the second inducible proapoptotic polypeptides are either identical or distinct). Thus, as used herein, the term "multimeric ligand binding region" refers to a ligand-binding region of an inducible proapoptotic polypeptide of the disclosure that binds to a multimeric ligand. Multimeric ligands of the disclosure include dimeric ligands. A dimeric ligand of the disclosure may have two binding sites capable of binding to the ligand receptor domain. In certain embodiments, multimeric ligands of the disclosure are a dimer or higher order oligomer, usually not greater than about tetrameric, of small synthetic organic molecules, the individual molecules typically being at least about 150 Da and less than about 5 kDa, usually less than about 3 kDa. A variety of pairs of synthetic ligands and receptors can be employed. For example, in embodiments involving natural receptors, dimeric FK506 can be used with an FKBP12 receptor, dimerized cyclosporin A can be used with the cyclophilin receptor, dimerized estrogen with an estrogen receptor, dimerized glucocorticoids with a glucocorticoid receptor, dimerized tetracycline with the tetracycline receptor, dimerized vitamin D with the vitamin D receptor, and the like. Alternatively higher orders of the ligands, e.g., trimeric can be used. For embodiments involving unnatural receptors, e.g., antibody subunits, modified antibody subunits, single chain antibodies comprised of heavy and light chain variable regions in tandem, separated by a flexible linker, or modified receptors, and mutated sequences thereof, and the like, any of a large variety of compounds can be used. A significant characteristic of the units comprising a multimeric ligand of the disclosure is that each binding site is able to bind the receptor with high affinity, and preferably, that they are able to be dimerized chemically. Also, methods are available to balance the hydrophobicity/hydrophilicity of the ligands so that they are able to dissolve in serum at functional levels, yet diffuse across plasma membranes for most applications.

Activation of inducible proapoptotic polypeptides of the disclosure may be accomplished through, for example, chemically induced dimerization (CID) mediated by an induction agent to produce a conditionally controlled protein or polypeptide. Proapoptotic polypeptides of the disclosure not only inducible, but the induction of these polypeptides is also reversible, due to the degradation of the labile dimerizing agent or administration of a monomeric competitive inhibitor.

In certain embodiments, the ligand binding region comprises a FK506 binding protein 12 (FKBP12) polypeptide. In certain embodiments, the ligand binding region comprises a FKBP12 polypeptide having a substitution of valine (V) for phenylalanine (F) at position 36 (F36V). In certain embodiments, in which the ligand binding region comprises a FKBP12 polypeptide having a substitution of valine (V) for phenylalanine (F) at position 36 (F36V), the induction agent may comprise AP1903 (Rimiducid), a synthetic drug (CAS Index Name: 2-Piperidinecarboxylic acid, 1-[(2S)-1-oxo-2-(3,4,5-trimethoxyphenyl)butyl]-, 1,2-ethanediylbis [imino(2-oxo-2,1-ethanediyl)oxy-3,1-phenylene[(1R)-3-(3, 4-dimethoxyphenyl)propylidene]]ester, [2S-[1(R*),2R*[S* [S*[1(R*),2R*]]]]]-(9C1) CAS Registry Number: 195514-63-7; Molecular Formula: C78H98N4O20; Molecular Weight: 1411.65)). In certain embodiments, in which the ligand binding region comprises a FKBP12 polypeptide having a substitution of valine (V) for phenylalanine (F) at position 36 (F36V), the induction agent may comprise AP20187 (CAS Registry Number: 195514-80-8 and Molecular Formula: C82H107N5O20). In certain embodiments, the induction agent is an AP20187 analog, such as, for example, AP1510. As used herein, the induction agents AP20187, AP1903 (Rimiducid) and AP1510 may be used interchangeably.

AP1903 (Rimiducid) API is manufactured by Alphora Research Inc. and AP1903 (Rimiducid) Drug Product for Injection is made by Formatech Inc. It is formulated as a 5 mg/mL solution of AP1903 (Rimiducid) in a 25% solution of the non-ionic solubilizer Solutol HS 15 (250 mg/mL, BASF). At room temperature, this formulation is a clear, slightly yellow solution. Upon refrigeration, this formulation undergoes a reversible phase transition, resulting in a milky solution. This phase transition is reversed upon rewarming to room temperature. The fill is 2.33 mL in a 3 mL glass vial (approximately 10 mg AP1903 (Rimiducid) for Injection total per vial). Upon determining a need to administer AP1903 (Rimiducid), patients may be, for example, administered a single fixed dose of AP1903 (Rimiducid) for Injection (0.4 mg/kg) via IV infusion over 2 hours, using a non-DEHP, non-ethylene oxide sterilized infusion set. The dose of AP1903 (Rimiducid) is calculated individually for all patients, and is not be recalculated unless body weight fluctuates by ≥10%. The calculated dose is diluted in 100 mL in 0.9% normal saline before infusion. In a previous Phase I study of AP1903 (Rimiducid), 24 healthy volunteers were treated with single doses of AP1903 (Rimiducid) for Injection at dose levels of 0.01, 0.05, 0.1, 0.5 and 1.0 mg/kg infused IV over 2 hours. AP1903 (Rimiducid) plasma levels were directly proportional to dose, with mean Cmax values ranging from approximately 10-1275 ng/mL over the 0.01-1.0 mg/kg dose range. Following the initial infusion period, blood concentrations demonstrated a rapid distribution phase, with plasma levels reduced to approximately 18, 7, and 1% of maximal concentration at 0.5, 2 and 10 hours post-dose, respectively. AP1903 (Rimiducid) for Injection was shown to be safe and well tolerated at all dose levels and demonstrated a favorable pharmacokinetic profile. Iuliucci J D, et al., J Clin Pharmacol. 41: 870-9, 2001.

The fixed dose of AP1903 (Rimiducid) for injection used, for example, may be 0.4 mg/kg intravenously infused over 2 hours. The amount of AP1903 (Rimiducid) needed in vitro for effective signaling of cells is 10-100 nM (1600 Da MW). This equates to 16-160 μg/L or ~0.016-1.6 μg/kg (1.6-160 μg/kg). Doses up to 1 mg/kg were well-tolerated in the Phase I study of AP1903 (Rimiducid) described above. Therefore, 0.4 mg/kg may be a safe and effective dose of AP1903 (Rimiducid) for this Phase I study in combination with the therapeutic cells.

The amino acid and/or nucleic acid sequence encoding ligand binding of the disclosure may contain sequence one or more modifications compared to a wild type amino acid or nucleic acid sequence. For example, the amino acid and/or nucleic acid sequence encoding ligand binding region of the disclosure may be a codon-optimized sequence. The one or more modifications may increase the binding affinity of a ligand (e.g. an induction agent) for the ligand binding region of the disclosure compared to a wild type polypeptide. Alternatively, or in addition, the one or more modifications may decrease the immunogenicity of the ligand binding region of the disclosure compared to a wild type polypeptide. Ligand binding regions of the disclosure and/or induction agents of the disclosure may be non-naturally occurring.

Inducible proapoptotic polypeptides of the disclosure comprise a ligand binding region, a linker and a proapoptotic peptide, wherein the inducible proapoptotic polypeptide does not comprise a non-human sequence. In certain embodiments, the non-human sequence comprises a restriction site. The linker may comprise any organic or inorganic material that permits, upon dimerization of the ligand binding region, interaction, cross-linking, cross-activation, or activation of the proapoptotic polypeptides such that the interaction or activation of the proapoptotic polypeptides initiates apoptosis in the cell. In certain embodiments, the linker is a polypeptide. In certain embodiments, the linker is a polypeptide comprising a G/S rich amino acid sequence (a "GS" linker). In certain embodiments, the linker is a polypeptide comprising the amino acid sequence GGGGS (SEQ ID NO: 5). In preferred embodiments, the linker is a polypeptide and the nucleic acid encoding the polypeptide does not contain a restriction site for a restriction endonuclease. Linkers of the disclosure may be non-naturally occurring.

Inducible proapoptotic polypeptides of the disclosure may be expressed in a cell under the transcriptional regulation of any promoter capable of initiating and/or regulating the expression of an inducible proapoptotic polypeptide of the disclosure in that cell. The term "promoter" as used herein refers to a promoter that acts as the initial binding site for RNA polymerase to transcribe a gene. For example, inducible proapoptotic polypeptides of the disclosure may be expressed in a mammalian cell under the transcriptional regulation of any promoter capable of initiating and/or regulating the expression of an inducible proapoptotic polypeptide of the disclosure in a mammalian cell, including, but not limited to native, endogenous, exogenous, and heterologous promoters. Preferred mammalian cells include human cells. Thus, inducible proapoptotic polypeptides of the disclosure may be expressed in a human cell under the transcriptional regulation of any promoter capable of initiating and/or regulating the expression of an inducible proapoptotic polypeptide of the disclosure in a human cell, including, but not limited to, a human promoter or a viral promoter. Exemplary promoters for expression in human cells include, but are not limited to, a human cytomegalovirus (CMV) immediate early gene promoter, a SV40 early promoter, a Rous sarcoma virus long terminal repeat, β-actin promoter, a rat insulin promoter and a glyceraldehyde-3-phosphate dehydrogenase promoter, each of which may be used to obtain high-level expression of an inducible proapoptotic polypeptide of the disclosure. The use of other viral or mammalian cellular or bacterial phage promoters which are well known in the art to achieve expression of an inducible proapoptotic polypeptide of the disclosure is contemplated as well, provided that the levels of expression are sufficient for initiating apoptosis in a cell. By employing a promoter with well-known properties, the level and pattern of expression of the protein of interest following transfection or transformation can be optimized.

Selection of a promoter that is regulated in response to specific physiologic or synthetic signals can permit inducible expression of the inducible proapoptotic polypeptide of the disclosure. The ecdysone system (Invitrogen, Carlsbad, Calif.) is one such system. This system is designed to allow regulated expression of a gene of interest in mammalian cells. It consists of a tightly regulated expression mechanism that allows virtually no basal level expression of a transgene, but over 200-fold inducibility. The system is based on the heterodimeric ecdysone receptor of *Drosophila*, and when ecdysone or an analog such as muristerone A binds to the receptor, the receptor activates a promoter to turn on expression of the downstream transgene high levels of mRNA transcripts are attained. In this system, both monomers of the heterodimeric receptor are constitutively expressed from one vector, whereas the ecdysone-responsive promoter, which drives expression of the gene of interest, is on another plasmid. Engineering of this type of system into a vector of interest may therefore be useful. Another inducible system that may be useful is the Tet-Off™ or Tet-On™ system (Clontech, Palo Alto, Calif.) originally developed by Gossen and Bujard (Gossen and Bujard, Proc. Natl. Acad. Sci. USA, 89:5547-5551, 1992; Gossen et al., Science, 268:1766-1769, 1995). This system also allows high levels of gene expression to be regulated in response to tetracycline or tetracycline derivatives such as doxycycline. In the Tet-On™ system, gene expression is turned on in the presence of doxycycline, whereas in the Tet-Off™ system, gene expression is turned on in the absence of doxycycline. These systems are based on two regulatory elements derived from the tetracycline resistance operon of *E. coli*: the tetracycline operator sequence (to which the tetracycline repressor binds) and the tetracycline repressor protein. The gene of interest is cloned into a plasmid behind a promoter that has tetracycline-responsive elements present in it. A second plasmid contains a regulatory element called the tetracycline-controlled transactivator, which is composed, in the Tet-Off™ system, of the VP16 domain from the herpes simplex virus and the wild-type tetracycline repressor. Thus in the absence of doxycycline, transcription is constitutively on. In the Tet-On™ system, the tetracycline repressor is not wild type and in the presence of doxycycline activates transcription. For gene therapy vector production, the Tet-Off™ system may be used so that the producer cells could be grown in the presence of tetracycline or doxycycline and prevent expression of a potentially toxic transgene, but when the vector is introduced to the patient, the gene expression would be constitutively on.

In some circumstances, it is desirable to regulate expression of a transgene in a gene therapy vector. For example, different viral promoters with varying strengths of activity are utilized depending on the level of expression desired. In mammalian cells, the CMV immediate early promoter is often used to provide strong transcriptional activation. The CMV promoter is reviewed in Donnelly, J. J., et al., 1997. Annu. Rev. Immunol. 15:617-48. Modified versions of the CMV promoter that are less potent have also been used when reduced levels of expression of the transgene are desired. When expression of a transgene in hematopoietic cells is desired, retroviral promoters such as the LTRs from MLV or MMTV are often used. Other viral promoters that are used depending on the desired effect include SV40, RSV LTR, HIV-1 and HIV-2 LTR, adenovirus promoters such as from the E1A, E2A, or MLP region, AAV LTR, HSV-TK, and avian sarcoma virus.

In other examples, promoters may be selected that are developmentally regulated and are active in particular differentiated cells. Thus, for example, a promoter may not be active in a pluripotent stem cell, but, for example, where the pluripotent stem cell differentiates into a more mature cell, the promoter may then be activated.

Similarly tissue specific promoters are used to effect transcription in specific tissues or cells so as to reduce potential toxicity or undesirable effects to non-targeted tissues. These promoters may result in reduced expression compared to a stronger promoter such as the CMV promoter, but may also result in more limited expression, and immunogenicity (Bojak, A., et al., 2002. Vaccine. 20:1975-79; Cazeaux., N., et al., 2002. Vaccine 20:3322-31). For example, tissue specific promoters such as the PSA associated promoter or prostate-specific glandular kallikrein, or the muscle creatine kinase gene may be used where appropriate.

Examples of tissue specific or differentiation specific promoters include, but are not limited to, the following: B29 (B cells); CD14 (monocytic cells); CD43 (leukocytes and platelets); CD45 (hematopoietic cells); CD68 (macrophages); desmin (muscle); elastase-1 (pancreatic acinar cells); endoglin (endothelial cells); fibronectin (differentiating cells, healing tissues); and Flt-1 (endothelial cells); GFAP (astrocytes).

In certain indications, it is desirable to activate transcription at specific times after administration of the gene therapy vector. This is done with such promoters as those that are hormone or cytokine regulatable. Cytokine and inflammatory protein responsive promoters that can be used include K and T kininogen (Kageyama et al., (1987) J. Biol. Chem., 262, 2345-2351), c-fos, TNF-alpha, C-reactive protein (Arcone, et al., (1988) Nucl. Acids Res., 16(8), 3195-3207), haptoglobin (Oliviero et al., (1987) EMBO J., 6, 1905-1912), serum amyloid A2, C/EBP alpha, IL-1, IL-6 (Poli and Cortese, (1989) Proc. Nat'l Acad. Sci. USA, 86, 8202-8206), Complement C3 (Wilson et al., (1990) Mol. Cell. Biol., 6181-6191), IL-8, alpha-1 acid glycoprotein (Prowse and Baumann, (1988) Mol Cell Biol, 8, 42-51), alpha-1 antitrypsin, lipoprotein lipase (Zechner et al., Mol. Cell. Biol., 2394-2401, 1988), angiotensinogen (Ron, et al., (1991) Mol. Cell. Biol., 2887-2895), fibrinogen, c-jun (inducible by phorbol esters, TNF-alpha, UV radiation, retinoic acid, and hydrogen peroxide), collagenase (induced by phorbol esters and retinoic acid), metallothionein (heavy metal and glucocorticoid inducible), Stromelysin (inducible by phorbol ester, interleukin-1 and EGF), alpha-2 macroglobulin and alpha-1 anti-chymotrypsin. Other promoters include, for example, SV40, MMTV, Human Immunodeficiency Virus (MV), Moloney virus, ALV, Epstein Barr virus, Rous Sarcoma virus, human actin, myosin, hemoglobin, and creatine.

It is envisioned that any of the above promoters alone or in combination with another can be useful depending on the action desired. Promoters, and other regulatory elements, are selected such that they are functional in the desired cells or tissue. In addition, this list of promoters should not be construed to be exhaustive or limiting; other promoters that are used in conjunction with the promoters and methods disclosed herein.

Nucleic Acid Molecules

Nucleic acid molecules of the disclosure, including sequences encoding an inducible polypeptide of the disclosure, can be in the form of RNA, such as mRNA, hnRNA, tRNA or any other form, or in the form of DNA, including, but not limited to, cDNA and genomic DNA obtained by cloning or produced synthetically, or any combinations thereof. The DNA can be triple-stranded, double-stranded or single-stranded, or any combination thereof. Any portion of at least one strand of the DNA or RNA can be the coding strand, also known as the sense strand, or it can be the non-coding strand, also referred to as the anti-sense strand.

Isolated nucleic acid molecules of the disclosure can include nucleic acid molecules comprising an open reading frame (ORF), optionally, with one or more introns, e.g., but not limited to, at least one specified portion of at least one sequence encoding a an inducible polypeptide of the disclosure; nucleic acid molecules comprising the coding sequence for a an inducible polypeptide of the disclosure; and nucleic acid molecules which comprise a nucleotide sequence substantially different from those described above but which, due to the degeneracy of the genetic code, still encode an inducible polypeptide of the disclosure as described herein and/or as known in the art. Of course, the genetic code is well known in the art. Thus, it would be routine for one skilled in the art to generate such degenerate nucleic acid variants that code for an inducible polypeptide of the disclosure. See, e.g., Ausubel, et al., supra, and such nucleic acid variants are included in the disclosure.

As indicated herein, nucleic acid molecules of the disclosure which comprise a nucleic acid encoding an inducible polypeptide of the disclosure can include, but are not limited to, those encoding the amino acid sequence of an inducible polypeptide or fragment, by itself; the coding sequence for the entire an inducible polypeptide or a portion thereof; the coding sequence for an inducible polypeptide of the disclosure, fragment or portion, as well as additional sequences, such as the coding sequence of at least one signal leader or fusion peptide, with or without the aforementioned additional coding sequences, such as at least one intron, together with additional, non-coding sequences, including but not limited to, non-coding 5' and 3' sequences, such as the transcribed, non-translated sequences that play a role in transcription, mRNA processing, including splicing and polyadenylation signals (for example, ribosome binding and stability of mRNA); an additional coding sequence that codes for additional amino acids, such as those that provide additional functionalities. Thus, the sequence encoding an inducible polypeptide of the disclosure can be fused to a marker sequence, such as a sequence encoding a peptide that facilitates purification of the fused protein scaffold comprising a protein scaffold fragment or portion.

Construction of Nucleic Acids

The isolated nucleic acids of the disclosure can be made using (a) recombinant methods, (b) synthetic techniques, (c) purification techniques, and/or (d) combinations thereof, as well-known in the art.

The nucleic acids can conveniently comprise sequences in addition to a sequence encoding an inducible polypeptide of the disclosure. For example, a multi-cloning site comprising one or more endonuclease restriction sites can be inserted into the nucleic acid to aid in isolation of the sequence encoding an inducible polypeptide of the disclosure. Also, translatable sequences can be inserted to aid in the isolation of the translated polynucleotide of the disclosure. For example, a hexa-histidine marker sequence provides a convenient means to purify the caspase proteins of the disclosure. The nucleic acid of the disclosure, excluding the coding sequence, is optionally a vector, adapter, or linker for cloning and/or expression of a sequence encoding an inducible polypeptide of the disclosure or an inducible polypeptide of the disclosure.

Additional sequences can be added to such cloning and/or expression sequences to optimize their function in cloning and/or expression, to aid in isolation of the polynucleotide sequence encoding an inducible polypeptide of the disclosure, or to improve the introduction of the polynucleotide sequence encoding an inducible polypeptide of the disclosure into a cell. Use of cloning vectors, expression vectors, adapters, and linkers is well known in the art. (See, e.g., Ausubel, supra; or Sambrook, supra).

Recombinant Methods for Constructing Nucleic Acids

The isolated nucleic acid compositions of this disclosure, such as RNA, cDNA, genomic DNA, or any combination thereof, can be obtained from biological sources using any number of cloning methodologies known to those of skill in the art. In some embodiments, oligonucleotide probes that selectively hybridize, under stringent conditions, to the polynucleotides of the present invention are used to identify the desired sequence in a cDNA or genomic DNA library. The isolation of RNA, construction of cDNA and genomic libraries are well known to those of ordinary skill in the art. (See, e.g., Ausubel, supra; or Sambrook, supra).

Nucleic Acid Screening and Isolation Methods

A cDNA or genomic library can be screened using a probe based upon the sequence of a polynucleotide of the disclosure or fragment thereof. Probes can be used to hybridize with genomic DNA or cDNA sequences to isolate homologous genes in the same or different organisms. Those of skill in the art will appreciate that various degrees of stringency of hybridization can be employed in the assay; and either the hybridization or the wash medium can be stringent. As the conditions for hybridization become more stringent, there must be a greater degree of complementarity between the probe and the target for duplex formation to occur. The degree of stringency can be controlled by one or more of temperature, ionic strength, pH and the presence of a partially denaturing solvent, such as formamide. For example, the stringency of hybridization is conveniently varied by changing the polarity of the reactant solution through, for example, manipulation of the concentration of formamide within the range of 0% to 50%. The degree of complementarity (sequence identity) required for detectable binding will vary in accordance with the stringency of the hybridization medium and/or wash medium. The degree of complementarity will optimally be 100%, or 70-100%, or any range or value therein. However, it should be understood that minor sequence variations in the probes and primers can be compensated for by reducing the stringency of the hybridization and/or wash medium.

Methods of amplification of RNA or DNA are well known in the art and can be used according to the disclosure without undue experimentation, based on the teaching and guidance presented herein.

Known methods of DNA or RNA amplification include, but are not limited to, polymerase chain reaction (PCR) and related amplification processes (see, e.g., U.S. Pat. Nos. 4,683,195, 4,683,202, 4,800,159, 4,965,188, to Mullis, et al.; 4,795,699 and 4,921,794 to Tabor, et al; U.S. Pat. No. 5,142,033 to Innis; U.S. Pat. No. 5,122,464 to Wilson, et al.; U.S. Pat. No. 5,091,310 to Innis; U.S. Pat. No. 5,066,584 to Gyllensten, et al; U.S. Pat. No. 4,889,818 to Gelfand, et al; U.S. Pat. No. 4,994,370 to Silver, et al; U.S. Pat. No. 4,766,067 to Biswas; U.S. Pat. No. 4,656,134 to Ringold) and RNA mediated amplification that uses anti-sense RNA to the target sequence as a template for double-stranded DNA synthesis (U.S. Pat. No. 5,130,238 to Malek, et al, with the tradename NASBA), the entire contents of which references are incorporated herein by reference. (See, e.g., Ausubel, supra; or Sambrook, supra.)

For instance, polymerase chain reaction (PCR) technology can be used to amplify the sequences of polynucleotides of the disclosure and related genes directly from genomic DNA or cDNA libraries. PCR and other in vitro amplification methods can also be useful, for example, to clone nucleic acid sequences that code for proteins to be expressed, to make nucleic acids to use as probes for detecting the presence of the desired mRNA in samples, for nucleic acid sequencing, or for other purposes. Examples of techniques sufficient to direct persons of skill through in vitro amplification methods are found in Berger, supra, Sambrook, supra, and Ausubel, supra, as well as Mullis, et al., U.S. Pat. No. 4,683,202 (1987); and Innis, et al., PCR Protocols A Guide to Methods and Applications, Eds., Academic Press Inc., San Diego, Calif. (1990). Commercially available kits for genomic PCR amplification are known in the art. See, e.g., Advantage-GC Genomic PCR Kit (Clontech). Additionally, e.g., the T4 gene 32 protein (Boehringer Mannheim) can be used to improve yield of long PCR products.

Synthetic Methods for Constructing Nucleic Acids

The isolated nucleic acids of the disclosure can also be prepared by direct chemical synthesis by known methods (see, e.g., Ausubel, et al., supra). Chemical synthesis generally produces a single-stranded oligonucleotide, which can be converted into double-stranded DNA by hybridization with a complementary sequence or by polymerization with a DNA polymerase using the single strand as a template. One of skill in the art will recognize that while chemical synthesis of DNA may be limited to sequences of about 100, 500, and 1000 or more bases, longer sequences can be obtained by the ligation of shorter sequences.

Recombinant Expression Cassettes

The disclosure further provides recombinant expression cassettes comprising a nucleic acid of the disclosure. A nucleic acid sequence of the disclosure, for example, a cDNA or a genomic sequence encoding a portion of an inducible polypeptide of the disclosure, can be used to construct a recombinant expression cassette that can be introduced into at least one desired host cell. A recombinant expression cassette will typically comprise a polynucleotide of the disclosure operably linked to transcriptional initiation regulatory sequences that will direct the transcription of the polynucleotide in the intended host cell. Both heterologous and non-heterologous (i.e., endogenous) promoters can be employed to direct expression of the nucleic acids of the disclosure.

In some embodiments, isolated nucleic acids that serve as promoter, enhancer, or other elements can be introduced in the appropriate position (upstream, downstream or in the intron) of a non-heterologous form of a polynucleotide of the disclosure so as to up or down regulate expression of a polynucleotide of the disclosure. For example, endogenous promoters can be altered in vivo or in vitro by mutation, deletion and/or substitution.

Vectors and Host Cells

The disclosure also relates to vectors that include a sequence encoding an inducible polypeptide of the disclosure, host cells that are genetically engineered with the recombinant vectors, and the production of at least one inducible polypeptide of the disclosure by recombinant techniques, as is well known in the art. See, e.g., Sambrook, et al., supra; Ausubel, et al., supra, each entirely incorporated herein by reference.

Polynucleotides, including a sequence encoding an inducible polypeptide of the disclosure, can optionally be joined to a vector containing a selectable marker for propagation in a host. Generally, a plasmid vector is introduced in a precipitate, such as a calcium phosphate precipitate, or in a complex with a charged lipid. If the vector is a virus, it can be packaged in vitro using an appropriate packaging cell line and then transduced into host cells.

The disclosure provides a composition comprising the transposon the disclosure. In certain embodiments, the composition may further comprise a plasmid comprising a sequence encoding a transposase enzyme. The sequence encoding a transposase enzyme may be an mRNA sequence.

Transposons of the disclosure be episomally maintained or integrated into the genome of the recombinant/modified cell. The transposon may be part of a two component piggyBac system that utilizes a transposon and transposase for enhanced non-viral gene transfer. In certain embodiments of this method, the transposon is a plasmid DNA transposon with a sequence encoding the inducible caspase polypeptide of the disclosure flanked by two cis-regulatory insulator elements. In certain embodiments, the transposon is a piggyBac transposon. In certain embodiments, and, in particular, those embodiments wherein the transposon is a piggyBac transposon, the transposase is a piggyBac™ or a Super piggyBac™ (SPB) transposase.

Transposons of the disclosure may comprise piggyBac transposons. In certain embodiments of the methods of the disclosure, the transposon is a plasmid DNA transposon with a sequence encoding the inducible caspase polypeptide of the disclosure flanked by two cis-regulatory insulator elements. In certain embodiments, the transposon is a piggyBac transposon. In certain embodiments, and, in particular, those embodiments wherein the transposon is a piggyBac transposon, the transposase is a piggyBac™ or a Super piggyBac™ (SPB) transposase. In certain embodiments, and, in particular, those embodiments wherein the transposase is a Super piggyBac™ (SPB) transposase, the sequence encoding the transposase is an mRNA sequence.

In certain embodiments of the methods of the disclosure, the transposase enzyme is a piggyBac™ (PB) transposase enzyme. The piggyBac (PB) transposase enzyme may comprise or consist of an amino acid sequence at least 75%, 80%, 85%, 90%, 95%, 99% or any percentage in between identical to:

(SEQ ID NO: 1)

```
  1   MGSSLDDEHI LSALLQSDDE LVGEDSDSEI SDHVSEDDVQ SDTEEAFIDE VHEVQPTSSG

61   SEILDEQNVI EQPGSSLASN RILTLPQRTI RGKNKHCWST SKSTRRSRVS ALNIVRSQRG

121   PTRMCRNIYD PLLCFKLFFT DEIISEIVKW TNAEISLKRR ESMTGATFRD TNEDEIYAFF

181   GILVMTAVRK DNHMSTDDLF DRSLSMVYVS VMSRDRFDFL IRCLRMDDKS IRPTLRENDV

241   FTPVRKIWDL FIHQCIQNYT PGAHLTIDEQ LLGFRGRCPF RMYIPNKPSK YGIKILMMCD

301   SGTKYMINGM PYLGRGTQTN GVPLGEYYVK ELSKPVHGSC RNITCDNWFT SIPLAKNLLQ

361   EPYKLTIVGT VRSNKREIPE VLKNSRSRPV GTSMFCFDGP LTLVSYKPKP AKMVYLLSSC

421   DEDASINEST GKPQMVMYYN QTKGGVDTLD QMCSVMTCSR KTNRWPMALL YGMINIACIN

481   SFIIYSHNVS SKGEKVQSRK KFMRNLYMSL TSSFMRKRLE APTLKRYLRD NISNILPNEV

541   PGTSDDSTEE PVMKKRTYCT YCPSKIRRKA NASCKKCKKV ICREHNIDMC QSCF.
```

In certain embodiments of the methods of the disclosure, the transposase enzyme is a piggyBac™ (PB) transposase enzyme that comprises or consists of an amino acid sequence having an amino acid substitution at one or more of positions 30, 165, 282, or 538 of the sequence:

```
                                                            (SEQ ID NO: 1)
  1   MGSSLDDEHI LSALLQSDDE LVGEDSDSEI SDHVSEDDVQ SDTEEAFIDE VHEVQPTSSG

61   SEILDEQNVI EQPGSSLASN RILTLPQRTI RGKNKHCWST SKSTRRSRVS ALNIVRSQRG

121   PTRMCRNIYD PLLCFKLFFT DEIISEIVKW TNAEISLKRR ESMTGATFRD TNEDEIYAFF

181   GILVMTAVRK DNHMSTDDLF DRSLSMVYVS VMSRDRFDFL IRCLRMDDKS IRPTLRENDV

241   FTPVRKIWDL FIHQCIQNYT PGAHLTIDEQ LLGFRGRCPF RMYIPNKPSK YGIKILMMCD

301   SGTKYMINGM PYLGRGTQTN GVPLGEYYVK ELSKPVHGSC RNITCDNWFT SIPLAKNLLQ

361   EPYKLTIVGT VRSNKREIPE VLKNSRSRPV GTSMFCFDGP LTLVSYKPKP AKMVYLLSSC

421   DEDASINEST GKPQMVMYYN QTKGGVDTLD QMCSVMTCSR KTNRWPMALL YGMINIACIN

481   SFIIYSHNVS SKGEKVQSRK KFMRNLYMSL TSSFMRKRLE APTLKRYLRD NISNILPNEV

541   PGTSDDSTEE PVMKKRTYCT YCPSKIRRKA NASCKKCKKV ICREHNIDMC QSCF.
```

In certain embodiments, the transposase enzyme is a piggyBac™ (PB) transposase enzyme that comprises or consists of an amino acid sequence having an amino acid substitution at two or more of positions 30, 165, 282, or 538 of the sequence of SEQ ID NO: 1. In certain embodiments, the transposase enzyme is a piggyBac™ (PB) transposase enzyme that comprises or consists of an amino acid sequence having an amino acid substitution at three or more of positions 30, 165, 282, or 538 of the sequence of SEQ ID NO: 1. In certain embodiments, the transposase enzyme is a piggyBac™ (PB) transposase enzyme that comprises or consists of an amino acid sequence having an amino acid substitution at each of the following positions 30, 165, 282, and 538 of the sequence of SEQ ID NO: 1. In certain embodiments, the amino acid substitution at position 30 of the sequence of SEQ ID NO: 1 is a substitution of a valine (V) for an isoleucine (I). In certain embodiments, the amino acid substitution at position 165 of the sequence of SEQ ID NO: 1 is a substitution of a serine (S) for a glycine (G). In certain embodiments, the amino acid substitution at position 282 of the sequence of SEQ ID NO: 1 is a substitution of a valine (V) for a methionine (M). In certain embodiments, the amino acid substitution at position 538 of the sequence of SEQ ID NO: 1 is a substitution of a lysine (K) for an asparagine (N).

In certain embodiments of the methods of the disclosure, the transposase enzyme is a Super piggyBac™ (SPB) transposase enzyme. In certain embodiments, the Super piggyBac™ (SPB) transposase enzymes of the disclosure may comprise or consist of the amino acid sequence of the sequence of SEQ ID NO: 1 wherein the amino acid substitution at position 30 is a substitution of a valine (V) for an isoleucine (I), the amino acid substitution at position 165 is a substitution of a serine (S) for a glycine (G), the amino acid substitution at position 282 is a substitution of a valine (V) for a methionine (M), and the amino acid substitution at position 538 is a substitution of a lysine (K) for an asparagine (N). In certain embodiments, the Super piggyBac™ (SPB) transposase enzyme may comprise or consist of an amino acid sequence at least 75%, 80%, 85%, 90%, 95%, 99% or any percentage in between identical to:

```
                                                            (SEQ ID NO: 2)
  1   MGSSLDDEHI LSALLQSDDE LVGEDSDSEV SDHVSEDDVQ SDTEEAFIDE VHEVQPTSSG

61   SEILDEQNVI EQPGSSLASN RILTLPQRTI RGKNKHCWST SKSTRRSRVS ALNIVRSQRG

121   PTRMCRNIYD PLLCFKLFFT DEIISEIVKW TNAEISLKRR ESMTSATFRD TNEDEIYAFF

181   GILVMTAVRK DNHMSTDDLF DRSLSMVYVS VMSRDRFDFL IRCLRMDDKS IRPTLRENDV

241   FTPVRKIWDL FIHQCIQNYT PGAHLTIDEQ LLGFRGRCPF RVYIPNKPSK YGIKILMMCD

301   SGTKYMINGM PYLGRGTQTN GVPLGEYYVK ELSKPVHGSC RNITCDNWFT SIPLAKNLLQ

361   EPYKLTIVGT VRSNKREIPE VLKNSRSRPV GTSMFCFDGP LTLVSYKPKP AKMVYLLSSC

421   DEDASINEST GKPQMVMYYN QTKGGVDTLD QMCSVMTCSR KTNRWPMALL YGMINIACIN

481   SFIIYSHNVS SKGEKVQSRK KFMRNLYMSL TSSFMRKRLE APTLKRYLRD NISNILPKEV

541   PGTSDDSTEE PVMKKRTYCT YCPSKIRRKA NASCKKCKKV ICREHNIDMC QSCF.
```

In certain embodiments of the methods of the disclosure, including those embodiments wherein the transposase comprises the above-described mutations at positions 30, 165, 282 and/or 538, the piggyBac™ or Super piggyBac™ transposase enzyme may further comprise an amino acid substitution at one or more of positions 3, 46, 82, 103, 119, 125, 177, 180, 185, 187, 200, 207, 209, 226, 235, 240, 241, 243, 258, 296, 298, 311, 315, 319, 327, 328, 340, 421, 436, 456, 470, 486, 503, 552, 570 and 591 of the sequence of SEQ ID NO: 1 or SEQ ID NO: 2. In certain embodiments, including those embodiments wherein the transposase comprises the above-described mutations at positions 30, 165, 282 and/or 538, the piggyBac™ or Super piggyBac™ transposase enzyme may further comprise an amino acid substitution at one or more of positions 46, 119, 125, 177, 180, 185, 187, 200, 207, 209, 226, 235, 240, 241, 243, 296, 298, 311, 315, 319, 327, 328, 340, 421, 436, 456, 470, 485, 503, 552 and 570. In certain embodiments, the amino acid substitution at position 3 of SEQ ID NO: 1 or SEQ ID NO: 2 is a substitution of an asparagine (N) for a serine (S). In certain embodiments, the amino acid substitution at position 46 of SEQ ID NO: 1 or SEQ ID NO: 2 is a substitution of a serine (S) for an alanine (A). In certain embodiments, the amino acid substitution at position 46 of SEQ ID NO: 1 or SEQ ID NO: 2 is a substitution of a threonine (T) for an alanine (A). In certain embodiments, the amino acid substitution at position 82 of SEQ ID NO: 1 or SEQ ID NO: 2 is a substitution of a tryptophan (W) for an isoleucine (I). In certain embodiments, the amino acid substitution at position 103 of SEQ ID NO: 1 or SEQ ID NO: 2 is a substitution of a proline (P) for a serine (S). In certain embodiments, the amino acid substitution at position 119 of SEQ ID NO: 1 or SEQ ID NO: 2 is a substitution of a proline (P) for an arginine (R). In certain embodiments, the amino acid substitution at position 125 of SEQ ID NO: 1 or SEQ ID NO: 2 is a substitution of an alanine (A) a cysteine (C). In certain embodiments, the amino acid substitution at position 125 of SEQ ID NO: 1 or SEQ ID NO: 2 is a substitution of a leucine (L) for a cysteine (C). In certain embodiments, the amino acid substitution at position 177 of SEQ ID NO: 1 or SEQ ID NO: 2 is a substitution of a lysine (K) for a tyrosine (Y). In certain embodiments, the amino acid substitution at position 177 of SEQ ID NO: 1 or SEQ ID NO: 2 is a substitution of a histidine (H) for a tyrosine (Y). In certain embodiments, the amino acid substitution at position 180 of SEQ ID NO: 1 or SEQ ID NO: 2 is a substitution of a leucine (L) for a phenylalanine (F). In certain embodiments, the amino acid substitution at position 180 of SEQ ID NO: 1 or SEQ ID NO: 2 is a substitution of an isoleucine (I) for a phenylalanine (F). In certain embodiments, the amino acid substitution at position 180 of SEQ ID NO: 1 or SEQ ID NO: 2 is a substitution of a valine (V) for a phenylalanine (F). In certain embodiments, the amino acid substitution at position 185 of SEQ ID NO: 1 or SEQ ID NO: 2 is a substitution of a leucine (L) for a methionine (M). In certain embodiments, the amino acid substitution at position 187 of SEQ ID NO: 1 or SEQ ID NO: 2 is a substitution of a glycine (G) for an alanine (A). In certain embodiments, the amino acid substitution at position 200 of SEQ ID NO: 1 or SEQ ID NO: 2 is a substitution of a tryptophan (W) for a phenylalanine (F). In certain embodiments, the amino acid substitution at position 207 of SEQ ID NO: 1 or SEQ ID NO: 2 is a substitution of a proline (P) for a valine (V). In certain embodiments, the amino acid substitution at position 209 of SEQ ID NO: 1 or SEQ ID NO: 2 is a substitution of a phenylalanine (F) for a valine (V). In certain embodiments, the amino acid substitution at position 226 of SEQ ID NO: 1 or SEQ ID NO: 2 is a substitution of a phenylalanine (F) for a methionine (M). In certain embodiments, the amino acid substitution at position 235 of SEQ ID NO: 1 or SEQ ID NO: 2 is a substitution of an arginine (R) for a leucine (L). In certain embodiments, the amino acid substitution at position 240 of SEQ ID NO: 1 or SEQ ID NO: 1 is a substitution of a lysine (K) for a valine (V). In certain embodiments, the amino acid substitution at position 241 of SEQ ID NO: 1 or SEQ ID NO: 2 is a substitution of a leucine (L) for a phenylalanine (F). In certain embodiments, the amino acid substitution at position 243 of SEQ ID NO: 1 or SEQ ID NO: 2 is a substitution of a lysine (K) for a proline (P). In certain embodiments, the amino acid substitution at position 258 of SEQ ID NO: 1 or SEQ ID NO: 2 is a substitution of a serine (S) for an asparagine (N). In certain embodiments, the amino acid substitution at position 296 of SEQ ID NO: 1 or SEQ ID NO: 2 is a substitution of a tryptophan (W) for a leucine (L). In certain embodiments, the amino acid substitution at position 296 of SEQ ID NO: 1 or SEQ ID NO: 2 is a substitution of a tyrosine (Y) for a leucine (L). In certain embodiments, the amino acid substitution at position 296 of SEQ ID NO: 1 or SEQ ID NO: 2 is a substitution of a phenylalanine (F) for a leucine (L). In certain embodiments, the amino acid substitution at position 298 of SEQ ID NO: 1 or SEQ ID NO: 2 is a substitution of a leucine (L) for a methionine (M). In certain embodiments, the amino acid substitution at position 298 of SEQ ID NO: 1 or SEQ ID NO: 2 is a substitution of an alanine (A) for a methionine (M). In certain embodiments, the amino acid substitution at position 298 of SEQ ID NO: 1 or SEQ ID NO: 2 is a substitution of a valine (V) for a methionine (M). In certain embodiments, the amino acid substitution at position 311 of SEQ ID NO: 1 or SEQ ID NO: 2 is a substitution of an isoleucine (I) for a proline (P). In certain embodiments, the amino acid substitution at position 311 of SEQ ID NO: 1 or SEQ ID NO: 2 is a substitution of a valine for a proline (P). In certain embodiments, the amino acid substitution at position 315 of SEQ ID NO: 1 or SEQ ID NO: 2 is a substitution of a lysine (K) for an arginine (R). In certain embodiments, the amino acid substitution at position 319 of SEQ ID NO: 1 or SEQ ID NO: 2 is a substitution of a glycine (G) for a threonine (T). In certain embodiments, the amino acid substitution at position 327 of SEQ ID NO: 1 or SEQ ID NO: 2 is a substitution of an arginine (R) for a tyrosine (Y). In certain embodiments, the amino acid substitution at position 328 of SEQ ID NO: 1 or SEQ ID NO: 2 is a substitution of a valine (V) for a tyrosine (Y). In certain embodiments, the amino acid substitution at position 340 of SEQ ID NO: 1 or SEQ ID NO: 2 is a substitution of a glycine (G) for a cysteine (C). In certain embodiments, the amino acid substitution at position 340 of SEQ ID NO: 1 or SEQ ID NO: 2 is a substitution of a leucine (L) for a cysteine (C). In certain embodiments, the amino acid substitution at position 421 of SEQ ID NO: 1 or SEQ ID NO: 2 is a substitution of a histidine (H) for the aspartic acid (D). In certain embodiments, the amino acid substitution at position 436 of SEQ ID NO: 1 or SEQ ID NO: 2 is a substitution of an isoleucine (I) for a valine (V). In certain embodiments, the amino acid substitution at position 456 of SEQ ID NO: 1 or SEQ ID NO: 2 is a substitution of a tyrosine (Y) for a methionine (M). In certain embodiments, the amino acid substitution at position 470 of SEQ ID NO: 1 or SEQ ID NO: 2 is a substitution of a phenylalanine (F) for a leucine (L). In certain embodiments, the amino acid substitution at position 485 of SEQ ID NO: 1 or SEQ ID NO: 2 is a substitution of a lysine (K) for a serine (S). In certain embodiments, the amino acid substitution at position 503 of SEQ ID NO: 1 or SEQ ID NO: 2 is a substitution of a leucine (L) for a methionine (M). In certain embodiments, the amino acid substitution at position 503 of SEQ ID NO: 1 or SEQ ID NO: 2 is a substitution of an isoleucine (I) for a methionine (M). In certain embodiments, the amino acid substitution at position 552 of SEQ ID NO: 1 or SEQ ID NO: 2 is a substitution of a lysine (K) for a valine (V). In certain embodiments, the amino acid substitution at position 570 of SEQ ID NO: 1 or SEQ ID NO: 2 is a substitution of a threonine (T) for an alanine (A). In certain embodiments, the amino acid substitution at position 591 of SEQ ID NO: 1 or SEQ ID NO: 2 is a substitution of a proline (P) for a glutamine (Q). In certain embodiments, the amino acid substitution at position 591 of SEQ ID NO: 1 or SEQ ID NO: 2 is a substitution of an arginine (R) for a glutamine (Q).

In certain embodiments of the methods of the disclosure, including those embodiments wherein the transposase comprises the above-described mutations at positions 30, 165, 282 and/or 538, the piggyBac™ transposase enzyme may comprise or the Super piggyBac™ transposase enzyme may further comprise an amino acid substitution at one or more of positions 103, 194, 372, 375, 450, 509 and 570 of the sequence of SEQ ID NO: 1 or SEQ ID NO: 2. In certain embodiments of the methods of the disclosure, including those embodiments wherein the transposase comprises the above-described mutations at positions 30, 165, 282 and/or 538, the piggyBac™ transposase enzyme may comprise or the Super piggyBac™ transposase enzyme may further comprise an amino acid substitution at two, three, four, five, six or more of positions 103, 194, 372, 375, 450, 509 and 570 of the sequence of SEQ ID NO: 1 or SEQ ID NO: 2. In certain embodiments, including those embodiments wherein the transposase comprises the above-described mutations at positions 30, 165, 282 and/or 538, the piggyBac™ transposase enzyme may comprise or the Super piggyBac™ transposase enzyme may further comprise an amino acid substitution at positions 103, 194, 372, 375, 450, 509 and 570 of the sequence of SEQ ID NO: 1 or SEQ ID NO: 2. In certain embodiments, the amino acid substitution at position 103 of SEQ ID NO: 1 or SEQ ID NO: 2 is a substitution of a proline (P) for a serine (S). In certain embodiments, the amino acid substitution at position 194 of SEQ ID NO: 1 or SEQ ID NO: 2 is a substitution of a valine (V) for a methionine (M). In certain embodiments, the amino acid substitution at position 372 of SEQ ID NO: 1 or SEQ ID NO: 2 is a substitution of an alanine (A) for an arginine (R). In certain embodiments, the amino acid substitution at position 375 of SEQ ID NO: 1 or SEQ ID NO: 2 is a substitution of an alanine (A) for a lysine (K). In certain embodiments, the amino acid substitution at position 450 of SEQ ID NO: 1 or SEQ ID NO: 2 is a substitution of an asparagine (N) for an aspartic acid (D). In certain embodiments, the amino acid substitution at position 509 of SEQ ID NO: 1 or SEQ ID NO: 2 is a substitution of a glycine (G) for a serine (S). In certain embodiments, the amino acid substitution at position 570 of SEQ ID NO: 1 or SEQ ID NO: 2 is a substitution of a serine (S) for an asparagine (N). In certain embodiments, the piggyBac™ transposase enzyme may comprise a substitution of a valine (V) for a methionine (M) at position 194 of SEQ ID NO: 1. In certain embodiments, including those embodiments wherein the piggyBac™ transposase enzyme may comprise a substitution of a valine (V) for a methionine (M) at position 194 of SEQ ID NO: 1, the piggyBac™ transposase enzyme may further comprise an amino acid substitution at positions 372, 375 and 450 of the sequence of SEQ ID NO: 1 or SEQ ID NO: 2. In certain embodiments, the piggyBac™ transposase enzyme may comprise a substitution of a valine (V) for a methionine (M) at position 194 of SEQ ID NO: 1, a substitution of an alanine (A) for an arginine (R) at position 372 of SEQ ID NO: 1, and a substitution of an alanine (A) for a lysine (K) at position 375 of SEQ ID NO: 1. In certain embodiments, the piggyBac™ transposase enzyme may comprise a substitution of a valine (V) for a methionine (M) at position 194 of SEQ ID NO: 1, a substitution of an alanine (A) for an arginine (R) at position 372 of SEQ ID NO: 1, a substitution of an alanine (A) for a lysine (K) at position 375 of SEQ ID NO: 1 and a substitution of an asparagine (N) for an aspartic acid (D) at position 450 of SEQ ID NO: 1.

In certain embodiments of the methods of the disclosure, the transposon is a Sleeping Beauty transposon. In certain embodiments, and, in particular, those embodiments wherein the transposon is a Sleeping Beauty transposon, the transposase is a Sleeping Beauty transposase or a hyperactive Sleeping Beauty transposase (SB100X).

In certain embodiments of the methods of the disclosure, the Sleeping Beauty transposase enzyme comprises an amino acid sequence at least 75%, 80%, 85%, 90%, 95%, 99% or any percentage in between identical to:

```
                                                          (SEQ ID NO: 19)
  1    MGKSKEISQD LRKKIVDLHK SGSSLGAISK RLKVPRSSVQ TIVRKYKHHG TTQPSYRSGR

61    RRVLSPRDER TLVRKVQINP RTTAKDLVKM LEETGTKVSI STVKRVLYRH NLKGRSARKK

121    PLLQNRHKKA RLRFATAHGD KDRTFWRNVL WSDETKIELF GHNDHRYVWR KKGEACKPKN

181    TIPTVKHGGG SIMLWGCFAA GGTGALHKID GIMRKENYVD ILKQHLKTSV RKLKLGRKWV

241    FQMDNDPKHT SKVVAKWLKD NKVKVLEWPS QSPDLNPIEN LWAELKKRVR ARRPTNLTQL

301    HQLCQEEWAK IHPTYCGKLV EGYPKRLTQV KQFKGNATKY.
```

In certain embodiments of the methods of the disclosure, the hyperactive Sleeping Beauty (SB100X) transposase enzyme comprises an amino acid sequence at least 75%, 80%, 85%, 90%, 95%, 99% or any percentage in between identical to:

```
                                                          (SEQ ID NO: 20)
  1    MGKSKEISQD LRKRIVDLHK SGSSLGAISK RLAVPRSSVQ TIVRKYKHHG TTQPSYRSGR

61    RRVLSPRDER TLVRKVQINP RTTAKDLVKM LEETGTKVSI STVKRVLYRH NLKGHSARKK

121    PLLQNRHKKA RLRFATAHGD KDRTFWRNVL WSDETKIELF GHNDHRYVWR KKGEACKPKN

181    TIPTVKHGGG SIMLWGCFAA GGTGALHKID GIMDAVQYVD ILKQHLKTSV RKLKLGRKWV

241    FQHDNDPKHT SKVVAKWLKD NKVKVLEWPS QSPDLNPIEN LWAELKKRVR ARRPTNLTQL

301    HQLCQEEWAK IHPNYCGKLV EGYPKRLTQV KQFKGNATKY.
```

In certain embodiments of the methods of the disclosure, the transposase is a Helitron transposase. Helitron transposases mobilize the Helraiser transposon, an ancient element from the bat genome that was active about 30 to 36 million years ago. An exemplary Helraiser transposon of the disclosure includes Helibat1, which comprises a nucleic acid sequence comprising:

(SEQ ID NO: 21)
```
   1 TCCTATATAA TAAAAGAGAA ACATGCAAAT TGACCATCCC TCCGCTACGC TCAAGCCACG
  61 CCCACCAGCC AATCAGAAGT GACTATGCAA ATTAACCCAA CAAAGATGGC AGTTAAATTT
 121 GCATACGCAG GTGTCAAGCG CCCCAGGAGG CAACGGCGGC CGCGGGCTCC CAGGACCTTC
 181 GCTGGCCCCG GGAGGCGAGG CCGGCCGCGC CTAGCCACAC CCGCGGGCTC CCGGGACCTT
 241 CGCCAGCAGA GAGCAGAGCG GGAGAGCGGG CGGAGAGCGG GAGGTTTGGA GGACTTGGCA
 301 GAGCAGGAGG CCGCTGGACA TAGAGCAGAG CGAGAGAGAG GGTGGCTTGG AGGGCGTGGC
 361 TCCCTCTGTC ACCCCAGCTT CCTCATCACA GCTGTGGAAA CTGACAGCAG GGAGGAGGAA
 421 GTCCCACCCC CACAGAATCA GCCAGAATCA GCCGTTGGTC AGACAGCTCT CAGCGGCCTG
 481 ACAGCCAGGA CTCTCATTCA CCTGCATCTC AGACCGTGAC AGTAGAGAGG TGGGACTATG
 541 TCTAAAGAAC AACTGTTGAT ACAACGTAGC TCTGCAGCCG AAAGATGCCG GCGTTATCGA
 601 CAGAAAATGT CTGCAGAGCA ACGTGCGTCT GATCTTGAAA GAAGGCGGCG CCTGCAACAG
 661 AATGTATCTG AAGAGCAGCT ACTGGAAAAA CGTCGCTCTG AAGCCGAAAA ACAGCGGCGT
 721 CATCGACAGA AAATGTCTAA AGACCAACGT GCCTTTGAAG TTGAAAGAAG GCGGTGGCGA
 781 CGACAGAATA TGTCTAGAGA ACAGTCATCA ACAAGTACTA CCAATACCGG TAGGAACTGC
 841 CTTCTCAGCA AAAATGGAGT ACATGAGGAT GCAATTCTCG AACATAGTTG TGGTGGAATG
 901 ACTGTTCGAT GTGAATTTTG CCTATCACTA AATTTCTCTG ATGAAAAACC ATCCGATGGG
 961 AAATTTACTC GATGTTGTAG CAAAGGGAAA GTCTGTCCAA ATGATATACA TTTTCCAGAT
1021 TACCCGGCAT ATTTAAAAAG ATTAATGACA AACGAAGATT CTGACAGTAA AAATTTCATG
1081 GAAAATATTC GTTCCATAAA TAGTTCTTTT GCTTTTGCTT CCATGGGTGC AAATATTGCA
1141 TCGCCATCAG GATATGGGCC ATACTGTTTT AGAATACACG ACAAGTTTA TCACCGTACT
1201 GGAACTTTAC ATCCTTCGGA TGGTGTTTCT CGGAAGTTTG CTCAACTCTA TATTTTGGAT
1261 ACAGCCGAAG CTACAAGTAA AAGATTAGCA ATGCCAGAAA ACCAGGGCTG CTCAGAAAGA
1321 CTCATGATCA ACATCAACAA CCTCATGCAT GAAATAAATG AATTAACAAA ATCGTACAAG
1381 ATGCTACATG AGGTAGAAAA GGAAGCCCAA TCTGAAGCAG CAGCAAAAGG TATTGCTCCC
1441 ACAGAAGTAA CAATGGCGAT TAAATACGAT CGTAACAGTG ACCCAGGTAG ATATAATTCT
1501 CCCCGTGTAA CCGAGGTTGC TGTCATATTC AGAAACGAAG ATGGAGAACC TCCTTTTGAA
1561 AGGGACTTGC TCATTCATTG TAAACCAGAT CCCAATAATC CAAATGCCAC TAAAATGAAA
1621 CAAATCAGTA TCCTGTTTCC TACATTAGAT GCAATGACAT ATCCTATTCT TTTTCCACAT
1681 GGTGAAAAAG CTGGGGAAC AGATATTGCA TTAAGACTCA GAGACAACAG TGTAATCGAC
1741 AATAATACTA GACAAAATGT AAGGACACGA GTCACACAAA TGCAGTATTA TGGATTTCAT
1801 CTCTCTGTGC GGGACACGTT CAATCCTATT TTAAATGCAG GAAAATTAAC TCAACAGTTT
1861 ATTGTGGATT CATATTCAAA AATGGAGGCC AATCGGATAA ATTTCATCAA AGCAAACCAA
1921 TCTAAGTTGA GAGTTGAAAA ATATAGTGGT TTGATGGATT ATCTCAAATC TAGATCTGAA
1981 AATGACAATG TGCCGATTGG TAAAATGATA ATACTTCCAT CATCTTTTGA GGGTAGTCCC
2041 AGAAATATGC AGCAGCGATA TCAGGATGCT ATGGCAATTG TAACGAAGTA TGGCAAGCCC
2101 GATTTATTCA TAACCATGAC ATGCAACCCC AAATGGGCAG ATATTACAAA CAATTTACAA
2161 CGCTGGCAAA AAGTTGAAAA CAGACCTGAC TTGGTAGCCA GAGTTTTTAA TATTAAGCTG
2221 AATGCTCTTT TAAATGATAT ATGTAAATTC CATTTATTTG GCAAAGTAAT AGCTAAAATT
2281 CATGTCATTG AATTTCAGAA ACGCGGACTG CCTCACGCTC ACATATTATT GATATTAGAT
2341 AGTGAGTCCA AATTACGTTC AGAAGATGAC ATTGACCGTA TAGTTAAGGC AGAAATTCCA
```

-continued

```
2401  GATGAAGACC AGTGTCCTCG ACTTTTTCAA ATTGTAAAAT CAAATATGGT ACATGGACCA
2461  TGTGGAATAC AAAATCCAAA TAGTCCATGT ATGGAAAATG GAAAATGTTC AAAGGGATAT
2521  CCAAAAGAAT TTCAAAATGC GACCATTGGA AATATTGATG GATATCCCAA ATACAAACGA
2581  AGATCTGGTA GCACCATGTC TATTGGAAAT AAAGTTGTCG ATAACACTTG GATTGTCCCT
2641  TATAACCCGT ATTTGTGCCT TAAATATAAC TGTCATATAA ATGTTGAAGT CTGTGCATCA
2701  ATTAAAAGTG TCAAATATTT ATTTAAATAC ATCTATAAAG GGCACGATTG TGCAAATATT
2761  CAAATTTCTG AAAAAAATAT TATCAATCAT GACGAAGTAC AGGACTTCAT TGACTCCAGG
2821  TATGTGAGCG CTCCTGAGGC TGTTTGGAGA CTTTTTGCAA TGCGAATGCA TGACCAATCT
2881  CATGCAATCA AAGATTAGC TATTCATTTG CCAAATGATC AGAATTTGTA TTTTCATACC
2941  GATGATTTTG CTGAAGTTTT AGATAGGGCT AAAAGGCATA ACTCGACTTT GATGGCTTGG
3001  TTCTTATTGA ATAGAGAAGA TTCTGATGCA CGTAATTATT ATTATTGGGA GATTCCACAG
3061  CATTATGTGT TTAATAATTC TTTGTGGACA AAACGCCGAA AGGGTGGGAA TAAAGTATTA
3121  GGTAGACTGT TCACTGTGAG CTTTAGAGAA CCAGAACGAT ATTACCTTAG ACTTTTGCTT
3181  CTGCATGTAA AAGGTGCGAT AAGTTTTGAG GATCTGCGAA CTGTAGGAGG TGTAACTTAT
3241  GATACATTTC ATGAAGCTGC TAAACACCGA GGATTATTAC TTGATGACAC TATCTGGAAA
3301  GATACGATTG ACGATGCAAT CATCCTTAAT ATGCCCAAAC AACTACGGCA ACTTTTTGCA
3361  TATATATGTG TGTTTGGATG TCCTTCTGCT GCAGACAAAT TATGGGATGA GAATAAATCT
3421  CATTTTATTG AAGATTTCTG TTGGAAATTA CACCGAAGAG AAGGTGCCTG TGTGAACTGT
3481  GAAATGCATG CCCTTAACGA AATTCAGGAG GTATTCACAT TGCATGGAAT GAAATGTTCA
3541  CATTTCAAAC TTCCGGACTA TCCTTTATTA ATGAATGCAA ATACATGTGA TCAATTGTAC
3601  GAGCAACAAC AGGCAGAGGT TTTGATAAAT TCTCTGAATG ATGAACAGTT GGCAGCCTTT
3661  CAGACTATAA CTTCAGCCAT CGAAGATCAA ACTGTACACC CCAAATGCTT TTTCTTGGAT
3721  GGTCCAGGTG GTAGTGGAAA ACATATCTG TATAAAGTTT TAACACATTA TATTAGAGGT
3781  CGTGGTGGTA CTGTTTTACC CACAGCATCT ACAGGAATTG CTGCAAATTT ACTTCTTGGT
3841  GGAAGAACCT TCATTCCCA ATATAAATTA CCAATTCCAT TAAATGAAAC TTCAATTTCT
3901  AGACTCGATA TAAAGAGTGA AGTTGCTAAA ACCATTAAAA AGGCCCAACT TCTCATTATT
3961  GATGAATGCA CCATGGCATC CAGTCATGCT ATAAACGCCA TAGATAGATT ACTAAGAGAA
4021  ATTATGAATT TGAATGTTGC ATTTGGTGGG AAAGTTCTCC TTCTCGGAGG GGATTTTCGA
4081  CAATGTCTCA GTATTGTACC ACATGCTATG CGATCGGCCA TAGTACAAAC GAGTTTAAAG
4141  TACTGTAATG TTTGGGGATG TTTCAGAAAG TTGTCTCTTA AAACAAATAT GAGATCAGAG
4201  GATTCTGCTT ATAGTGAATG GTTAGTAAAA CTTGGAGATG GCAAACTTGA TAGCAGTTTT
4261  CATTTAGGAA TGGATATTAT TGAAATCCCC CATGAAATGA TTTGTAACGG ATCTATTATT
4321  GAAGCTACCT TTGGAAATAG TATATCTATA GATAATATTA AAATATATC TAAACGTGCA
4381  ATTCTTTGTC CAAAAAATGA GCATGTTCAA AAATTAAATG AAGAAATTTT GGATATACTT
4441  GATGGAGATT TCACACATA TTTGAGTGAT GATTCCATTG ATTCAACAGA TGATGCTGAA
4501  AAGGAAAATT TTCCCATCGA ATTTCTTAAT AGTATTACTC CTTCGGGAAT GCCGTGTCAT
4561  AAATTAAAAT TGAAAGTGGG TGCAATCATC ATGCTATTGA GAAATCTTAA TAGTAAATGG
4621  GGTCTTTGTA ATGGTACTAG ATTTATTATC AAAAGATTAC GACCTAACAT TATCGAAGCT
4681  GAAGTATTAA CAGGATCTGC AGAGGGAGAG GTTGTTCTGA TTCCAAGAAT TGATTTGTCC
4741  CCATCTGACA CTGGCCTCCC ATTTAAATTA ATTCGAAGAC AGTTTCCCGT GATGCCAGCA
4801  TTTGCGATGA CTATTAATAA ATCACAAGGA CAAACTCTAG ACAGAGTAGG AATATTCCTA
```

-continued

```
4861  CCTGAACCCG TTTTCGCACA TGGTCAGTTA TATGTTGCTT TCTCTCGAGT TCGAAGAGCA

4921  TGTGACGTTA AAGTTAAAGT TGTAAATACT TCATCACAAG GGAAATTAGT CAAGCACTCT

4981  GAAAGTGTTT TTACTCTTAA TGTGGTATAC AGGGAGATAT TAGAATAAGT TTAATCACTT

5041  TATCAGTCAT TGTTTGCATC AATGTTGTTT TTATATCATG TTTTTGTTGT TTTTATATCA

5101  TGTCTTTGTT GTTGTTATAT CATGTTGTTA TTGTTTATTT ATTAATAAAT TTATGTATTA

5161  TTTTCATATA CATTTACTC ATTTCCTTTC ATCTCTCACA CTTCTATTAT AGAGAAAGGG

5221  CAAATAGCAA TATTAAAATA TTTCCTCTAA TTAATTCCCT TTCAATGTGC ACGAATTTCG

5281  TGCACCGGGC CACTAG.
```

Unlike other transposases, the Helitron transposase does not contain an RNase-H like catalytic domain, but instead comprises a RepHel motif made up of a replication initiator domain (Rep) and a DNA helicase domain. The Rep domain is a nuclease domain of the HUH superfamily of nucleases.

An exemplary Helitron transposase of the disclosure comprises an amino acid sequence comprising:

```
                                                           (SEQ ID NO: 22)
   1  MSKEQLLIQR SSAAERCRRY RQKMSAEQRA SDLERRRRLQ QNVSEEQLLE KRRSEAEKQR

61  RHRQKMSKDQ RAFEVERRRW RRQNMSREQS STSTTNTGRN CLLSKNGVHE DAILEHSCGG

121  MTVRCEFCLS LNFSDEKPSD GKFTRCCSKG KVCPNDIHFP DYPAYLKRLM TNEDSDSKNF

181  MENIRSINSS FAFASMGANI ASPSGYGPYC FRIHGQVYHR TGTLHPSDGV SRKFAQLYIL

241  DTAEATSKRL AMPENQGCSE RLMININNLM HEINELTKSY KMLHEVEKEA QSEAAAKGIA

301  PTEVTMAIKY DRNSDPGRYN SPRVTEVAVI FRNEDGEPPF ERDLLIHCKP DPNNPNATKM

361  KQISILFPTL DAMTYPILFP HGEKGWGTDI ALRLRDNSVI DNNTRQNVRT RVTQMQYYGF

421  HLSVRDTFNP ILNAGKLTQQ FIVDSYSKME ANRINFIKAN QSKLRVEKYS GLMDYLKSRS

481  ENDNVPIGKM IILPSSFEGS PRNMQQRYQD AMAIVTKYGK PDLFITMTCN PKWADITNNL

541  QRWQKVENRP DLVARVFNIK LNALLNDICK FHLFGKVIAK IHVIEFQKRG LPHAHILLIL

601  DSESKLRSED DIDRIVKAEI PDEDQCPRLF QIVKSNMVHG PCGIQNPNSP CMENGKCSKG

661  YPKEFQNATI GNIDGYPKYK RRSGSTMSIG NKVVDNTWIV PYNPYLCLKY NCHINVEVCA

721  SIKSVKYLFK YIYKGHDCAN IQISEKNIIN HDEVQDFIDS RYVSAPEAVW RLFAMRMHDQ

781  SHAITRLAIH LPNDQNLYFH TDDFAEVLDR AKRHNSTLMA WFLLNREDSD ARNYYYWEIP

841  QHYVFNNSLW TKRRKGGNKV LGRLFTVSFR EPERYYLRLL LLHVKGAISF EDLRTVGGVT

901  YDTFHEAAKH RGLLLDDTIW KDTIDDAIIL NMPKQLRQLF AYICVFGCPS AADKLWDENK

961  SHFIEDFCWK LHRREGACVN CEMHALNEIQ EVFTLHGMKC SHFKLPDYPL LMNANTCDQL

1021  YEQQQAEVLI NSLNDEQLAA FQTITSAIED QTVHPKCFFL DGPGGSGKTY LYKVLTHYIR

1081  GRGGTVLPTA STGIAANLLL GGRTFHSQYK LPIPLNETSI SRLDIKSEVA KTIKKAQLLI

1141  IDECTMASSH AINAIDRLLR EIMNLNVAFG GKVLLLGGDF RQCLSIVPHA MRSAIVQTSL

1201  KYCNVWGCFR KLSLKTNMRS EDSAYSEWLV KLGDGKLDSS FHLGMDIIEI PHEMICNGSI

1261  IEATFGNSIS IDNIKNISKR AILCPKNEHV QKLNEEILDI LDGDFHTYLS DDSIDSTDDA

1321  EKENFPIEFL NSITPSGMPC HKLKLKVGAI IMLLRNLNSK WGLCNGTRFI IKRLRPNIIE

1381  AEVLTGSAEG EVVLIPRIDL SPSDTGLPFK LIRRQFPVMP AFAMTINKSQ GQTLDRVGIF

1441  LPEPVFAHGQ LYVAFSRVRR ACDVKVKVVN TSSQGKLVKH SESVFTLNVV YREILE.
```

In Helitron transpositions, a hairpin close to the 3' end of the transposon functions as a terminator. However, this hairpin can be bypassed by the transposase, resulting in the transduction of flanking sequences. In addition, Helraiser transposition generates covalently closed circular intermediates. Furthermore, Helitron transpositions can lack target site duplications. In the Helraiser sequence, the transposase is flanked by left and right terminal sequences termed LTS and RTS. These sequences terminate with a conserved 5'-TC/CTAG-3' motif. A 19 bp palindromic sequence with the potential to form the hairpin termination structure is located 11 nucleotides upstream of the RTS and consists of the sequence

```
                                                    (SEQ ID NO: 23)
        GTGCACGAATTTCGTGCACCGGGCCACTAG.
```

In certain embodiments of the methods of the disclosure, the transposase is a Tol2 transposase. Tol2 transposons may be isolated or derived from the genome of the medaka fish, and may be similar to transposons of the hAT family. Exemplary Tol2 transposons of the disclosure are encoded by a sequence comprising about 4.7 kilobases and contain a gene encoding the Tol2 transposase, which contains four exons. An exemplary Tol2 transposase of the disclosure comprises an amino acid sequence comprising the following:

```
                                                                (SEQ ID NO: 24)
  1    MEEVCDSSAA ASSTVQNQPQ DQEHPWPYLR EFFSLSGVNK DSFKMKCVLC LPLNKEISAF

61    KSSPSNLRKH IERMHPNYLK NYSKLTAQKR KIGTSTHASS SKQLKVDSVF PVKHVSPVTV

121    NKAILRYIIQ GLHPFSTVDL PSFKELISTL QPGISVITRP TLRSKIAEAA LIMKQKVTAA

181    MSEVEWIATT TDCWTARRKS FIGVTAHWIN PGSLERHSAA LACKRLMGSH TFEVLASAMN

241    DIHSEYEIRD KVVCTTTDSG SNFMKAFRVF GVENNDIETE ARRCESDDTD SEGCGEGSDG

301    VEFQDASRVL DQDDGFEFQL PKHQKCACHL LNLVSSVDAQ KALSNEHYKK LYRSVFGKCQ

361    ALWNKSSRSA LAAEAVESES RLQLLRPNQT RWNSTFMAVD RILQICKEAG EGALRNICTS

421    LEVPMFNPAE MLFLTEWANT MRPVAKVLDI LQAETNTQLG WLLPSVHQLS LKLQRLHHSL

481    RYCDPLVDAL QQGIQTRFKH MFEDPEIIAA AILLPKFRTS WTNDETIIKR GMDYIRVHLE

541    PLDHKKELAN SSSDDEDFFA SLKPTTHEAS KELDGYLACV SDTRESLLTF PAICSLSIKT

601    NTPLPASAAC ERLFSTAGLL FSPKRARLDT NNFENQLLLK LNLRFYNFE.
```

An exemplary Tol2 transposon of the disclosure, including inverted repeats, subterminal sequences and the Tol2 transposase, is encoded by a nucleic acid sequence comprising the following:

```
                                                                (SEQ ID NO: 25)
  1    CAGAGGTGTA AAGTACTTGA GTAATTTTAC TTGATTACTG TACTTAAGTA TTATTTTTGG

61    GGATTTTTAC TTTACTTGAG TACAATTAAA AATCAATACT TTTACTTTTA CTTAATTACA

121    TTTTTTTAGA AAAAAAGTA CTTTTTACTC CTTACAATTT TATTTACAGT CAAAAAGTAC

181    TTATTTTTTG GAGATCACTT CATTCTATTT TCCCTTGCTA TTACCAAACC AATTGAATTG

241    CGCTGATGCC CAGTTTAATT TAAATGTTAT TTATTCTGCC TATGAAAATC GTTTTCACAT

301    TATATGAAAT TGGTCAGACA TGTTCATTGG TCCTTTGGAA GTGACGTCAT GTCACATCTA

361    TTACCACAAT GCACAGCACC TTGACCTGGA AATTAGGGAA ATTATAACAG TCAATCAGTG
```

```
-continued
 421 GAAGAAAATG GAGGAAGTAT GTGATTCATC AGCAGCTGCG AGCAGCACAG TCCAAAATCA
 481 GCCACAGGAT CAAGAGCACC CGTGGCCGTA TCTTCGCGAA TTCTTTTCTT TAAGTGGTGT
 541 AAATAAAGAT TCATTCAAGA TGAAATGTGT CCTCTGTCTC CCGCTTAATA AAGAAATATC
 601 GGCCTTCAAA AGTTCGCCAT CAAACCTAAG GAAGCATATT GAGGTAAGTA CATTAAGTAT
 661 TTTGTTTTAC TGATAGTTTT TTTTTTTTTT TTTTTTTTTT TTTTTGGGTG TGCATGTTTT
 721 GACGTTGATG GCGCGCCTTT TATATGTGTA GTAGGCCTAT TTTCACTAAT GCATGCGATT
 781 GACAATATAA GGCTCACGTA ATAAAATGCT AAAATGCATT TGTAATTGGT AACGTTAGGT
 841 CCACGGGAAA TTTGGCGCCT ATTGCAGCTT TGAATAATCA TTATCATTCC GTGCTCTCAT
 901 TGTGTTTGAA TTCATGCAAA ACACAAGAAA ACCAAGCGAG AAATTTTTTT CCAAACATGT
 961 TGTATTGTCA AAACGGTAAC ACTTTACAAT GAGGTTGATT AGTTCATGTA TTAACTAACA
1021 TTAAATAACC ATGAGCAATA CATTTGTTAC TGTATCTGTT AATCTTTGTT AACGTTAGTT
1081 AATAGAAATA CAGATGTTCA TTGTTTGTTC ATGTTAGTTC ACAGTGCATT AACTAATGTT
1141 AACAAGATAT AAAGTATTAG TAAATGTTGA AATTAACATG TATACGTGCA GTTCATTATT
1201 AGTTCATGTT AACTAATGTA GTTAACTAAC GAACCTTATT GTAAAAGTGT TACCATCAAA
1261 ACTAATGTAA TGAAATCAAT TCACCCTGTC ATGTCAGCCT TACAGTCCTG TGTTTTTGTC
1321 AATATAATCA GAAATAAAAT TAATGTTTGA TTGTCACTAA ATGCTACTGT ATTTCTAAAA
1381 TCAACAAGTA TTTAACATTA TAAAGTGTGC AATTGGCTGC AAATGTCAGT TTTATTAAAG
1441 GGTTAGTTCA CCCAAAAATG AAAATAATGT CATTAATGAC TCGCCCTCAT GTCGTTCCAA
1501 GCCCGTAAGA CCTCCGTTCA TCTTCAGAAC ACAGTTTAAG ATATTTTAGA TTTAGTCCGA
1561 GAGCTTTCTG TGCCTCCATT GAGAATGTAT GTACGGTATA CTGTCCATGT CCAGAAAGGT
1621 AATAAAAACA TCAAAGTAGT CCATGTGACA TCAGTGGGTT AGTTAGAATT TTTTGAAGCA
1681 TCGAATACAT TTTGGTCCAA AAATAACAAA ACCTACGACT TTATTCGGCA TTGTATTCTC
1741 TTCCGGGTCT GTTGTCAATC CGCGTTCACG ACTTCGCAGT GACGCTACAA TGCTGAATAA
1801 AGTCGTAGGT TTTGTTATTT TTGGACCAAA ATGTATTTTC GATGCTTCAA ATAATTCTAC
1861 CTAACCCACT GATGTCACAT GGACTACTTT GATGTTTTTA TTACCTTTCT GGACATGGAC
1921 AGTATACCGT ACATACATTT TCAGTGGAGG GACAGAAAGC TCTCGGACTA AATCTAAAAT
1981 ATCTTAAACT GTGTTCCGAA GATGAACGGA GGTGTTACGG GCTTGGAACG ACATGAGGGT
2041 GAGTCATTAA TGACATCTTT TCATTTTTGG GTGAACTAAC CCTTTAATGC TGTAATCAGA
2101 GAGTGTATGT GTAATTGTTA CATTTATTGC ATACAATATA AATATTTATT TGTTGTTTTT
2161 ACAGAGAATG CACCCAAATT ACCTCAAAAA CTACTCTAAA TTGACAGCAC AGAAGAGAAA
2221 GATCGGGACC TCCACCCATG CTTCCAGCAG TAAGCAACTG AAAGTTGACT CAGTTTTCCC
2281 AGTCAAACAT GTGTCTCCAG TCACTGTGAA CAAAGCTATA TTAAGGTACA TCATTCAAGG
2341 ACTTCATCCT TTCAGCACTG TTGATCTGCC ATCATTTAAA GAGCTGATTA GTACACTGCA
2401 GCCTGGCATT TCTGTCATTA CAAGGCCTAC TTTACGCTCC AAGATAGCTG AAGCTGCTCT
2461 GATCATGAAA CAGAAAGTGA CTGCTGCCAT GAGTGAAGTT GAATGGATTG CAACCACAAC
2521 GGATTGTTGG ACTGCACGTA GAAAGTCATT CATTGGTGTA ACTGCTCACT GGATCAACCC
2581 TGGAAGTCTT GAAAGACATT CCGCTGCACT TGCCTGCAAA AGATTAATGG GCTCTCATAC
2641 TTTTGAGGTA CTGGCCAGTG CCATGAATGA TATCCACTCA GAGTATGAAA TACGTGACAA
2701 GGTTGTTTGC ACAACCACAG ACAGTGGTTC CAACTTTATG AAGGCTTTCA GAGTTTTTGG
2761 TGTGGAAAAC AATGATATCG AGACTGAGGC AAGAAGGTGT GAAAGTGATG ACACTGATTC
2821 TGAAGGCTGT GGTGAGGGAA GTGATGGTGT GGAATTCCAA GATGCCTCAC GAGTCCTGGA
```

```
2881 CCAAGACGAT GGCTTCGAAT TCCAGCTACC AAAACATCAA AAGTGTGCCT GTCACTTACT

2941 TAACCTAGTC TCAAGCGTTG ATGCCCAAAA AGCTCTCTCA AATGAACACT ACAAGAAACT

3001 CTACAGATCT GTCTTTGGCA AATGCCAAGC TTTATGGAAT AAAAGCAGCC GATCGGCTCT

3061 AGCAGCTGAA GCTGTTGAAT CAGAAAGCCG GCTTCAGCTT TTAAGGCCAA ACCAAACGCG

3121 GTGGAATTCA ACTTTTATGG CTGTTGACAG AATTCTTCAA ATTTGCAAAG AAGCAGGAGA

3181 AGGCGCACTT CGGAATATAT GCACCTCTCT TGAGGTTCCA ATGTAAGTGT TTTTCCCCTC

3241 TATCGATGTA AACAAATGTG GGTTGTTTTT GTTTAATACT CTTTGATTAT GCTGATTTCT

3301 CCTGTAGGTT TAATCCAGCA GAAATGCTGT TCTTGACAGA GTGGGCCAAC ACAATGCGTC

3361 CAGTTGCAAA AGTACTCGAC ATCTTGCAAG CGGAAACGAA TACACAGCTG GGGTGGCTGC

3421 TGCCTAGTGT CCATCAGTTA AGCTTGAAAC TTCAGCGACT CCACCATTCT CTCAGGTACT

3481 GTGACCCACT TGTGGATGCC CTACAACAAG GAATCCAAAC ACGATTCAAG CATATGTTTG

3541 AAGATCCTGA GATCATAGCA GCTGCCATCC TTCTCCCTAA ATTTCGGACC TCTTGGACAA

3601 ATGATGAAAC CATCATAAAA CGAGGTAAAT GAATGCAAGC AACATACACT TGACGAATTC

3661 TAATCTGGGC AACCTTTGAG CCATACCAAA ATTATTCTTT TATTTATTTA TTTTTGCACT

3721 TTTTAGGAAT GTTATATCCC ATCTTTGGCT GTGATCTCAA TATGAATATT GATGTAAAGT

3781 ATTCTTGCAG CAGGTTGTAG TTATCCCTCA GTGTTTCTTG AAACCAAACT CATATGTATC

3841 ATATGTGGTT TGGAAATGCA GTTAGATTTT ATGCTAAAAT AAGGGATTTG CATGATTTTA

3901 GATGTAGATG ACTGCACGTA AATGTAGTTA ATGACAAAAT CCATAAAATT TGTTCCCAGT

3961 CAGAAGCCCC TCAACCAAAC TTTTCTTTGT GTCTGCTCAC TGTGCTTGTA GGCATGGACT

4021 ACATCAGAGT GCATCTGGAG CCTTTGGACC ACAAGAAGGA ATTGGCCAAC AGTTCATCTG

4081 ATGATGAAGA TTTTTTCGCT TCTTTGAAAC CGACAACACA TGAAGCCAGC AAAGAGTTGG

4141 ATGGATATCT GGCCTGTGTT TCAGACACCA GGGAGTCTCT GCTCACGTTT CCTGCTATTT

4201 GCAGCCTCTC TATCAAGACT AATACACCTC TTCCCGCATC GGCTGCCTGT GAGAGGCTTT

4261 TCAGCACTGC AGGATTGCTT TTCAGCCCCA AAAGAGCTAG GCTTGACACT AACAATTTTG

4321 AGAATCAGCT TCTACTGAAG TTAAATCTGA GGTTTTACAA CTTTGAGTAG CGTGTACTGG

4381 CATTAGATTG TCTGTCTTAT AGTTTGATAA TTAAATACAA ACAGTTCTAA AGCAGGATAA

4441 AACCTTGTAT GCATTTCATT TAATGTTTTT TGAGATTAAA AGCTTAAACA AGAATCTCTA

4501 GTTTTCTTTC TTGCTTTTAC TTTTACTTCC TTAATACTCA AGTACAATTT TAATGGAGTA

4561 CTTTTTTACT TTTACTCAAG TAAGATTCTA GCCAGATACT TTTACTTTTA ATTGAGTAAA

4621 ATTTTCCCTA AGTACTTGTA CTTTCACTTG AGTAAAATTT TTGAGTACTT TTTACACCTC

4681 TG.
```

The DNA insert should be operatively linked to an appropriate promoter. The expression constructs will further contain sites for transcription initiation, termination and, in the transcribed region, a ribosome binding site for translation. The coding portion of the mature transcripts expressed by the constructs will preferably include a translation initiating at the beginning and a termination codon (e.g., UAA, UGA or UAG) appropriately positioned at the end of the mRNA to be translated, with UAA and UAG preferred for mammalian or eukaryotic cell expression.

Expression vectors will preferably but optionally include at least one selectable marker. Such markers include, e.g., but are not limited to, ampicillin, zeocin (Sh bla gene), puromycin (pac gene), hygromycin B (hygB gene), G418/Geneticin (neo gene), mycophenolic acid, or glutamine synthetase (GS, U.S. Pat. Nos. 5,122,464; 5,770,359; 5,827,739), blasticidin (bsd gene), resistance genes for eukaryotic cell culture as well as ampicillin, zeocin (Sh bla gene), puromycin (pac gene), hygromycin B (hygB gene), G418/Geneticin (neo gene), kanamycin, spectinomycin, streptomycin, carbenicillin, bleomycin, erythromycin, polymyxin B, or tetracycline resistance genes for culturing in *E. coli* and other bacteria or prokaryotics (the above patents are entirely incorporated hereby by reference). Appropriate culture mediums and conditions for the above-described host cells are known in the art. Suitable vectors will be readily apparent to the skilled artisan. Introduction of a vector construct into a host cell can be effected by calcium phosphate transfection, DEAE-dextran mediated transfection, cationic lipid-mediated transfection, electroporation, transduction, infection or other known methods. Such methods are described in the art, such as Sambrook, supra, Chapters 1-4 and 16-18; Ausubel, supra, Chapters 1, 9, 13, 15, 16.

Expression vectors will preferably but optionally include at least one selectable cell surface marker for isolation of cells modified by the compositions and methods of the disclosure. Selectable cell surface markers of the disclosure comprise surface proteins, glycoproteins, or group of proteins that distinguish a cell or subset of cells from another defined subset of cells. Preferably the selectable cell surface marker distinguishes those cells modified by a composition or method of the disclosure from those cells that are not modified by a composition or method of the disclosure. Such cell surface markers include, e.g., but are not limited to, "cluster of designation" or "classification determinant" proteins (often abbreviated as "CD") such as a truncated or full length form of CD19, CD271, CD34, CD22, CD20, CD33, CD52, or any combination thereof. Cell surface markers further include the suicide gene marker RQR8 (Philip B et al. Blood. 2014 Aug. 21; 124(8):1277-87).

Expression vectors will preferably but optionally include at least one selectable drug resistance marker for isolation of cells modified by the compositions and methods of the disclosure. Selectable drug resistance markers of the disclosure may comprise wild-type or mutant Neo, DHFR, TYMS, FRANCF, RAD51C, GCS, MDR1, ALDH1, NKX2.2, or any combination thereof.

At least one inducible polypeptide of the disclosure can be expressed in a modified form, such as a fusion protein, and can include additional heterologous functional regions. For instance, a region of additional amino acids, particularly charged amino acids, can be added to the N-terminus of a protein scaffold to improve stability and persistence in the host cell, during purification, or during subsequent handling and storage. Also, peptide moieties can be added to a protein scaffold of the disclosure to facilitate purification. Such regions can be removed prior to final preparation of an inducible polypeptide or at least one fragment thereof. Such methods are described in many standard laboratory manuals, such as Sambrook, supra, Chapters 17.29-17.42 and 18.1-18.74; Ausubel, supra, Chapters 16, 17 and 18.

Those of ordinary skill in the art are knowledgeable in the numerous expression systems available for expression of a nucleic acid encoding a protein of the disclosure. Alternatively, nucleic acids of the disclosure can be expressed in a host cell by turning on (by manipulation) in a host cell that contains a sequence encoding an inducible polypeptide of the disclosure. Such methods are well known in the art, e.g., as described in U.S. Pat. Nos. 5,580,734, 5,641,670, 5,733,746, and 5,733,761, entirely incorporated herein by reference.

Expression vectors for modified cells can include one or more of the following expression control sequences, such as, but not limited to, an origin of replication; a promoter (e.g., late or early SV40 promoters, the CMV promoter (U.S. Pat. Nos. 5,168,062; 5,385,839), an HSV tk promoter, a pgk (phosphoglycerate kinase) promoter, an EF-1 alpha promoter (U.S. Pat. No. 5,266,491), at least one human promoter; an enhancer, and/or processing information sites, such as ribosome binding sites, RNA splice sites, polyadenylation sites (e.g., an SV40 large T Ag poly A addition site), and transcriptional terminator sequences. See, e.g., Ausubel et al., supra; Sambrook, et al., supra. Other cells useful for production of nucleic acids or proteins of the present invention are known and/or available, for instance, from the American Type Culture Collection Catalogue of Cell Lines and Hybridomas (www.atcc.org) or other known or commercial sources.

When eukaryotic host cells are employed, polyadenlyation or transcription terminator sequences are typically incorporated into the vector. An example of a terminator sequence is the polyadenlyation sequence from the bovine growth hormone gene. Sequences for accurate splicing of the transcript can also be included. An example of a splicing sequence is the VP1 intron from SV40 (Sprague, et al., J. Virol. 45:773-781 (1983)). Additionally, gene sequences to control replication in the host cell can be incorporated into the vector, as known in the art.

Amino Acid Codes

The amino acids that make up protein scaffolds of the disclosure are often abbreviated. The amino acid designations can be indicated by designating the amino acid by its single letter code, its three letter code, name, or three nucleotide codon(s) as is well understood in the art (see Alberts, B., et al., Molecular Biology of The Cell, Third Ed., Garland Publishing, Inc., New York, 1994). An inducible polypeptide of the disclosure can include one or more amino acid substitutions, deletions or additions, either from natural mutations or human manipulation, as specified herein. Amino acids in an inducible polypeptide of the disclosure that are essential for function can be identified by methods known in the art, such as site-directed mutagenesis or alanine-scanning mutagenesis (e.g., Ausubel, supra, Chapters 8, 15; Cunningham and Wells, Science 244:1081-1085 (1989)). The latter procedure introduces single alanine mutations at every residue in the molecule. The resulting mutant molecules are then tested for biological activity, such as, but not limited to, at least one neutralizing activity. Sites that are critical for function (i.e., inducing apoptosis) can also be identified by structural analysis, such as crystallization, nuclear magnetic resonance or photoaffinity labeling (Smith, et al., J. Mol. Biol. 224:899-904 (1992) and de Vos, et al., Science 255:306-312 (1992)).

Biologically active an inducible polypeptide of the disclosure include one or more proteins or enzymes (e.g. a caspase such as caspase 9) capable of inducing apoptosis in a cell with an efficacy that is at least 20%, 30%, or 40%, and, preferably, at least 50%, 60%, or 70%, and, most preferably, at least 80%, 90%, or 95%-99% or more efficacious as expression or induction of the cell's native (non-synthetic), endogenous or related and known protein or enzyme. Methods of assaying and quantifying measures of protein binding and enzymatic activity are well known to those of skill in the art.

Infusion of Modified Cells as Adoptive Cell Therapy

The disclosure provides modified cells that express one or more inducible polypeptide of the disclosure that have been selected for administration to a subject in need thereof. Modified cells of the disclosure may be formulated for storage at any temperature including room temperature and body temperature. Modified cells of the disclosure may be formulated for cryopreservation and subsequent thawing. Modified cells of the disclosure may be formulated in a pharmaceutically acceptable carrier for direct administration to a subject from sterile packaging.

EXAMPLES

Example 1: Expression and Function of PiggyBac Integrated iC9 Safety Switch into Human Pan T-Cells Human pan T-cells were nucleofected using an Amaxa 4D nucleofector with one of four piggyBac transposons. Modified T cells receiving the "mock" condition were nucleofected with an empty piggyBac transposon. Modified T cells received either a piggyBac transposase containing a therapeutic agent alone (a sequence encoding a CARTyrin) or a piggyBac transposase containing an integrated iC9 sequence and a therapeutic agent (a sequence encoding a CARTyrin).

FIG. 1 provides a schematic diagram of the iC9 safety switch, which contains a ligand binding region, a linker, and a truncated caspase 9 polypeptide. Specifically, the iC9 polypeptide contains a ligand binding region comprising a FK506 binding protein 12 (FKBP12) polypeptide including a substitution of valine (V) for phenylalanine (F) at position 36 (F36V). The FKBP12 polypeptide of the iC9 polypeptide is encoded by an amino acid sequence comprising GVQVETISPGDGRTFPKRGQTCVVHYTGMLED GKKVDSSRDRNKPFKFMLGKQEVIRG WEEGVAQMSVGQRAKLTISPDYAYGATGHPGIIP-PHATLVFDVELLKLE (SEQ ID NO: 3). The FKBP12 polypeptide of the iC9 polypeptide is encoded by a nucleic acid sequence comprising GGGGTCCAGGTCGAGACT-ATTTCACCAGGGGATGGGCGAACATTTC-CAAAAAGGGG CCAGACTTGCGTCGTGCATTA-CACCGGGATGCTGGAGGACGGGAAGAAAG TGGACA GCTCCAGGGATCGCAACAAGCCCTT-CAAGTTCATGCTGGGAAAGCAGGAAGTGATC CGAGGATGGGAGGAAGGCGTGGCACA-GATGTCAGTCGGCCAGCGGGCCAAACTGA CCATT-AGCCCTGACTACGCTTATGGAGCAACAGGC-CACCCAGGGATCATTCCCCCTC ATGCCACCCTGGTCTTCGATGTGGAACTGCT-GAAGCTGGAG (SEQ ID NO: 4). The linker region of the iC9 polypeptide is encoded by an amino acid comprising GGGGS (SEQ ID NO: 5) and a nucleic acid sequence comprising GGAGGAGGAGGATCC (SEQ ID NO: 6). The amino acid sequence encoding the iC9 polypeptide is encoded by an amino acid comprising GFGDV-GALESLRGNADLAYILSMEPCGHCLIINNVNFCRES GLRTRTGSNIDCEKLRRRFSSLHFMVEVKGDL-TAKKMVLALLELAQQDHGALDCCVVV ILSHGCQASHLQFPGAVYGTDGCPVS-VEKIVNIFNGTSCPSLGGKPKLFFIQACGGEQKD HGFEVASTSPEDESPGSNPEPDATPFQEGLRTFDQL-DAISSLPTPSDIFVSYSTFPGFVSWR DPKSGSWYVETLDDIFEQWAHSEDLQSLLLRVA-NAVSVKGIYKQMPGCFNFLRKKLFF KTS (SEQ ID NO: 7). The nucleic acid sequence encoding the iC9 polypeptide is encoded by a nucleic acid sequence comprising (SEQ ID NO: 8)
TTTGGGGACGTGGGGGCCCTGGAGTCTCTGCGAGGAAATGCCGATCTGG

CTTACATCCTGAGCATGGAACCCTGCGGCCACTGTCTGATCATTAACAA

TGTGAACTTCTGCAGAGAAAGCGGACTGCGAACACGGACTGGCTCCAAT

ATTGACTGTGAGAAGCTGCGGAGAAGGTTCTCTAGTCTGCACTTTATGG

TCGAAGTGAAAGGGGATCTGACCGCCAAGAAAATGGTGCTGGCCCTGCT

GGAGCTGGCTCAGCAGGACCATGGAGCTCTGGATTGCTGCGTGGTCGTG

ATCCTGTCCCACGGGTGCCAGGCTTCTCATCTGCAGTTCCCCGGAGCAG

TGTACGGAACAGACGGCTGTCCTGTCAGCGTGGAGAAGATCGTCAACAT

CTTCAACGGCACTTCTTGCCCTAGTCTGGGGGGAAAGCCAAAACTGTTC

TTTATCCAGGCCTGTGGCGGGGAACAGAAAGATCACGGCTTCGAGGTGG

-continued
CCAGCACCAGCCCTGAGGACGAATCACCAGGGAGCAACCCTGAACCAGA

TGCAACTCCATTCCAGGAGGGACTGAGGACCTTTGACCAGCTGGATGCT

ATCTCAAGCCTGCCCACTCCTAGTGACATTTTCGTGTCTTACAGTACCT

TCCCAGGCTTTGTCTCATGGCGCGATCCCAAGTCAGGGAGCTGGTACGT

GGAGACACTGGACGACATCTTTGAACAGTGGGCCCATTCAGAGGACCTG

CAGAGCCTGCTGCTGCGAGTGGCAAACGCTGTCTCTGTGAAGGGCATCT

ACAAACAGATGCCCGGGTGCTTCAATTTTCTGAGAAAGAAACTGTTCTT

TAAGACTTCC.

To test the iC9 safety switch, each of the four modified T cells were incubated for 24 hours with 0, 0.1 nM, 1 nM, 10 nM, 100 nM or 1000 nM AP1903 (an induction agent for AP1903, also known as Rimiducid). Viability was assessed by flow cytometry using 7-aminoactinomycin D (7-AAD), a fluorescent intercalator, as a marker for cells undergoing apoptosis.

Figure 2:
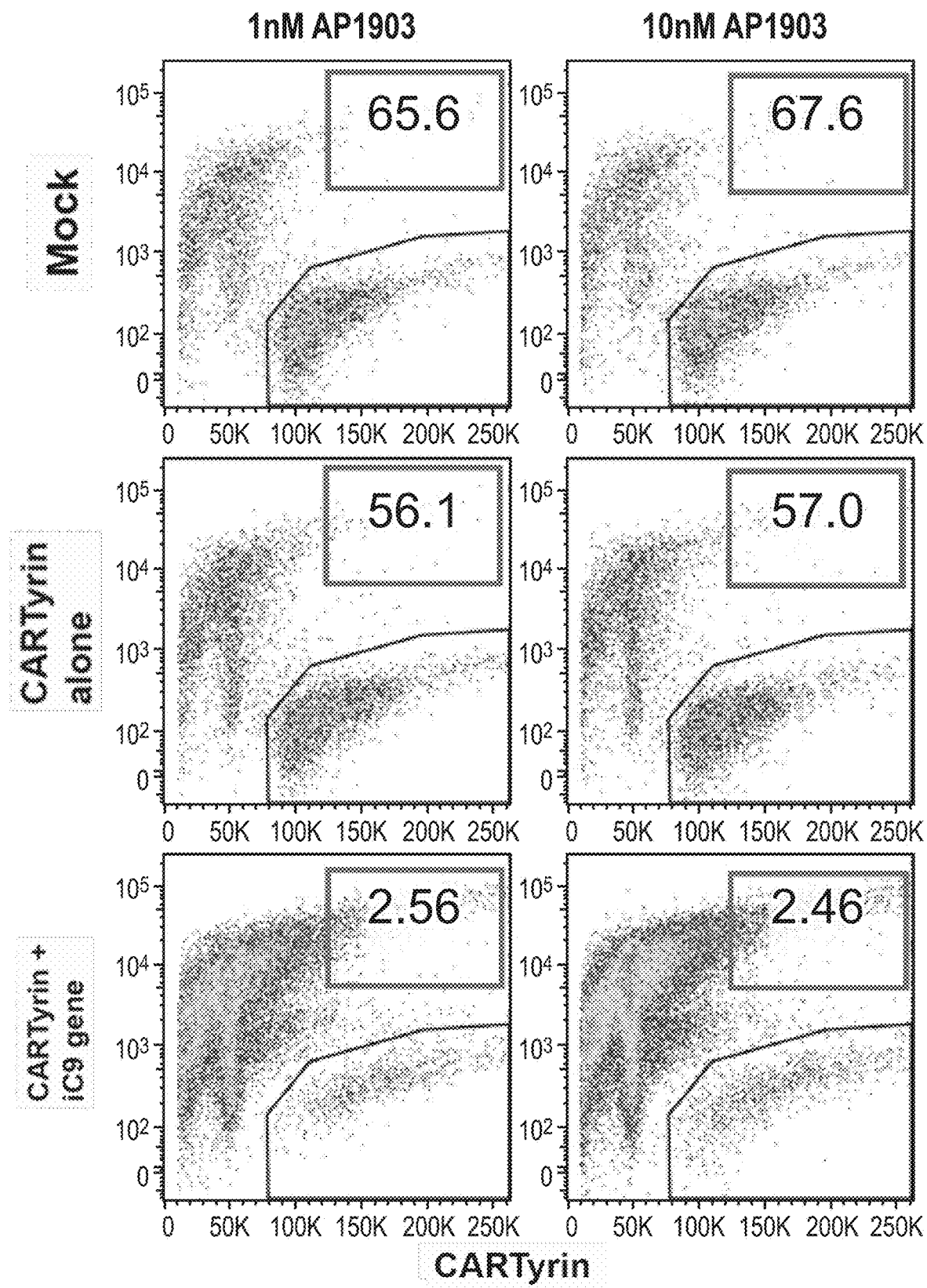
FIG. 2 is a series of flow cytometry plots depicting the abundance of cells moving from an area of live cells (the gated lower right quadrant) to an area populated by apoptotic cells (the upper left quadrant) as a function of increasing dosage of the induction agent (AP1903, also called Rimiducid) in cells modified to express a therapeutic agent (a CARTyrin) alone or in combination with an inducible caspase polypeptide of the disclosure (encoded by an iC9 construct (also known as a "safety switch") introduced into cells by a piggyBac (PB) transposase) at day 12 post nucleofection.
Figure 2:
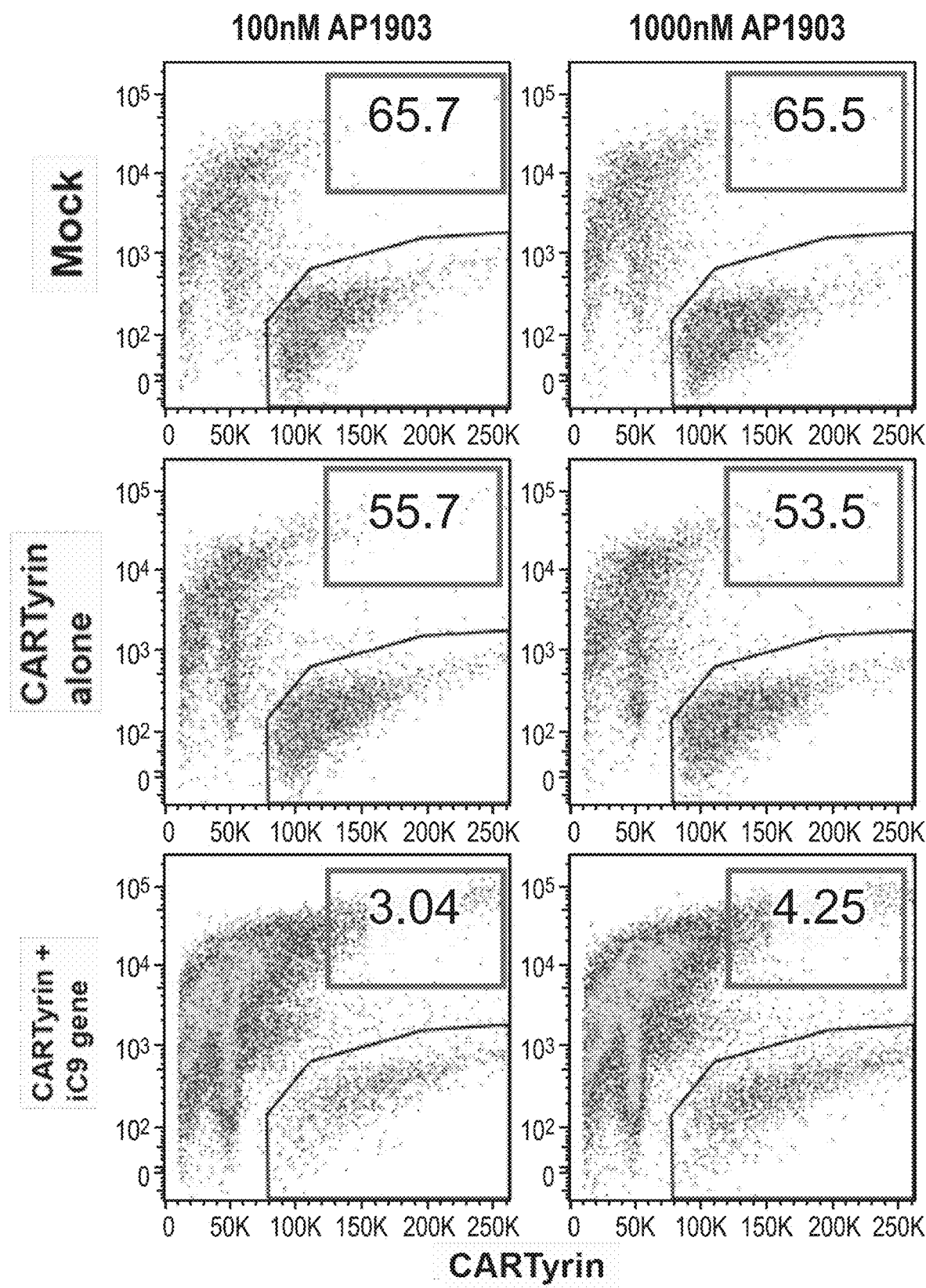
Figure 2:
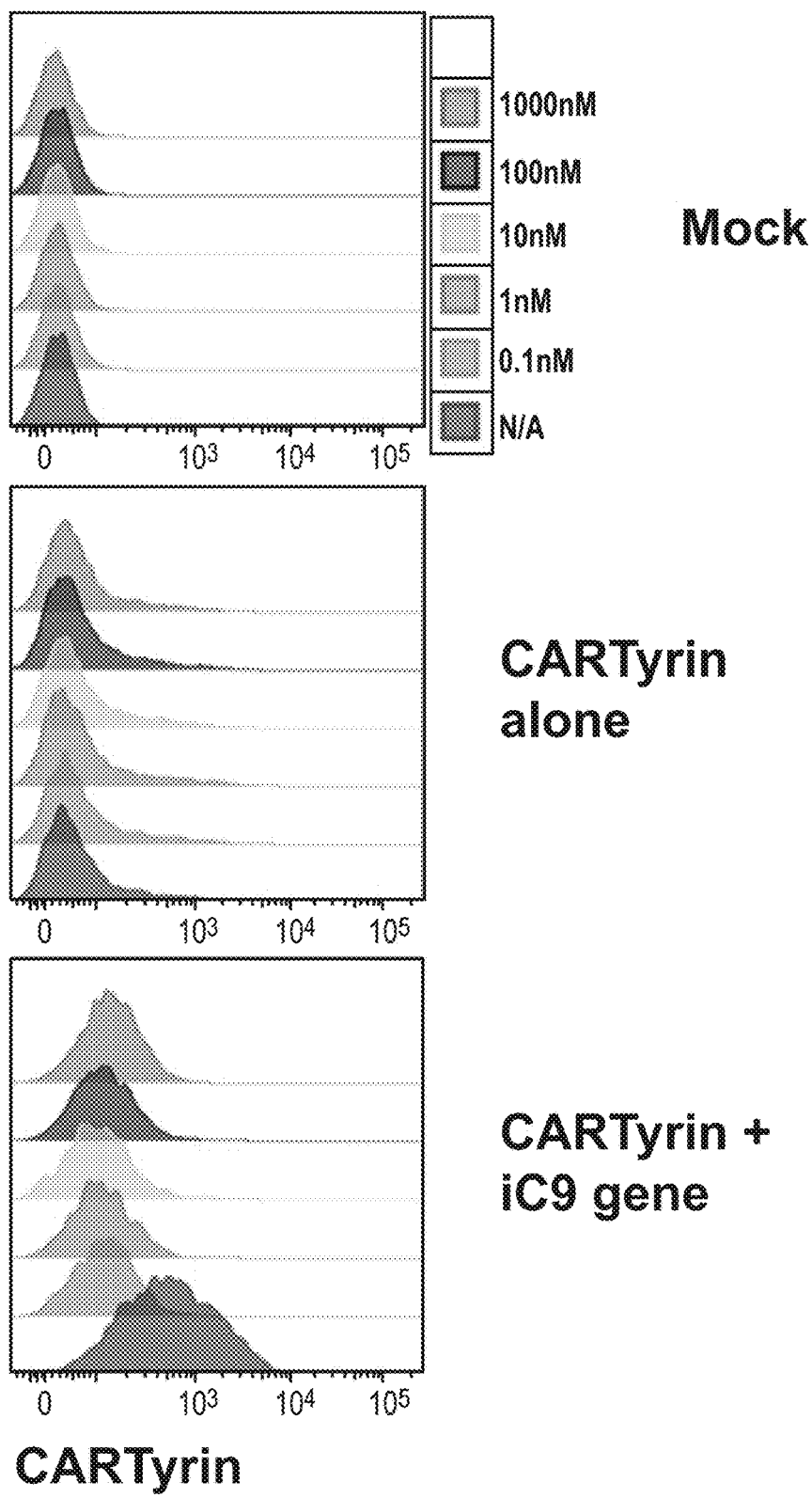

Cell viability was assessed at day 12 (see FIG. 2). The data demonstrate a shift of cell populations from the lower right to the upper left quadrants with increasing concentration of the induction agent in cells containing the iC9 construct; however, this effect is not observed in cells lacking the iC9 construct (those receiving only the CAR-Tyrin), in which cells are evenly distributed among these two areas regardless of the concentration of the induction agent. Moreover, cell viability was assessed at day 19 (see FIG. 3). The data reveal the same trend as shown in FIG. 2 (day 12 post-nucleofection); however, the population shift to the upper left quadrant is more pronounced at this later time point (day 19 post-nucleofection).

Figure 3:
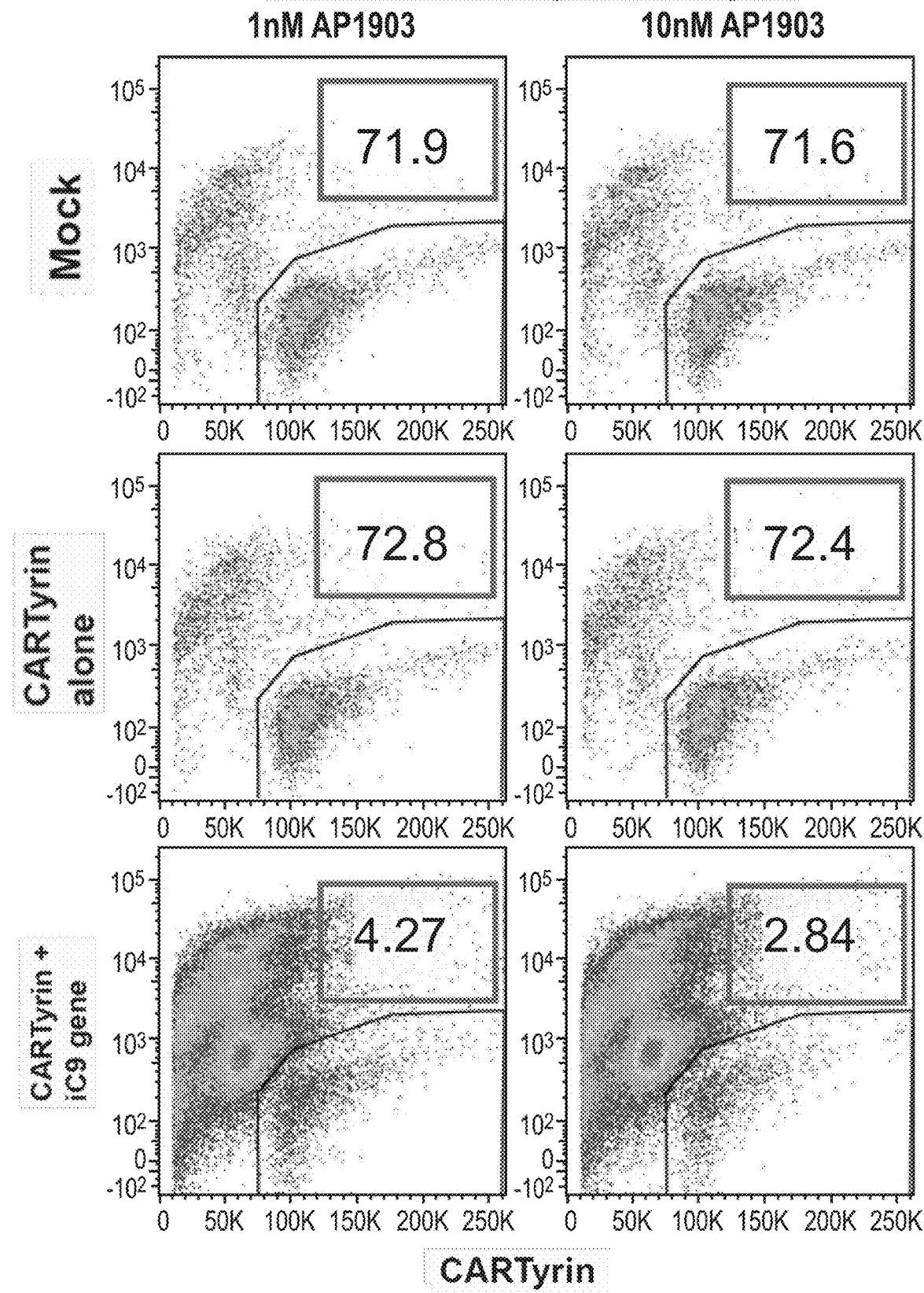
FIG. 3 is a series of flow cytometry plots depicting the abundance of cells moving from an area of live cells (the gated lower right quadrant) to an area populated by apoptotic cells (the upper left quadrant) as a function of increasing dosage of the induction agent (AP1903, also called Rimiducid) in cells modified to express a therapeutic agent (a CARTyrin) alone or in combination with an inducible caspase polypeptide of the disclosure (encoded by an iC9 construct (also known as a "safety switch") introduced into cells by a piggyBac (PB) transposase) at day 19 post nucleofection.
Figure 3:
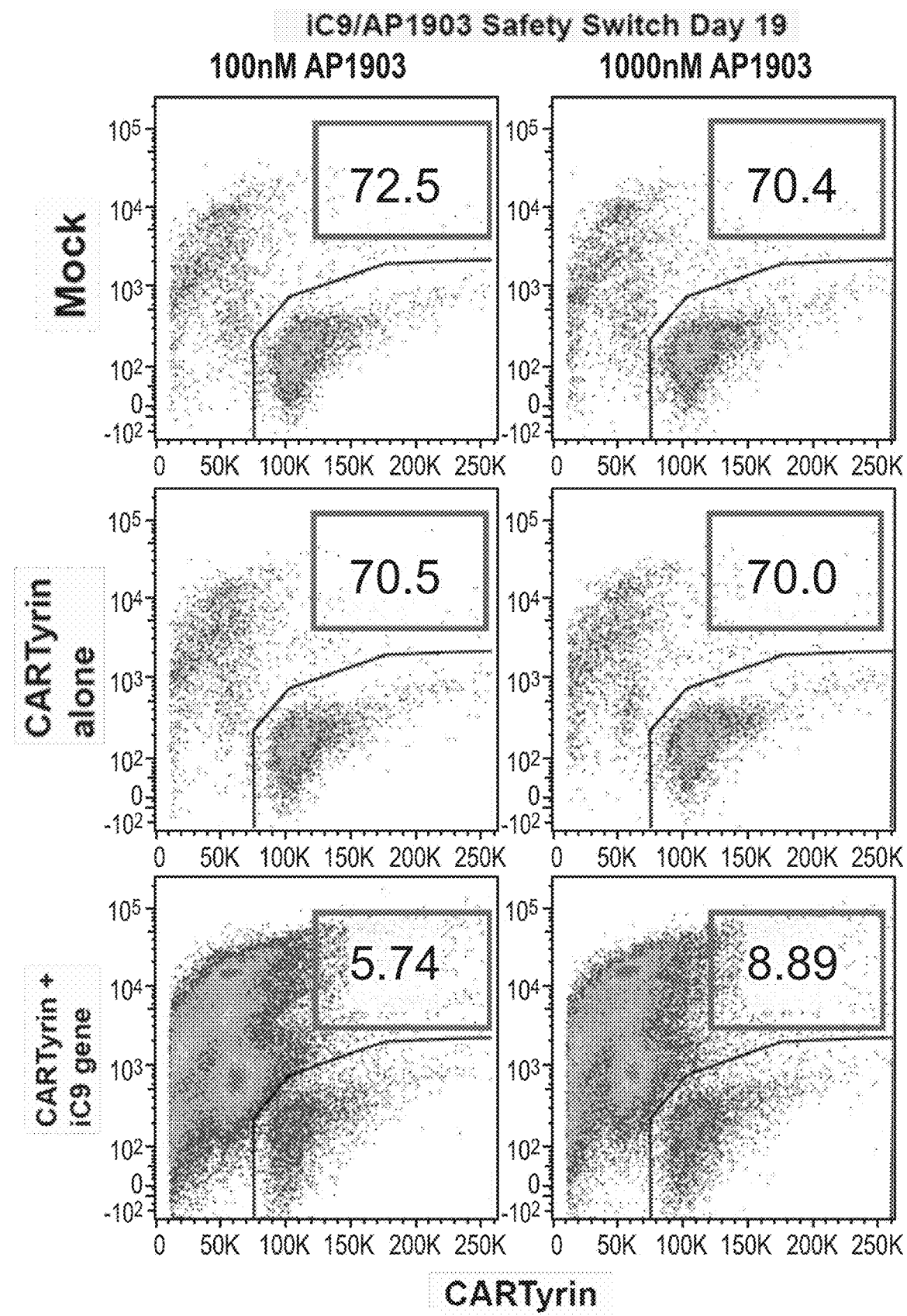
Figure 3:
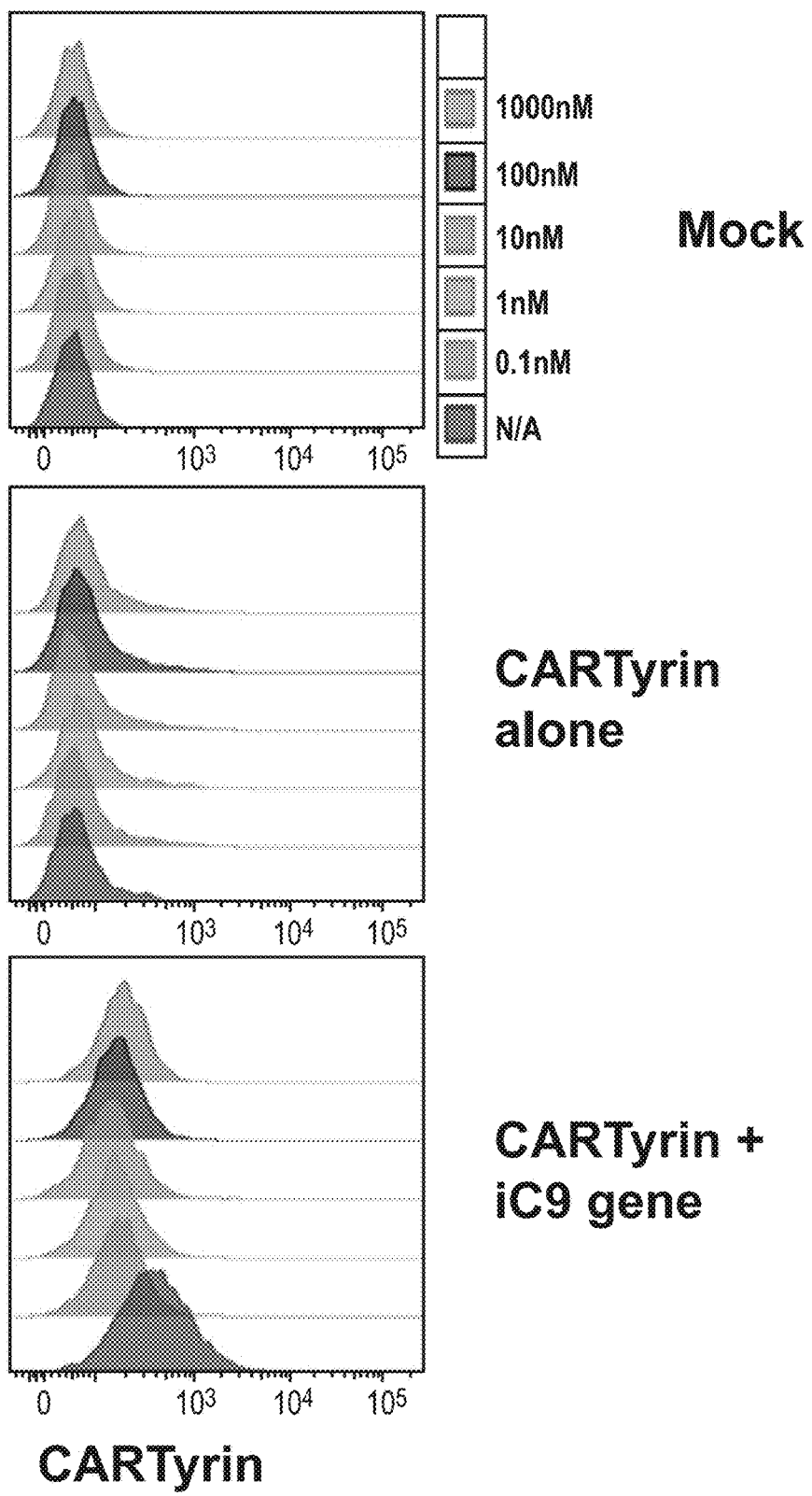
Figure 4:
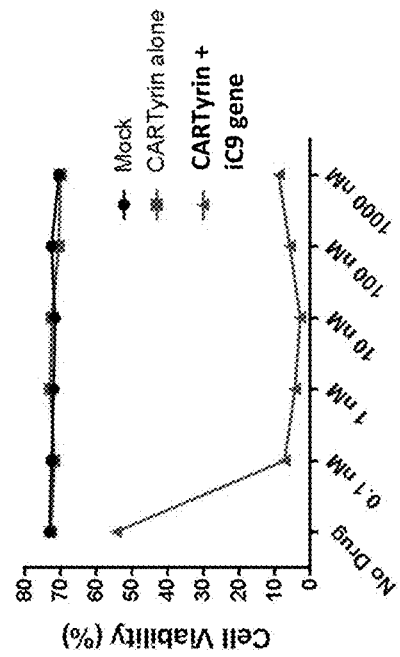
FIG. 4 is a pair of graphs depicting a quantification of the aggregated results shown either in FIG. 2 (left graph) or FIG. 3 (right graph). Specifically, these graphs show the impact of the iC9 safety switch on the percent cell viability as a function of the concentration of the induction agent (AP1903, also called Rimiducid) of the iC9 switch for each modified cell type at either day 12 (FIG. 2 and left graph) or day 19 (FIG. 3 and right graph).
Figure 4:
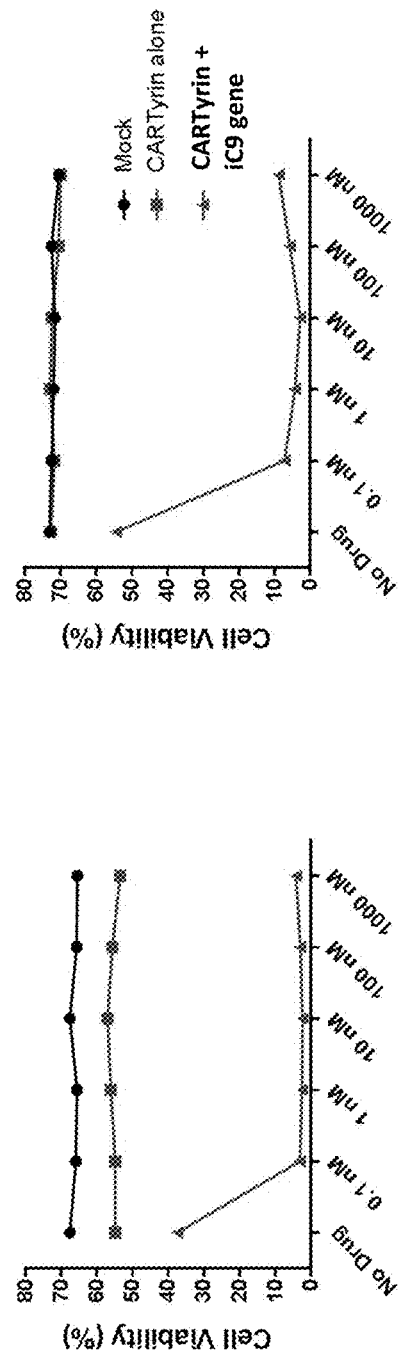

A quantification of the aggregated results was performed and is provided in FIG. 4, showing the significant impact of the iC9 safety switch on the percent cell viability as a function of the concentration of the induction agent (AP1903, also known as Rimiducid) of the iC9 switch for each modified cell type at either day 12 (FIG. 2 and left graph) or day 19 (FIG. 3 and right graph). The presence of the iC9 safety switch induces apoptosis in a significant majority of cells by day 12 and the effect is even more dramatic by day 19.

The results of this study show that the iC9 safety switch is extremely effective at eliminating active cells upon contact with an induction agent (e.g. AP1903, also known as Rimiducid) because AP1903 (Rimiducid) induces apoptosis at even the lowest concentrations of the study (0.1 nM). Furthermore, the iC9 safety switch may be functionally expressed as part of a tricistronic vector.

Figure 5:
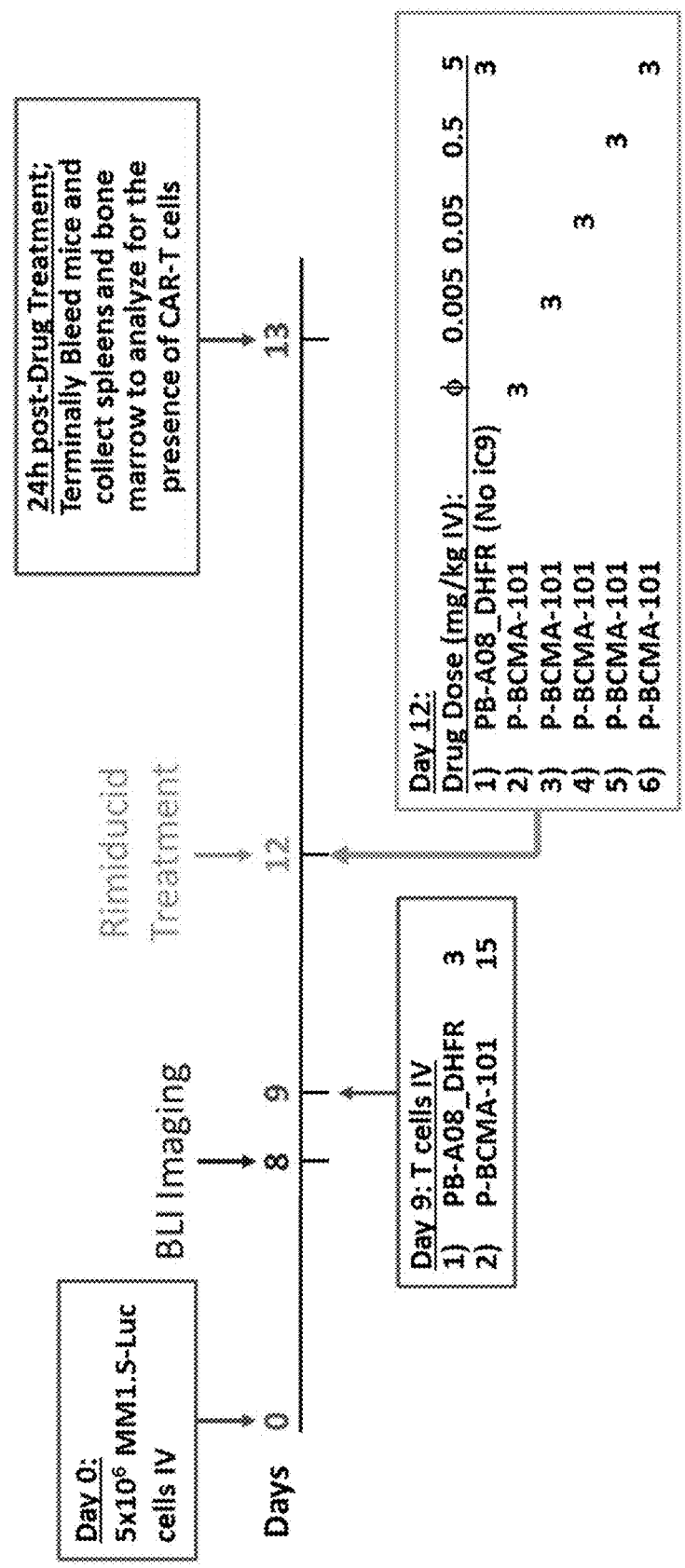
FIG. 5 is a diagram showing a study timeline and outline for an in vivo study. NSG mice were IV injected with MM.1S/luciferase$^+$ cells, staged at day 8, injected with T cells on day 9, and treated with AP1903 (Rimiducid) on day 12 at the indicated doses. 24 hours later, mice were euthanized and blood, spleen, and bone marrow cells were collected and stained for the presence of huCD45$^+$ cells.
Figure 6:
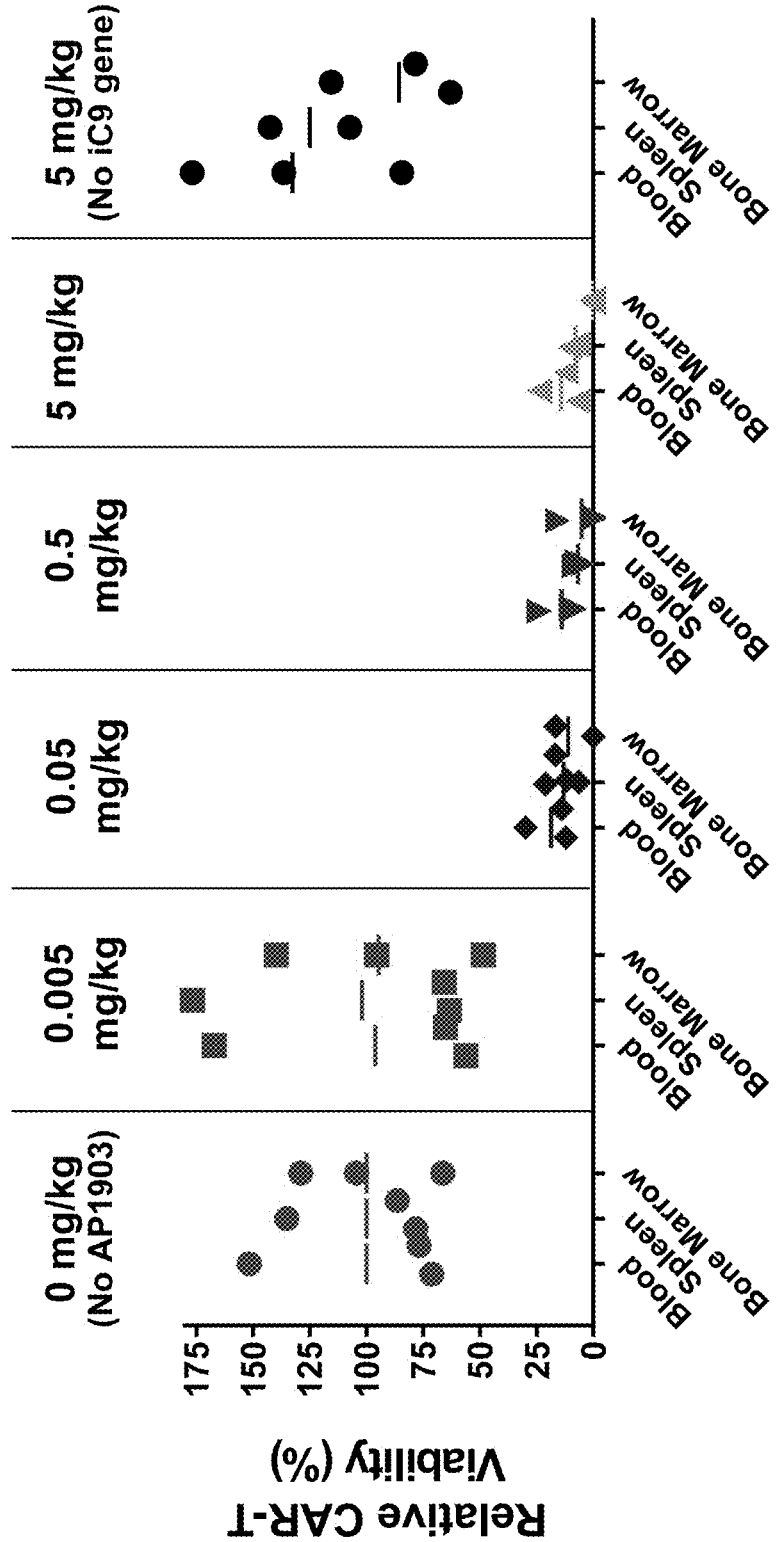
FIG. 6 is a graph demonstrating the highly efficient killing of cells comprising P-BCMA-101 using Rimiducid (AP1903) in vivo.

Example 2: Highly Efficient Killing of Cells Comprising P-BCMA-101 Using the iC9 Safety Switch in NGS Mice In Vivo NSG mice were IV injected with MM.1S/luciferase$^+$ cells, staged at day 8, injected with T cells on day 9, and treated with AP1903 (Rimiducid) on day 12 at the indicated doses. 24 hours later, mice were euthanized and blood, spleen, and bone marrow cells were collected and stained for the presence of huCD45$^+$ cells (FIG. 5). Blood, spleen, and bone marrow cells were analyzed by flow cytometry for the presence of huCD45$^+$ cells. The relative viability was determined by dividing the number of huCD45 cells by the number of msCD45 cells and normalizing to the average of huCD45/msCD45 in the no treatment group times, 100% per 1,500 bead events for each sample. Each data point represents a different mouse (FIG. 6).

INCORPORATION BY REFERENCE

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

Other Embodiments

While particular embodiments of the disclosure have been illustrated and described, various other changes and modifications can be made without departing from the spirit and scope of the disclosure. The scope of the appended claims includes all such changes and modifications that are within the scope of this disclosure.

What is claimed is:

1. A polynucleotide comprising the nucleic acid sequence of SEQ ID NO: 10.

2. A transposon comprising the polynucleotide of claim 1.

3. The transposon of claim 2, further comprising a nucleic acid sequence encoding a therapeutic protein.

4. The transposon of claim 3, wherein the therapeutic protein comprises an antigen receptor, a cell surface protein, a membrane-bound protein, an extracellular membrane-bound protein, an intracellular membrane-bound protein, an intracellular protein, a nuclear localized protein, a nuclear protein, a cytoplasmic protein, a cytosolic protein, a secreted protein, a lysosomal protein, an endosomal protein, a vesicle-associated protein, a mitochondrial protein, an endoplasmic reticulum protein, a cytoskeletal protein, a protein involved in intracellular signaling, a protein involved in extracellular signaling, or any combination thereof.

5. The transposon of claim 4, wherein the antigen receptor comprises a T-Cell Receptor (TCR) or a Chimeric Antigen Receptor (CAR).

6. The transposon of claim 2, wherein the transposon is a piggyBac transposon, a Sleeping Beauty transposon, a Helraiser transposon, or Tol2 transposon.

7. A vector comprising the polynucleotide of claim 1.

8. A cell comprising the polynucleotide of claim 1.

9. The cell of claim 8, wherein the cell is a human cell, an immune cell, an artificial antigen presenting cell, a stem cell, or any combination thereof.

10. A composition comprising the cell of claim 9.

* * * * *

SEQUENCE LISTING

```
<160> NUMBER OF SEQ ID NOS: 25

<210> SEQ ID NO 1
<211> LENGTH: 594
<212> TYPE: PRT
<213> ORGANISM: Trichoplusia ni

<400> SEQUENCE: 1

Met Gly Ser Ser Leu Asp Asp Glu His Ile Leu Ser Ala Leu Leu Gln
1               5                   10                  15

Ser Asp Asp Glu Leu Val Gly Glu Asp Ser Asp Ser Glu Ile Ser Asp
            20                  25                  30

His Val Ser Glu Asp Asp Val Gln Ser Asp Thr Glu Glu Ala Phe Ile
        35                  40                  45

Asp Glu Val His Glu Val Gln Pro Thr Ser Ser Gly Ser Glu Ile Leu
    50                  55                  60

Asp Glu Gln Asn Val Ile Glu Gln Pro Gly Ser Ser Leu Ala Ser Asn
65                  70                  75                  80

Arg Ile Leu Thr Leu Pro Gln Arg Thr Ile Arg Gly Lys Asn Lys His
                85                  90                  95

Cys Trp Ser Thr Ser Lys Ser Thr Arg Arg Ser Arg Val Ser Ala Leu
            100                 105                 110

Asn Ile Val Arg Ser Gln Arg Gly Pro Thr Arg Met Cys Arg Asn Ile
        115                 120                 125

Tyr Asp Pro Leu Leu Cys Phe Lys Leu Phe Phe Thr Asp Glu Ile Ile
    130                 135                 140

Ser Glu Ile Val Lys Trp Thr Asn Ala Glu Ile Ser Leu Lys Arg Arg
145                 150                 155                 160

Glu Ser Met Thr Gly Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
            180                 185                 190

His Met Ser Thr Asp Asp Leu Phe Asp Arg Ser Leu Ser Met Val Tyr
        195                 200                 205

Val Ser Val Met Ser Arg Asp Arg Phe Asp Phe Leu Ile Arg Cys Leu
    210                 215                 220

Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
                245                 250                 255

Gln Asn Tyr Thr Pro Gly Ala His Leu Thr Ile Asp Glu Gln Leu Leu
            260                 265                 270
```

Gly Phe Arg Gly Arg Cys Pro Phe Arg Met Tyr Ile Pro Asn Lys Pro
            275                 280                 285

Ser Lys Tyr Gly Ile Lys Ile Leu Met Met Cys Asp Ser Gly Thr Lys
        290                 295                 300

Tyr Met Ile Asn Gly Met Pro Tyr Leu Gly Arg Gly Thr Gln Thr Asn
305                 310                 315                 320

Gly Val Pro Leu Gly Glu Tyr Val Lys Glu Leu Ser Lys Pro Val
                325                 330                 335

His Gly Ser Cys Arg Asn Ile Thr Cys Asp Asn Trp Phe Thr Ser Ile
            340                 345                 350

Pro Leu Ala Lys Asn Leu Leu Gln Glu Pro Tyr Lys Leu Thr Ile Val
        355                 360                 365

Gly Thr Val Arg Ser Asn Lys Arg Glu Ile Pro Glu Val Leu Lys Asn
370                 375                 380

Ser Arg Ser Arg Pro Val Gly Thr Ser Met Phe Cys Phe Asp Gly Pro
385                 390                 395                 400

Leu Thr Leu Val Ser Tyr Lys Pro Lys Pro Ala Lys Met Val Tyr Leu
                405                 410                 415

Leu Ser Ser Cys Asp Glu Asp Ala Ser Ile Asn Glu Ser Thr Gly Lys
            420                 425                 430

Pro Gln Met Val Met Tyr Tyr Asn Gln Thr Lys Gly Gly Val Asp Thr
        435                 440                 445

Leu Asp Gln Met Cys Ser Val Met Thr Cys Ser Arg Lys Thr Asn Arg
450                 455                 460

Trp Pro Met Ala Leu Leu Tyr Gly Met Ile Asn Ile Ala Cys Ile Asn
465                 470                 475                 480

Ser Phe Ile Ile Tyr Ser His Asn Val Ser Ser Lys Gly Glu Lys Val
                485                 490                 495

Gln Ser Arg Lys Lys Phe Met Arg Asn Leu Tyr Met Ser Leu Thr Ser
            500                 505                 510

Ser Phe Met Arg Lys Arg Leu Glu Ala Pro Thr Leu Lys Arg Tyr Leu
        515                 520                 525

Arg Asp Asn Ile Ser Asn Ile Leu Pro Asn Glu Val Pro Gly Thr Ser
530                 535                 540

Asp Asp Ser Thr Glu Glu Pro Val Met Lys Lys Arg Thr Tyr Cys Thr
545                 550                 555                 560

Tyr Cys Pro Ser Lys Ile Arg Arg Lys Ala Asn Ala Ser Cys Lys Lys
                565                 570                 575

Cys Lys Lys Val Ile Cys Arg Glu His Asn Ile Asp Met Cys Gln Ser
            580                 585                 590

Cys Phe

<210> SEQ ID NO 2
<211> LENGTH: 594
<212> TYPE: PRT
<213> ORGANISM: Artificial Sequence
<220> FEATURE:
<223> OTHER INFORMATION: Super PiggyBac transposase

<400> SEQUENCE: 2

Met Gly Ser Ser Leu Asp Asp Glu His Ile Leu Ser Ala Leu Leu Gln
1               5                   10                  15

Ser Asp Asp Glu Leu Val Gly Glu Asp Ser Asp Ser Glu Val Ser Asp
            20                  25                  30

His Val Ser Glu Asp Asp Val Gln Ser Asp Thr Glu Glu Ala Phe Ile

```
                35                  40                  45
Asp Glu Val His Glu Val Gln Pro Thr Ser Ser Gly Ser Glu Ile Leu
 50                  55                  60

Asp Glu Gln Asn Val Ile Glu Gln Pro Gly Ser Ser Leu Ala Ser Asn
 65                  70                  75                  80

Arg Ile Leu Thr Leu Pro Gln Arg Thr Ile Arg Gly Lys Asn Lys His
                 85                  90                  95

Cys Trp Ser Thr Ser Lys Ser Thr Arg Arg Ser Arg Val Ser Ala Leu
                100                 105                 110

Asn Ile Val Arg Ser Gln Arg Gly Pro Thr Arg Met Cys Arg Asn Ile
                115                 120                 125

Tyr Asp Pro Leu Leu Cys Phe Lys Leu Phe Phe Thr Asp Glu Ile Ile
130                 135                 140

Ser Glu Ile Val Lys Trp Thr Asn Ala Glu Ile Ser Leu Lys Arg Arg
145                 150                 155                 160

Glu Ser Met Thr Ser Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
                180                 185                 190

His Met Ser Thr Asp Asp Leu Phe Asp Arg Ser Leu Ser Met Val Tyr
                195                 200                 205

Val Ser Val Met Ser Arg Asp Arg Phe Asp Phe Leu Ile Arg Cys Leu
210                 215                 220

Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
                245                 250                 255

Gln Asn Tyr Thr Pro Gly Ala His Leu Thr Ile Asp Glu Gln Leu Leu
                260                 265                 270

Gly Phe Arg Gly Arg Cys Pro Phe Arg Val Tyr Ile Pro Asn Lys Pro
                275                 280                 285

Ser Lys Tyr Gly Ile Lys Ile Leu Met Met Cys Asp Ser Gly Thr Lys
290                 295                 300

Tyr Met Ile Asn Gly Met Pro Tyr Leu Gly Arg Gly Thr Gln Thr Asn
305                 310                 315                 320

Gly Val Pro Leu Gly Glu Tyr Tyr Val Lys Glu Leu Ser Lys Pro Val
                325                 330                 335

His Gly Ser Cys Arg Asn Ile Thr Cys Asp Asn Trp Phe Thr Ser Ile
                340                 345                 350

Pro Leu Ala Lys Asn Leu Leu Gln Glu Pro Tyr Lys Leu Thr Ile Val
                355                 360                 365

Gly Thr Val Arg Ser Asn Lys Arg Glu Ile Pro Glu Val Leu Lys Asn
                370                 375                 380

Ser Arg Ser Arg Pro Val Gly Thr Ser Met Phe Cys Phe Asp Gly Pro
385                 390                 395                 400

Leu Thr Leu Val Ser Tyr Lys Pro Lys Pro Ala Lys Met Val Tyr Leu
                405                 410                 415

Leu Ser Ser Cys Asp Glu Asp Ala Ser Ile Asn Glu Ser Thr Gly Lys
                420                 425                 430

Pro Gln Met Val Met Tyr Tyr Asn Gln Thr Lys Gly Gly Val Asp Thr
                435                 440                 445

Leu Asp Gln Met Cys Ser Val Met Thr Cys Ser Arg Lys Thr Asn Arg
450                 455                 460
```

Trp Pro Met Ala Leu Leu Tyr Gly Met Ile Asn Ile Ala Cys Ile Asn
465                 470                 475                 480

Ser Phe Ile Ile Tyr Ser His Asn Val Ser Lys Gly Glu Lys Val
            485                 490                 495

Gln Ser Arg Lys Lys Phe Met Arg Asn Leu Tyr Met Ser Leu Thr Ser
                500                 505                 510

Ser Phe Met Arg Lys Arg Leu Glu Ala Pro Thr Leu Lys Arg Tyr Leu
            515                 520                 525

Arg Asp Asn Ile Ser Asn Ile Leu Pro Lys Glu Val Pro Gly Thr Ser
                530                 535                 540

Asp Asp Ser Thr Glu Glu Pro Val Met Lys Lys Arg Thr Tyr Cys Thr
545                 550                 555                 560

Tyr Cys Pro Ser Lys Ile Arg Arg Lys Ala Asn Ala Ser Cys Lys Lys
                565                 570                 575

Cys Lys Lys Val Ile Cys Arg Glu His Asn Ile Asp Met Cys Gln Ser
                580                 585                 590

Cys Phe

<210> SEQ ID NO 3
<211> LENGTH: 107
<212> TYPE: PRT
<213> ORGANISM: Artificial Sequence
<220> FEATURE:
<223> OTHER INFORMATION: FKBP12 derived polypeptide

<400> SEQUENCE: 3

Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Val Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Glu
            100                 105

<210> SEQ ID NO 4
<211> LENGTH: 321
<212> TYPE: DNA
<213> ORGANISM: Artificial Sequence
<220> FEATURE:
<223> OTHER INFORMATION: nucleic acid sequence encoding FKBP12 derived
      polypeptide

<400> SEQUENCE: 4
ggggtccagg tcgagactat ttcaccaggg gatgggcgaa catttccaaa aaggggccag      60
acttgcgtcg tgcattacac cgggatgctg gaggacggga agaaagtgga cagctccagg     120
gatcgcaaca agcccttcaa gttcatgctg ggaaagcagg aagtgatccg aggatgggag     180
gaaggcgtgg cacagatgtc agtcggccag cgggccaaac tgaccattag ccctgactac     240
gcttatggag caacaggcca cccagggatc attccccctc atgccaccct ggtcttcgat     300

-continued

```
gtggaactgc tgaagctgga g                                              321
```

<210> SEQ ID NO 5
<211> LENGTH: 5
<212> TYPE: PRT
<213> ORGANISM: Artificial Sequence
<220> FEATURE:
<223> OTHER INFORMATION: linker

<400> SEQUENCE: 5

Gly Gly Gly Gly Ser
1               5

<210> SEQ ID NO 6
<211> LENGTH: 15
<212> TYPE: DNA
<213> ORGANISM: Artificial Sequence
<220> FEATURE:
<223> OTHER INFORMATION: nucleic acid sequence encoding a linker

<400> SEQUENCE: 6

```
ggaggaggag gatcc                                                     15
```

<210> SEQ ID NO 7
<211> LENGTH: 282
<212> TYPE: PRT
<213> ORGANISM: Artificial Sequence
<220> FEATURE:
<223> OTHER INFORMATION: truncated caspase 9

<400> SEQUENCE: 7

Gly Phe Gly Asp Val Gly Ala Leu Glu Ser Leu Arg Gly Asn Ala Asp
1               5                   10                  15

Leu Ala Tyr Ile Leu Ser Met Glu Pro Cys Gly His Cys Leu Ile Ile
            20                  25                  30

Asn Asn Val Asn Phe Cys Arg Glu Ser Gly Leu Arg Thr Arg Thr Gly
        35                  40                  45

Ser Asn Ile Asp Cys Glu Lys Leu Arg Arg Arg Phe Ser Ser Leu His
    50                  55                  60

Phe Met Val Glu Val Lys Gly Asp Leu Thr Ala Lys Lys Met Val Leu
65                  70                  75                  80

Ala Leu Leu Glu Leu Ala Gln Gln Asp His Gly Ala Leu Asp Cys Cys
                85                  90                  95

Val Val Val Ile Leu Ser His Gly Cys Gln Ala Ser His Leu Gln Phe
            100                 105                 110

Pro Gly Ala Val Tyr Gly Thr Asp Gly Cys Pro Val Ser Val Glu Lys
        115                 120                 125

Ile Val Asn Ile Phe Asn Gly Thr Ser Cys Pro Ser Leu Gly Gly Lys
    130                 135                 140

Pro Lys Leu Phe Phe Ile Gln Ala Cys Gly Gly Glu Gln Lys Asp His
145                 150                 155                 160

Gly Phe Glu Val Ala Ser Thr Ser Pro Glu Asp Glu Ser Pro Gly Ser
                165                 170                 175

Asn Pro Glu Pro Asp Ala Thr Pro Phe Gln Glu Gly Leu Arg Thr Phe
            180                 185                 190

Asp Gln Leu Asp Ala Ile Ser Ser Leu Pro Thr Pro Ser Asp Ile Phe
        195                 200                 205

Val Ser Tyr Ser Thr Phe Pro Gly Phe Val Ser Trp Arg Asp Pro Lys
    210                 215                 220

```
Ser Gly Ser Trp Tyr Val Glu Thr Leu Asp Asp Ile Phe Glu Gln Trp
225                 230                 235                 240

Ala His Ser Glu Asp Leu Gln Ser Leu Leu Arg Val Ala Asn Ala
            245                 250                 255

Val Ser Val Lys Gly Ile Tyr Lys Gln Met Pro Gly Cys Phe Asn Phe
            260                 265                 270

Leu Arg Lys Lys Leu Phe Phe Lys Thr Ser
        275                 280
```

<210> SEQ ID NO 8
<211> LENGTH: 843
<212> TYPE: DNA
<213> ORGANISM: Artificial Sequence
<220> FEATURE:
<223> OTHER INFORMATION: truncated caspase 9

<400> SEQUENCE: 8

```
tttggggacg tggggggccct ggagtctctg cgaggaaatg ccgatctggc ttacatcctg      60
agcatggaac cctgcggcca ctgtctgatc attaacaatg tgaacttctg cagagaaagc     120
ggactgcgaa cacggactgg ctccaatatt gactgtgaga agctgcggag aaggttctct     180
agtctgcact tatggtcga agtgaaaggg gatctgaccg ccaagaaaat ggtgctggcc      240
ctgctggagc tggctcagca ggaccatgga gctctggatt gctgcgtggt cgtgatcctg     300
tcccacgggt gccaggcttc tcatctgcag ttccccggag cagtgtacgg aacagacggc     360
tgtcctgtca gcgtggagaa gatcgtcaac atcttcaacg gcacttcttg ccctagtctg     420
ggggaaaagc caaaactgtt ctttatccag gcctgtggcg gggaacagaa agatcacggc     480
ttcgaggtgg ccagcaccag ccctgaggac gaatcaccag ggagcaaccc tgaaccagat     540
gcaactccat tccaggaggg actgaggacc tttgaccagc tggatgctat ctcaagcctg     600
cccactccta gtgacatttt cgtgtcttac agtaccttcc aggctttgt ctcatggcgc      660
gatcccaagt cagggagctg gtacgtggag acactgacg acatctttga acagtggggcc    720
cattcagagg acctgcagag cctgctgctg cgagtggcaa acgctgtctc tgtgaagggc     780
atctacaaac agatgcccgg gtgcttcaat tttctgagaa agaaactgtt ctttaagact     840
tcc                                                                  843
```

<210> SEQ ID NO 9
<211> LENGTH: 394
<212> TYPE: PRT
<213> ORGANISM: Artificial Sequence
<220> FEATURE:
<223> OTHER INFORMATION: inducible proapoptotic polypeptide

<400> SEQUENCE: 9

```
Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Val Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
            85                  90                  95
```

Leu Val Phe Asp Val Glu Leu Leu Lys Leu Glu Gly Gly Gly Ser
            100                 105                 110

Gly Phe Gly Asp Val Gly Ala Leu Glu Ser Leu Arg Gly Asn Ala Asp
            115                 120                 125

Leu Ala Tyr Ile Leu Ser Met Glu Pro Cys Gly His Cys Leu Ile Ile
130                 135                 140

Asn Asn Val Asn Phe Cys Arg Glu Ser Gly Leu Arg Thr Arg Thr Gly
145                 150                 155                 160

Ser Asn Ile Asp Cys Glu Lys Leu Arg Arg Arg Phe Ser Ser Leu His
                165                 170                 175

Phe Met Val Glu Val Lys Gly Asp Leu Thr Ala Lys Lys Met Val Leu
            180                 185                 190

Ala Leu Leu Glu Leu Ala Gln Gln Asp His Gly Ala Leu Asp Cys Cys
        195                 200                 205

Val Val Val Ile Leu Ser His Gly Cys Gln Ala Ser His Leu Gln Phe
    210                 215                 220

Pro Gly Ala Val Tyr Gly Thr Asp Gly Cys Pro Val Ser Val Glu Lys
225                 230                 235                 240

Ile Val Asn Ile Phe Asn Gly Thr Ser Cys Pro Ser Leu Gly Gly Lys
                245                 250                 255

Pro Lys Leu Phe Phe Ile Gln Ala Cys Gly Gly Glu Gln Lys Asp His
            260                 265                 270

Gly Phe Glu Val Ala Ser Thr Ser Pro Glu Asp Glu Ser Pro Gly Ser
        275                 280                 285

Asn Pro Glu Pro Asp Ala Thr Pro Phe Gln Glu Gly Leu Arg Thr Phe
    290                 295                 300

Asp Gln Leu Asp Ala Ile Ser Ser Leu Pro Thr Pro Ser Asp Ile Phe
305                 310                 315                 320

Val Ser Tyr Ser Thr Phe Pro Gly Phe Val Ser Trp Arg Asp Pro Lys
                325                 330                 335

Ser Gly Ser Trp Tyr Val Glu Thr Leu Asp Asp Ile Phe Glu Gln Trp
            340                 345                 350

Ala His Ser Glu Asp Leu Gln Ser Leu Leu Leu Arg Val Ala Asn Ala
        355                 360                 365

Val Ser Val Lys Gly Ile Tyr Lys Gln Met Pro Gly Cys Phe Asn Phe
    370                 375                 380

Leu Arg Lys Lys Leu Phe Phe Lys Thr Ser
385                 390

<210> SEQ ID NO 10
<211> LENGTH: 1182
<212> TYPE: DNA
<213> ORGANISM: Artificial Sequence
<220> FEATURE:
<223> OTHER INFORMATION: nucleic acid encoding an inducible proapoptotic
      polypeptide

<400> SEQUENCE: 10
ggggtccagg tcgagactat ttcaccaggg gatgggcgaa catttccaaa aaggggccag     60
acttgcgtcg tgcattacac cgggatgctg gaggacggga agaaagtgga cagctccagg    120
gatcgcaaca agcccttcaa gttcatgctg ggaaagcagg aagtgatccg aggatgggag    180
gaaggcgtgg cacagatgtc agtcggccag cgggccaaac tgaccattag ccctgactac    240
gcttatggag caacaggcca cccagggatc attccccctc atgccaccct ggtcttcgat    300

```
gtggaactgc tgaagctgga gggaggagga ggatccggat ttggggacgt ggggggccctg      360 gagtctctgc gaggaaatgc cgatctggct tacatcctga gcatggaacc ctgcggccac      420
tgtctgatca ttaacaatgt gaacttctgc agagaaagcg gactgcgaac acggactggc      480
tccaatattg actgtgagaa gctgcggaga aggttctcta gtctgcactt tatggtcgaa      540
gtgaaagggg atctgaccgc caagaaaatg gtgctggccc tgctggagct ggctcagcag      600
gaccatggag ctctggattg ctgcgtggtc gtgatcctgt cccacgggtg ccaggcttct      660
catctgcagt tccccggagc agtgtacgga acagacggct gtcctgtcag cgtggagaag      720
atcgtcaaca tcttcaacgg cacttcttgc cctagtctgg ggggaaagcc aaaactgttc      780
tttatccagg cctgtggcgg ggaacagaaa gatcacggct cgaggtggc cagcaccagc       840 cctgaggacg aatcaccagg gagcaaccct gaaccagatg caactccatt ccaggaggga      900
ctgaggacct ttgaccagct ggatgctatc tcaagcctgc ccactcctag tgacattttc      960
gtgtcttaca gtaccttccc aggctttgtc tcatggcgcg atcccaagtc agggagctgg     1020
tacgtggaga cactggacga catctttgaa cagtgggccc attcagagga cctgcagagc     1080
ctgctgctgc gagtggcaaa cgctgtctct gtgaagggca tctacaaaca gatgcccggg     1140
tgcttcaatt ttctgagaaa gaaactgttc tttaagactt cc                         1182

<210> SEQ ID NO 11
<211> LENGTH: 18
<212> TYPE: PRT
<213> ORGANISM: Thosea asigna virus

<400> SEQUENCE: 11

Glu Gly Arg Gly Ser Leu Leu Thr Cys Gly Asp Val Glu Glu Asn Pro
1               5                   10                  15

Gly Pro

<210> SEQ ID NO 12
<211> LENGTH: 21
<212> TYPE: PRT
<213> ORGANISM: Artificial Sequence
<220> FEATURE:
<223> OTHER INFORMATION: GSG-T2A

<400> SEQUENCE: 12

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 13
<211> LENGTH: 20
<212> TYPE: PRT
<213> ORGANISM: Equine rhnitis A virus

<400> SEQUENCE: 13

Gln Cys Thr Asn Tyr Ala Leu Leu Lys Leu Ala Gly Asp Val Glu Ser
1               5                   10                  15

Asn Pro Gly Pro
            20

<210> SEQ ID NO 14
<211> LENGTH: 23
<212> TYPE: PRT
<213> ORGANISM: Artificial Sequence
<220> FEATURE:
```

```
<223> OTHER INFORMATION: GSG-E2A

<400> SEQUENCE: 14

Gly Ser Gly Gln Cys Thr Asn Tyr Ala Leu Leu Lys Leu Ala Gly Asp
1               5                   10                  15

Val Glu Ser Asn Pro Gly Pro
            20

<210> SEQ ID NO 15
<211> LENGTH: 22
<212> TYPE: PRT
<213> ORGANISM: Foot and mouth disease virus type O

<400> SEQUENCE: 15

Val Lys Gln Thr Leu Asn Phe Asp Leu Leu Lys Leu Ala Gly Asp Val
1               5                   10                  15

Glu Ser Asn Pro Gly Pro
            20

<210> SEQ ID NO 16
<211> LENGTH: 25
<212> TYPE: PRT
<213> ORGANISM: Artificial Sequence
<220> FEATURE:
<223> OTHER INFORMATION: GSG-F2A

<400> SEQUENCE: 16

Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25

<210> SEQ ID NO 17
<211> LENGTH: 19
<212> TYPE: PRT
<213> ORGANISM: Porcine teschovirus-1

<400> SEQUENCE: 17

Ala Thr Asn Phe Ser Leu Leu Lys Gln Ala Gly Asp Val Glu Glu Asn
1               5                   10                  15

Pro Gly Pro

<210> SEQ ID NO 18
<211> LENGTH: 22
<212> TYPE: PRT
<213> ORGANISM: Artificial Sequence
<220> FEATURE:
<223> OTHER INFORMATION: GSG-P2A

<400> SEQUENCE: 18

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 19
<211> LENGTH: 340
<212> TYPE: PRT
<213> ORGANISM: Artificial Sequence
<220> FEATURE:
<223> OTHER INFORMATION: Sleeping Beauty transposase

<400> SEQUENCE: 19
```

```
Met Gly Lys Ser Lys Glu Ile Ser Gln Asp Leu Arg Lys Lys Ile Val
1               5                   10                  15

Asp Leu His Lys Ser Gly Ser Ser Leu Gly Ala Ile Ser Lys Arg Leu
            20                  25                  30

Lys Val Pro Arg Ser Ser Val Gln Thr Ile Val Arg Lys Tyr Lys His
            35                  40                  45

His Gly Thr Thr Gln Pro Ser Tyr Arg Ser Gly Arg Arg Val Leu
        50                  55                  60

Ser Pro Arg Asp Glu Arg Thr Leu Val Arg Lys Val Gln Ile Asn Pro
65                  70                  75                  80

Arg Thr Thr Ala Lys Asp Leu Val Lys Met Leu Glu Glu Thr Gly Thr
                85                  90                  95

Lys Val Ser Ile Ser Thr Val Lys Arg Val Leu Tyr Arg His Asn Leu
                100                 105                 110

Lys Gly Arg Ser Ala Arg Lys Lys Pro Leu Leu Gln Asn Arg His Lys
                115                 120                 125

Lys Ala Arg Leu Arg Phe Ala Thr Ala His Gly Asp Lys Asp Arg Thr
            130                 135                 140

Phe Trp Arg Asn Val Leu Trp Ser Asp Glu Thr Lys Ile Glu Leu Phe
145                 150                 155                 160

Gly His Asn Asp His Arg Tyr Val Trp Arg Lys Lys Gly Glu Ala Cys
            165                 170                 175

Lys Pro Lys Asn Thr Ile Pro Thr Val Lys His Gly Gly Gly Ser Ile
            180                 185                 190

Met Leu Trp Gly Cys Phe Ala Ala Gly Gly Thr Gly Ala Leu His Lys
            195                 200                 205

Ile Asp Gly Ile Met Arg Lys Glu Asn Tyr Val Asp Ile Leu Lys Gln
210                 215                 220

His Leu Lys Thr Ser Val Arg Lys Leu Lys Leu Gly Arg Lys Trp Val
225                 230                 235                 240

Phe Gln Met Asp Asn Asp Pro Lys His Thr Ser Lys Val Val Ala Lys
            245                 250                 255

Trp Leu Lys Asp Asn Lys Val Lys Val Leu Glu Trp Pro Ser Gln Ser
            260                 265                 270

Pro Asp Leu Asn Pro Ile Glu Asn Leu Trp Ala Glu Leu Lys Lys Arg
            275                 280                 285

Val Arg Ala Arg Arg Pro Thr Asn Leu Thr Gln Leu His Gln Leu Cys
            290                 295                 300

Gln Glu Glu Trp Ala Lys Ile His Pro Thr Tyr Cys Gly Lys Leu Val
305                 310                 315                 320

Glu Gly Tyr Pro Lys Arg Leu Thr Gln Val Lys Gln Phe Lys Gly Asn
            325                 330                 335

Ala Thr Lys Tyr
            340

<210> SEQ ID NO 20
<211> LENGTH: 340
<212> TYPE: PRT
<213> ORGANISM: Artificial Sequence
<220> FEATURE:
<223> OTHER INFORMATION: hyperactive Sleeping Beauty transposase

<400> SEQUENCE: 20

Met Gly Lys Ser Lys Glu Ile Ser Gln Asp Leu Arg Lys Arg Ile Val
1               5                   10                  15
```

Asp Leu His Lys Ser Gly Ser Ser Leu Gly Ala Ile Ser Lys Arg Leu
            20                  25                  30

Ala Val Pro Arg Ser Ser Val Gln Thr Ile Val Arg Lys Tyr Lys His
        35                  40                  45

His Gly Thr Thr Gln Pro Ser Tyr Arg Ser Gly Arg Arg Val Leu
    50                  55                  60

Ser Pro Arg Asp Glu Arg Thr Leu Val Arg Lys Val Gln Ile Asn Pro
65                  70                  75                  80

Arg Thr Thr Ala Lys Asp Leu Val Lys Met Leu Glu Glu Thr Gly Thr
                85                  90                  95

Lys Val Ser Ile Ser Thr Val Lys Arg Val Leu Tyr Arg His Asn Leu
                100                 105                 110

Lys Gly His Ser Ala Arg Lys Lys Pro Leu Leu Gln Asn Arg His Lys
            115                 120                 125

Lys Ala Arg Leu Arg Phe Ala Thr Ala His Gly Asp Lys Asp Arg Thr
        130                 135                 140

Phe Trp Arg Asn Val Leu Trp Ser Asp Glu Thr Lys Ile Glu Leu Phe
145                 150                 155                 160

Gly His Asn Asp His Arg Tyr Val Trp Arg Lys Lys Gly Glu Ala Cys
                165                 170                 175

Lys Pro Lys Asn Thr Ile Pro Thr Val Lys His Gly Gly Gly Ser Ile
            180                 185                 190

Met Leu Trp Gly Cys Phe Ala Ala Gly Gly Thr Gly Ala Leu His Lys
        195                 200                 205

Ile Asp Gly Ile Met Asp Ala Val Gln Tyr Val Asp Ile Leu Lys Gln
    210                 215                 220

His Leu Lys Thr Ser Val Arg Lys Leu Lys Leu Gly Arg Lys Trp Val
225                 230                 235                 240

Phe Gln His Asp Asn Asp Pro Lys His Thr Ser Lys Val Val Ala Lys
                245                 250                 255

Trp Leu Lys Asp Asn Lys Val Lys Val Leu Glu Trp Pro Ser Gln Ser
            260                 265                 270

Pro Asp Leu Asn Pro Ile Glu Asn Leu Trp Ala Glu Leu Lys Lys Arg
        275                 280                 285

Val Arg Ala Arg Arg Pro Thr Asn Leu Thr Gln Leu His Gln Leu Cys
    290                 295                 300

Gln Glu Glu Trp Ala Lys Ile His Pro Asn Tyr Cys Gly Lys Leu Val
305                 310                 315                 320

Glu Gly Tyr Pro Lys Arg Leu Thr Gln Val Gln Phe Lys Gly Asn
                325                 330                 335

Ala Thr Lys Tyr
            340

<210> SEQ ID NO 21
<211> LENGTH: 5296
<212> TYPE: DNA
<213> ORGANISM: Artificial Sequence
<220> FEATURE:
<223> OTHER INFORMATION: Helraiser transposon

<400> SEQUENCE: 21
tcctatataa taaagagaaa acatgcaaat tgaccatccc tccgctacgc tcaagccacg      60
cccaccagcc aatcagaagt gactatgcaa attaacccaa caaagatggc agttaaattt     120
gcatacgcag gtgtcaagcg ccccaggagg caacggcggc cgcgggctcc caggaccttc     180

```
gctggccccg ggaggcgagg ccggccgcgc ctagccacac ccgcgggctc ccgggacctt    240
cgccagcaga gagcagagcg ggagagcggg cggagagcgg gaggtttgga ggacttggca    300
gagcaggagg ccgctggaca tagagcagag cgagagagag ggtggcttgg agggcgtggc    360
tccctctgtc accccagctt cctcatcaca gctgtggaaa ctgacagcag ggaggaggaa    420
gtcccacccc cacagaatca gccagaatca gccgttggtc agacagctct cagcggcctg    480
acagccagga ctctcattca cctgcatctc agaccgtgac agtagagagg tgggactatg    540
tctaaagaac aactgttgat acaacgtagc tctgcagccg aaagatgccg gcgttatcga    600
cagaaaatgt ctgcagagca acgtgcgtct gatcttgaaa gaaggcggcg cctgcaacag    660
aatgtatctg aagagcagct actggaaaaa cgtcgctctg aagccgaaaa acagcggcgt    720
catcgacaga aaatgtctaa agaccaacgt gcctttgaag ttgaaagaag gcggtggcga    780
cgacagaata tgtctagaga acagtcatca acaagtacta ccaataccgg taggaactgc    840
cttctcagca aaaatggagt acatgaggat gcaattctcg aacatagttg tggtggaatg    900
actgttcgat gtgaattttg cctatcacta aatttctctg atgaaaaacc atccgatggg    960
aaatttactc gatgttgtag caaagggaaa gtctgtccaa atgatataca ttttccagat   1020
tacccggcat atttaaaaag attaatgaca aacgaagatt ctgacagtaa aaatttcatg   1080 gaaatattc gttccataaa tagttctttt gcttttgctt ccatgggtgc aaatattgca   1140
tcgccatcag gatatgggcc atactgtttt agaatacacg gacaagttta tcaccgtact   1200
ggaactttac atccttcgga tggtgtttct cggaagtttg ctcaactcta tattttggat   1260
acagccgaag ctacaagtaa aagattagca atgccagaaa accagggctg ctcagaaaga   1320
ctcatgatca acatcaacaa cctcatgcat gaaataaatg aattaacaaa atcgtacaag   1380
atgctacatg aggtagaaaa ggaagcccaa tctgaagcag cagcaaaagg tattgctccc   1440
acagaagtaa caatggcgat taaatacgat cgtaacagtg acccaggtag atataattct   1500
ccccgtgtaa ccgaggttgc tgtcatattc agaaacgaag atggagaacc tccttttgaa   1560
agggacttgc tcattcattg taaaccagat cccaataatc caaatgccac taaaatgaaa   1620
caaatcagta tcctgttttcc tacattagat gcaatgacat atcctattct ttttccacat   1680
ggtgaaaaag gctggggaac agatattgca ttaagactca gagacaacag tgtaatcgac   1740
aataatacta gacaaaatgt aaggacacga gtcacacaaa tgcagtatta tggatttcat   1800
ctctctgtgc gggacacgtt caatcctatt ttaaatgcag gaaaattaac tcaacagttt   1860
attgtggatt catattcaaa aatggaggcc aatcggataa atttcatcaa agcaaaccaa   1920
tctaagttga gagttgaaaa atatagtggt ttgatggatt atctcaaatc tagatctgaa   1980
aatgacaatg tgccgattgg taaaatgata atacttccat catcttttga gggtagtccc   2040
agaaatatgc agcagcgata tcaggatgct atggcaattg taacgaagta tggcaagccc   2100
gatttattca taaccatgac atgcaacccc aaatgggcag atattacaaa caatttacaa   2160
cgctggcaaa aagttgaaaa cagacctgac ttggtagcca gagttttaa tattaagctg   2220 aatgctcttt taaatgatat atgtaaattc catttatttg gcaaagtaat agctaaaatt   2280
catgtcattg aatttcagaa acgcggactg cctcacgctc atatattatt gatattagat   2340
agtgagtcca aattacgttc agaagatgac attgaccgta tagttaaggc agaaattcca   2400
gatgaagacc agtgtcctcg acttttttcaa attgtaaaat caaatatggt acatggacca   2460
tgtggaatac aaaatccaaa tagtccatgt atggaaaatg gaaaatgttc aaagggatat   2520
ccaaaagaat ttcaaaatgc gaccattgga atatttgatg gatatcccaa atacaaacga   2580
```

```
agatctggta gcaccatgtc tattggaaat aaagttgtcg ataacacttg gattgtccct    2640
tataacccgt atttgtgcct taaatataac tgtcatataa atgttgaagt ctgtgcatca    2700
attaaaagtg tcaaatattt atttaaatac atctataaag ggcacgattg tgcaaatatt    2760
caaatttctg aaaaaaatat tatcaatcat gacgaagtac aggacttcat tgactccagg    2820
tatgtgagcg ctcctgaggc tgtttggaga cttttttgcaa tgcgaatgca tgaccaatct    2880
catgcaatca caagattagc tattcatttg ccaaatgatc agaatttgta ttttcatacc    2940
gatgattttg ctgaagtttt agatagggct aaaaggcata actcgacttt gatggcttgg    3000
ttcttattga atagagaaga ttctgatgca cgtaattatt attattggga gattccacag    3060
cattatgtgt ttaataattc tttgtggaca aaacgccgaa agggtgggaa taaagtatta    3120
ggtagactgt tcactgtgag ctttagagaa ccagaacgat attaccttag acttttgctt    3180
ctgcatgtaa aaggtgcgat aagttttgag gatctgcgaa ctgtaggagg tgtaacttat    3240
gatacatttc atgaagctgc taaacaccga ggattattac ttgatgacac tatctggaaa    3300
gatacgattg acgatgcaat catccttaat atgcccaaac aactacggca acttttttgca    3360 tatatatgtg tgtttggatg tccttctgct gcagacaaat tatgggatga aataaatct    3420 cattttattg aagatttctg ttggaaatta caccgaagag aaggtgcctg tgtgaactgt    3480
gaaatgcatg cccttaacga aattcaggag gtattcacat tgcatggaat gaaatgttca    3540
catttcaaac ttccggacta tccttttatta atgaatgcaa atacatgtga tcaattgtac    3600
gagcaacaac aggcagaggt tttgataaat tctctgaatg atgaacagtt ggcagccttt    3660
cagactataa cttcagccat cgaagatcaa actgtacacc ccaaatgctt tttcttggat    3720
ggtccaggtg gtagtggaaa aacatatctg tataaagttt taacacatta tattagaggt    3780
cgtggtggta ctgttttacc cacagcatct acaggaattg ctgcaaattt acttcttggt    3840
ggaagaacct ttcattccca atataaatta ccaattccat taaatgaaac ttcaattttct    3900 agactcgata taaagagtga agttgctaaa accattaaaa aggcccaact tctcattatt    3960
gatgaatgca ccatggcatc cagtcatgct ataaacgcca tagatagatt actaagagaa    4020
attatgaatt tgaatgttgc atttggtggg aaagttctcc ttctcggagg ggattttcga    4080
caatgtctca gtattgtacc acatgctatg cgatcggcca tagtacaaac gagtttaaag    4140
tactgtaatg tttggggatg tttcagaaag ttgtctctta aaacaaatat gagatcagag    4200
gattctgctt atagtgaatg gttagtaaaa cttggagatg gcaaacttga tagcagtttt    4260
catttaggaa tggatattat tgaaatcccc catgaaatga tttgtaacgg atctattatt    4320
gaagctacct ttggaaatag tatatctata gataatatta aaaatatatc taaacgtgca    4380
attctttgtc caaaaaatga gcatgttcaa aaattaaatg aagaattttt ggatatactt    4440
gatggagatt ttcacacata tttgagtgat gattccattg attcaacaga tgatgctgaa    4500
aaggaaaatt ttcccatcga atttcttaat agtattactc cttcgggaat gccgtgtcat    4560
aaattaaaat tgaaagtggg tgcaatcatc atgctattga gaaatcttaa tagtaaatgg    4620
ggtctttgta atggtactag atttattatc aaaagattac gacctaacat tatcgaagct    4680
gaagtattaa caggatctgc agagggagag gttgttctga ttccaagaat tgatttgtcc    4740
ccatctgaca ctggcctccc atttaaatta attcgaagac agttttcccgt gatgccagca    4800 tttgcgatga ctattaataa atcacaagga caaactctag acagagtagg aatattccta    4860
cctgaacccg ttttcgcaca tggtcagtta tatgttgctt tctctcgagt tcgaagagca    4920
```

```
tgtgacgtta aagttaaagt tgtaaatact tcatcacaag ggaaattagt caagcactct    4980
gaaagtgttt ttactcttaa tgtggtatac agggagatat tagaataagt ttaatcactt    5040
tatcagtcat tgtttgcatc aatgttgttt ttatatcatg tttttgttgt ttttatatca    5100
tgtctttgtt gttgttatat catgttgtta ttgtttattt attaataaat ttatgtatta    5160
ttttcatata cattttactc atttcctttc atctctcaca cttctattat agagaaaggg    5220
caaatagcaa tattaaaata tttcctctaa ttaattccct ttcaatgtgc acgaatttcg    5280
tgcaccgggc cactag                                                    5296
```

<210> SEQ ID NO 22
<211> LENGTH: 1496
<212> TYPE: PRT
<213> ORGANISM: Artificial Sequence
<220> FEATURE:
<223> OTHER INFORMATION: Helitron transposase

<400> SEQUENCE: 22

```
Met Ser Lys Glu Gln Leu Leu Ile Gln Arg Ser Ala Ala Glu Arg
1               5                  10                  15

Cys Arg Arg Tyr Arg Gln Lys Met Ser Ala Glu Gln Arg Ala Ser Asp
            20                  25                  30

Leu Glu Arg Arg Arg Leu Gln Gln Asn Val Ser Glu Glu Gln Leu
        35                  40                  45

Leu Glu Lys Arg Arg Ser Glu Ala Lys Gln Arg Arg His Arg Gln
    50                  55                  60

Lys Met Ser Lys Asp Gln Arg Ala Phe Glu Val Glu Arg Arg Trp
65                  70                  75                  80

Arg Arg Gln Asn Met Ser Arg Glu Gln Ser Ser Thr Ser Thr Thr Asn
                85                  90                  95

Thr Gly Arg Asn Cys Leu Leu Ser Lys Asn Gly Val His Glu Asp Ala
            100                 105                 110

Ile Leu Glu His Ser Cys Gly Gly Met Thr Val Arg Cys Glu Phe Cys
        115                 120                 125

Leu Ser Leu Asn Phe Ser Asp Glu Lys Pro Ser Asp Gly Lys Phe Thr
    130                 135                 140

Arg Cys Cys Ser Lys Gly Lys Val Cys Pro Asn Asp Ile His Phe Pro
145                 150                 155                 160

Asp Tyr Pro Ala Tyr Leu Lys Arg Leu Met Thr Asn Glu Asp Ser Asp
                165                 170                 175

Ser Lys Asn Phe Met Glu Asn Ile Arg Ser Ile Asn Ser Ser Phe Ala
            180                 185                 190

Phe Ala Ser Met Gly Ala Asn Ile Ala Ser Pro Ser Gly Tyr Gly Pro
        195                 200                 205

Tyr Cys Phe Arg Ile His Gly Gln Val Tyr His Arg Thr Gly Thr Leu
    210                 215                 220

His Pro Ser Asp Gly Val Ser Arg Lys Phe Ala Gln Leu Tyr Ile Leu
225                 230                 235                 240

Asp Thr Ala Glu Ala Thr Ser Lys Arg Leu Ala Met Pro Glu Asn Gln
                245                 250                 255

Gly Cys Ser Glu Arg Leu Met Ile Ile Asn Ile Asn Leu Met His Glu
            260                 265                 270

Ile Asn Glu Leu Thr Lys Ser Tyr Lys Met Leu His Glu Val Glu Lys
        275                 280                 285

Glu Ala Gln Ser Glu Ala Ala Ala Lys Gly Ile Ala Pro Thr Glu Val
```

-continued

```
            290                 295                 300
Thr Met Ala Ile Lys Tyr Asp Arg Asn Ser Asp Pro Gly Arg Tyr Asn
305                 310                 315                 320
Ser Pro Arg Val Thr Glu Val Ala Val Ile Phe Arg Asn Glu Asp Gly
                    325                 330                 335
Glu Pro Pro Phe Glu Arg Asp Leu Leu Ile His Cys Lys Pro Asp Pro
                340                 345                 350
Asn Asn Pro Asn Ala Thr Lys Met Lys Gln Ile Ser Ile Leu Phe Pro
            355                 360                 365
Thr Leu Asp Ala Met Thr Tyr Pro Ile Leu Phe Pro His Gly Glu Lys
370                 375                 380
Gly Trp Gly Thr Asp Ile Ala Leu Arg Leu Arg Asp Asn Ser Val Ile
385                 390                 395                 400
Asp Asn Asn Thr Arg Gln Asn Val Arg Thr Arg Val Thr Gln Met Gln
                405                 410                 415
Tyr Tyr Gly Phe His Leu Ser Val Arg Asp Thr Phe Asn Pro Ile Leu
            420                 425                 430
Asn Ala Gly Lys Leu Thr Gln Gln Phe Ile Val Asp Ser Tyr Ser Lys
            435                 440                 445
Met Glu Ala Asn Arg Ile Asn Phe Ile Lys Ala Asn Gln Ser Lys Leu
450                 455                 460
Arg Val Glu Lys Tyr Ser Gly Leu Met Asp Tyr Leu Lys Ser Arg Ser
465                 470                 475                 480
Glu Asn Asp Asn Val Pro Ile Gly Lys Met Ile Ile Leu Pro Ser Ser
                485                 490                 495
Phe Glu Gly Ser Pro Arg Asn Met Gln Gln Arg Tyr Gln Asp Ala Met
                500                 505                 510
Ala Ile Val Thr Lys Tyr Gly Lys Pro Asp Leu Phe Ile Thr Met Thr
            515                 520                 525
Cys Asn Pro Lys Trp Ala Asp Ile Thr Asn Asn Leu Gln Arg Trp Gln
530                 535                 540
Lys Val Glu Asn Arg Pro Asp Leu Val Ala Arg Val Phe Asn Ile Lys
545                 550                 555                 560
Leu Asn Ala Leu Leu Asn Asp Ile Cys Lys Phe His Leu Phe Gly Lys
                565                 570                 575
Val Ile Ala Lys Ile His Val Ile Glu Phe Gln Lys Arg Gly Leu Pro
            580                 585                 590
His Ala His Ile Leu Leu Ile Leu Asp Ser Glu Ser Lys Leu Arg Ser
            595                 600                 605
Glu Asp Asp Ile Asp Arg Ile Val Lys Ala Glu Ile Pro Asp Glu Asp
610                 615                 620
Gln Cys Pro Arg Leu Phe Gln Ile Val Lys Ser Asn Met Val His Gly
625                 630                 635                 640
Pro Cys Gly Ile Gln Asn Pro Asn Ser Pro Cys Met Glu Asn Gly Lys
                645                 650                 655
Cys Ser Lys Gly Tyr Pro Lys Glu Phe Gln Asn Ala Thr Ile Gly Asn
                660                 665                 670
Ile Asp Gly Tyr Pro Lys Tyr Lys Arg Arg Ser Gly Ser Thr Met Ser
            675                 680                 685
Ile Gly Asn Lys Val Val Asp Asn Thr Trp Ile Val Pro Tyr Asn Pro
            690                 695                 700
Tyr Leu Cys Leu Lys Tyr Asn Cys His Ile Asn Val Glu Val Cys Ala
705                 710                 715                 720
```

```
Ser Ile Lys Ser Val Lys Tyr Leu Phe Lys Tyr Ile Tyr Lys Gly His
            725                 730                 735

Asp Cys Ala Asn Ile Gln Ile Ser Glu Lys Asn Ile Ile Asn His Asp
            740                 745                 750

Glu Val Gln Asp Phe Ile Asp Ser Arg Tyr Val Ser Ala Pro Glu Ala
        755                 760                 765

Val Trp Arg Leu Phe Ala Met Arg Met His Asp Gln Ser His Ala Ile
770                 775                 780

Thr Arg Leu Ala Ile His Leu Pro Asn Asp Gln Asn Leu Tyr Phe His
785                 790                 795                 800

Thr Asp Asp Phe Ala Glu Val Leu Asp Arg Ala Lys Arg His Asn Ser
            805                 810                 815

Thr Leu Met Ala Trp Phe Leu Leu Asn Arg Glu Asp Ser Asp Ala Arg
            820                 825                 830

Asn Tyr Tyr Tyr Trp Glu Ile Pro Gln His Tyr Val Phe Asn Asn Ser
            835                 840                 845

Leu Trp Thr Lys Arg Arg Lys Gly Gly Asn Lys Val Leu Gly Arg Leu
    850                 855                 860

Phe Thr Val Ser Phe Arg Glu Pro Glu Arg Tyr Tyr Leu Arg Leu Leu
865                 870                 875                 880

Leu Leu His Val Lys Gly Ala Ile Ser Phe Glu Asp Leu Arg Thr Val
                885                 890                 895

Gly Gly Val Thr Tyr Asp Thr Phe His Glu Ala Ala Lys His Arg Gly
                900                 905                 910

Leu Leu Leu Asp Asp Thr Ile Trp Lys Asp Thr Ile Asp Asp Ala Ile
            915                 920                 925

Ile Leu Asn Met Pro Lys Gln Leu Arg Gln Leu Phe Ala Tyr Ile Cys
    930                 935                 940

Val Phe Gly Cys Pro Ser Ala Ala Asp Lys Leu Trp Asp Glu Asn Lys
945                 950                 955                 960

Ser His Phe Ile Glu Asp Phe Cys Trp Lys Leu His Arg Arg Glu Gly
                965                 970                 975

Ala Cys Val Asn Cys Glu Met His Ala Leu Asn Glu Ile Gln Glu Val
                980                 985                 990

Phe Thr Leu His Gly Met Lys Cys  Ser His Phe Lys Leu Pro Asp Tyr
            995                 1000                1005

Pro Leu Leu Met Asn Ala Asn  Thr Cys Asp Gln Leu  Tyr Glu Gln
    1010                1015                1020

Gln Gln  Ala Glu Val Leu Ile  Asn Ser Leu Asn Asp  Glu Gln Leu
    1025                1030                1035

Ala Ala  Phe Gln Thr Ile Thr  Ser Ala Ile Glu Asp  Gln Thr Val
    1040                1045                1050

His Pro  Lys Cys Phe Phe Leu  Asp Gly Pro Gly Gly  Ser Gly Lys
    1055                1060                1065

Thr Tyr  Leu Tyr Lys Val Leu  Thr His Tyr Ile Arg  Gly Arg Gly
    1070                1075                1080

Gly Thr  Val Leu Pro Thr Ala  Ser Thr Gly Ile Ala  Ala Asn Leu
    1085                1090                1095

Leu Leu  Gly Gly Arg Thr Phe  His Ser Gln Tyr Lys  Leu Pro Ile
    1100                1105                1110

Pro Leu  Asn Glu Thr Ser Ile  Ser Arg Leu Asp Ile  Lys Ser Glu
    1115                1120                1125
```

```
Val Ala Lys Thr Ile Lys Lys Ala Gln Leu Leu Ile Ile Asp Glu
    1130            1135                1140

Cys Thr Met Ala Ser Ser His Ala Ile Asn Ala Ile Asp Arg Leu
    1145            1150                1155

Leu Arg Glu Ile Met Asn Leu Asn Val Ala Phe Gly Gly Lys Val
    1160            1165                1170

Leu Leu Leu Gly Gly Asp Phe Arg Gln Cys Leu Ser Ile Val Pro
    1175            1180                1185

His Ala Met Arg Ser Ala Ile Val Gln Thr Ser Leu Lys Tyr Cys
    1190            1195                1200

Asn Val Trp Gly Cys Phe Arg Lys Leu Ser Leu Lys Thr Asn Met
    1205            1210                1215

Arg Ser Glu Asp Ser Ala Tyr Ser Glu Trp Leu Val Lys Leu Gly
    1220            1225                1230

Asp Gly Lys Leu Asp Ser Ser Phe His Leu Gly Met Asp Ile Ile
    1235            1240                1245

Glu Ile Pro His Glu Met Ile Cys Asn Gly Ser Ile Ile Glu Ala
    1250            1255                1260

Thr Phe Gly Asn Ser Ile Ser Ile Asp Asn Ile Lys Asn Ile Ser
    1265            1270                1275

Lys Arg Ala Ile Leu Cys Pro Lys Asn Glu His Val Gln Lys Leu
    1280            1285                1290

Asn Glu Glu Ile Leu Asp Ile Leu Asp Gly Asp Phe His Thr Tyr
    1295            1300                1305

Leu Ser Asp Asp Ser Ile Asp Ser Thr Asp Asp Ala Glu Lys Glu
    1310            1315                1320

Asn Phe Pro Ile Glu Phe Leu Asn Ser Ile Thr Pro Ser Gly Met
    1325            1330                1335

Pro Cys His Lys Leu Lys Leu Lys Val Gly Ala Ile Ile Met Leu
    1340            1345                1350

Leu Arg Asn Leu Asn Ser Lys Trp Gly Leu Cys Asn Gly Thr Arg
    1355            1360                1365

Phe Ile Ile Lys Arg Leu Arg Pro Asn Ile Ile Glu Ala Glu Val
    1370            1375                1380

Leu Thr Gly Ser Ala Glu Gly Glu Val Val Leu Ile Pro Arg Ile
    1385            1390                1395

Asp Leu Ser Pro Ser Asp Thr Gly Leu Pro Phe Lys Leu Ile Arg
    1400            1405                1410

Arg Gln Phe Pro Val Met Pro Ala Phe Ala Met Thr Ile Asn Lys
    1415            1420                1425

Ser Gln Gly Gln Thr Leu Asp Arg Val Gly Ile Phe Leu Pro Glu
    1430            1435                1440

Pro Val Phe Ala His Gly Gln Leu Tyr Val Ala Phe Ser Arg Val
    1445            1450                1455

Arg Arg Ala Cys Asp Val Lys Val Lys Val Asn Thr Ser Ser
    1460            1465                1470

Gln Gly Lys Leu Val Lys His Ser Glu Ser Val Phe Thr Leu Asn
    1475            1480                1485

Val Val Tyr Arg Glu Ile Leu Glu
    1490            1495
```

<210> SEQ ID NO 23
<211> LENGTH: 30
<212> TYPE: DNA

<213> ORGANISM: Artificial Sequence
<220> FEATURE:
<223> OTHER INFORMATION: helraiser transposon palindromic sequence

<400> SEQUENCE: 23
gtgcacgaat tcgtgcacc gggccactag                                              30

<210> SEQ ID NO 24
<211> LENGTH: 649
<212> TYPE: PRT
<213> ORGANISM: Oryzias latipes

<400> SEQUENCE: 24

```
Met Glu Glu Val Cys Asp Ser Ser Ala Ala Ser Ser Thr Val Gln
1               5                   10                  15

Asn Gln Pro Gln Asp Gln Glu His Pro Trp Pro Tyr Leu Arg Glu Phe
            20                  25                  30

Phe Ser Leu Ser Gly Val Asn Lys Asp Ser Phe Lys Met Lys Cys Val
        35                  40                  45

Leu Cys Leu Pro Leu Asn Lys Glu Ile Ser Ala Phe Lys Ser Ser Pro
    50                  55                  60

Ser Asn Leu Arg Lys His Ile Glu Arg Met His Pro Asn Tyr Leu Lys
65                  70                  75                  80

Asn Tyr Ser Lys Leu Thr Ala Gln Lys Arg Lys Ile Gly Thr Ser Thr
                85                  90                  95

His Ala Ser Ser Lys Gln Leu Lys Val Asp Ser Val Phe Pro Val
            100                 105                 110

Lys His Val Ser Pro Val Thr Val Asn Lys Ala Ile Leu Arg Tyr Ile
        115                 120                 125

Ile Gln Gly Leu His Pro Phe Ser Thr Val Asp Leu Pro Ser Phe Lys
    130                 135                 140

Glu Leu Ile Ser Thr Leu Gln Pro Gly Ile Ser Val Ile Thr Arg Pro
145                 150                 155                 160

Thr Leu Arg Ser Lys Ile Ala Glu Ala Ala Leu Ile Met Lys Gln Lys
                165                 170                 175

Val Thr Ala Ala Met Ser Glu Val Glu Trp Ile Ala Thr Thr Thr Asp
            180                 185                 190

Cys Trp Thr Ala Arg Arg Lys Ser Phe Ile Gly Val Thr Ala His Trp
        195                 200                 205

Ile Asn Pro Gly Ser Leu Glu Arg His Ser Ala Ala Leu Ala Cys Lys
    210                 215                 220

Arg Leu Met Gly Ser His Thr Phe Glu Val Leu Ala Ser Ala Met Asn
225                 230                 235                 240

Asp Ile His Ser Glu Tyr Glu Ile Arg Asp Lys Val Val Cys Thr Thr
                245                 250                 255

Thr Asp Ser Gly Ser Asn Phe Met Lys Ala Phe Arg Val Phe Gly Val
            260                 265                 270

Glu Asn Asn Asp Ile Glu Thr Glu Ala Arg Arg Cys Glu Ser Asp Asp
        275                 280                 285

Thr Asp Ser Glu Gly Cys Gly Glu Gly Ser Asp Gly Val Glu Phe Gln
    290                 295                 300

Asp Ala Ser Arg Val Leu Asp Gln Asp Asp Gly Phe Glu Phe Gln Leu
305                 310                 315                 320

Pro Lys His Gln Lys Cys Ala Cys His Leu Leu Asn Leu Val Ser Ser
                325                 330                 335
```

Val Asp Ala Gln Lys Ala Leu Ser Asn Glu His Tyr Lys Lys Leu Tyr
            340                 345                 350

Arg Ser Val Phe Gly Lys Cys Gln Ala Leu Trp Asn Lys Ser Ser Arg
        355                 360                 365

Ser Ala Leu Ala Ala Glu Ala Val Glu Ser Glu Ser Arg Leu Gln Leu
    370                 375                 380

Leu Arg Pro Asn Gln Thr Arg Trp Asn Ser Thr Phe Met Ala Val Asp
385                 390                 395                 400

Arg Ile Leu Gln Ile Cys Lys Glu Ala Gly Glu Gly Ala Leu Arg Asn
                405                 410                 415

Ile Cys Thr Ser Leu Glu Val Pro Met Phe Asn Pro Ala Glu Met Leu
            420                 425                 430

Phe Leu Thr Glu Trp Ala Asn Thr Met Arg Pro Val Ala Lys Val Leu
        435                 440                 445

Asp Ile Leu Gln Ala Glu Thr Asn Thr Gln Leu Gly Trp Leu Leu Pro
    450                 455                 460

Ser Val His Gln Leu Ser Leu Lys Leu Gln Arg Leu His Ser Leu
465                 470                 475                 480

Arg Tyr Cys Asp Pro Leu Val Asp Ala Leu Gln Gln Gly Ile Gln Thr
                485                 490                 495

Arg Phe Lys His Met Phe Glu Asp Pro Glu Ile Ile Ala Ala Ile
            500                 505                 510

Leu Leu Pro Lys Phe Arg Thr Ser Trp Thr Asn Asp Glu Thr Ile Ile
        515                 520                 525

Lys Arg Gly Met Asp Tyr Ile Arg Val His Leu Glu Pro Leu Asp His
    530                 535                 540

Lys Lys Glu Leu Ala Asn Ser Ser Ser Asp Asp Glu Asp Phe Phe Ala
545                 550                 555                 560

Ser Leu Lys Pro Thr Thr His Glu Ala Ser Lys Glu Leu Asp Gly Tyr
                565                 570                 575

Leu Ala Cys Val Ser Asp Thr Arg Glu Ser Leu Leu Thr Phe Pro Ala
            580                 585                 590

Ile Cys Ser Leu Ser Ile Lys Thr Asn Thr Pro Leu Pro Ala Ser Ala
        595                 600                 605

Ala Cys Glu Arg Leu Phe Ser Thr Ala Gly Leu Leu Phe Ser Pro Lys
    610                 615                 620

Arg Ala Arg Leu Asp Thr Asn Asn Phe Glu Asn Gln Leu Leu Leu Lys
625                 630                 635                 640

Leu Asn Leu Arg Phe Tyr Asn Phe Glu
                645

<210> SEQ ID NO 25
<211> LENGTH: 4682
<212> TYPE: DNA
<213> ORGANISM: Oryzias latipes

<400> SEQUENCE: 25
cagaggtgta aagtacttga gtaattttac ttgattactg tacttaagta ttattttttgg      60 ggatttttac tttacttgag tacaattaaa aatcaatact tttacttta cttaattaca     120 ttttttttaga aaaaaagta cttttttactc cttacaattt tatttacagt caaaaagtac    180 ttatttttttg gagatcactt cattctattt tcccttgcta ttaccaaacc aattgaattg    240
cgctgatgcc cagtttaatt taatgtttat ttattctgcc tatgaaaatc gttttcacat     300
tatatgaaat tggtcagaca tgttcattgg tcctttggaa gtgacgtcat gtcacatcta    360

```
ttaccacaat gcacagcacc ttgacctgga aattagggaa attataacag tcaatcagtg       420
gaagaaaatg gaggaagtat gtgattcatc agcagctgcg agcagcacag tccaaaatca       480
gccacaggat caagagcacc cgtggccgta tcttcgcgaa ttcttttctt taagtggtgt       540
aaataaagat tcattcaaga tgaaatgtgt cctctgtctc ccgcttaata aagaaatatc       600
ggccttcaaa agttcgccat caaacctaag gaagcatatt gaggtaagta cattaagtat       660
tttgttttac tgatagtttt ttttttttt tttttttt ttttgggtg tgcatgtttt          720 gacgttgatg gcgcgccttt tatatgtgta gtaggcctat tttcactaat gcatgcgatt       780
gacaatataa ggctcacgta ataaaatgct aaaatgcatt tgtaattggt aacgttaggt       840
ccacgggaaa tttggcgcct attgcagctt tgaataatca ttatcattcc gtgctctcat       900
tgtgtttgaa ttcatgcaaa acacaagaaa accaagcgag aaattttttt ccaaacatgt       960
tgtattgtca aaacggtaac actttacaat gaggttgatt agttcatgta ttaactaaca      1020
ttaaataacc atgagcaata catttgttac tgtatctgtt aatctttgtt aacgttagtt      1080
aatagaaata cagatgttca ttgtttgttc atgttagttc acagtgcatt aactaatgtt      1140
aacaagatat aaagtattag taaatgttga aattaacatg tatacgtgca gttcattatt      1200
agttcatgtt aactaatgta gttaactaac gaaccttatt gtaaagtgt taccatcaaa       1260 actaatgtaa tgaaatcaat tcaccctgtc atgtcagcct tacagtcctg tgttttgtc       1320 aatataatca gaaataaaat taatgtttga ttgtcactaa atgctactgt atttctaaaa      1380
tcaacaagta tttaacatta taagtgtgc aattggctgc aaatgtcagt tttattaaag       1440
ggttagttca cccaaaaatg aaaataatgt cattaatgac tcgccctcat gtcgttccaa      1500
gcccgtaaga cctccgttca tcttcagaac acagtttaag atattttaga tttagtccga      1560
gagctttctg tgcctccatt gagaatgtat gtacggtata ctgtccatgt ccagaaaggt      1620
aataaaaaca tcaaagtagt ccatgtgaca tcagtgggtt agttagaatt ttttgaagca      1680
tcgaatacat tttggtccaa aaataacaaa acctacgact ttattcggca ttgtattctc      1740
ttccgggtct gttgtcaatc cgcgttcacg acttcgcagt gacgctacaa tgctgaataa      1800
agtcgtaggt tttgttattt ttggaccaaa atgtattttc gatgcttcaa ataattctac      1860
ctaacccact gatgtcacat ggactacttt gatgttttta ttaccttct ggacatggac       1920 agtataccgt acatacattt tcagtggagg gacagaaagc tctcggacta aatctaaaat      1980
atcttaaact gtgttccgaa gatgaacgga ggtgttacgg gcttggaacg acatgagggt      2040
gagtcattaa tgacatcttt tcattttgg gtgaactaac cctttaatgc tgtaatcaga       2100
gagtgtatgt gtaattgtta catttattgc atacaatata aatatttatt gttgttttt      2160 acagagaatg cacccaaatt acctcaaaaa ctactctaaa ttgacagcac agaagagaaa      2220
gatcgggacc tccacccatg cttccagcag taagcaactg aaagttgact cagttttccc      2280
agtcaaacat gtgtctccag tcactgtgaa caaagctata ttaaggtaca tcattcaagg      2340
acttcatcct ttcagcactg ttgatctgcc atcatttaaa gagctgatta gtacactgca      2400
gcctggcatt tctgtcatta caaggcctac tttacgctcc aagatagctg aagctgctct      2460
gatcatgaaa cagaaagtga ctgctgccat gagtgaagtt gaatgaattg caaccacaac      2520
ggattgttgg actgcacgta gaaagtcatt cattggtgta actgctcact ggatcaaccc      2580
tggaagtctt gaaagacatt ccgctgcact tgcctgcaaa agattaatgg gctctcatac      2640
ttttgaggta ctggccagtg ccatgaatga tatccactca gagtatgaaa tacgtgacaa      2700
```

-continued

```
ggttgtttgc acaaccacag acagtggttc caactttatg aaggctttca gagttttttgg    2760 tgtggaaaac aatgatatcg agactgaggc aagaaggtgt gaaagtgatg acactgattc    2820
tgaaggctgt ggtgagggaa gtgatggtgt ggaattccaa gatgcctcac gagtcctgga    2880
ccaagacgat ggcttcgaat tccagctacc aaaacatcaa aagtgtgcct gtcacttact    2940
taacctagtc tcaagcgttg atgcccaaaa agctctctca aatgaacact acaagaaact    3000
ctacagatct gtctttggca aatgccaagc tttatggaat aaaagcagcc gatcggctct    3060
agcagctgaa gctgttgaat cagaaagccg gcttcagctt taaggccaa accaaacgcg     3120 gtggaattca acttttatgg ctgttgacag aattcttcaa atttgcaaag aagcaggaga    3180
aggcgcactt cggaatatat gcacctctct tgaggttcca atgtaagtgt ttttcccctc    3240
tatcgatgta aacaaatgtg ggttgttttt gtttaatact ctttgattat gctgatttct    3300
cctgtaggtt taatccagca gaaatgctgt tcttgacaga gtgggccaac acaatgcgtc    3360
cagttgcaaa agtactcgac atcttgcaag cggaaacgaa tacacagctg ggtggctgc     3420 tgcctagtgt ccatcagtta agcttgaaac ttcagcgact ccaccattct ctcaggtact    3480
gtgacccact tgtggatgcc ctacaacaag gaatccaaac acgattcaag catatgtttg    3540
aagatcctga gatcatagca gctgccatcc ttctccctaa atttcggacc tcttggacaa    3600
atgatgaaac catcataaaa cgaggtaaat gaatgcaagc aacatacact tgacgaattc    3660
taatctgggc aacctttgag ccataccaaa attattcttt tatttattta tttttgcact    3720
ttttaggaat gttatatccc atctttggct gtgatctcaa tatgaatatt gatgtaaagt    3780
attcttgcag caggttgtag ttatccctca gtgtttcttg aaaccaaact catatgtatc    3840
atatgtggtt tggaaatgca gttagatttt atgctaaaat aagggatttg catgattta     3900 gatgtagatg actgcacgta aatgtagtta atgacaaaat ccataaaatt tgttcccagt    3960
cagaagcccc tcaaccaaac ttttctttgt gtctgctcac tgtgcttgta ggcatggact    4020
acatcagagt gcatctggag cctttggacc acaagaagga attggccaac agttcatctg    4080
atgatgaaga ttttttcgct tcttttgaaac cgacaacaca tgaagccagc aaagagttgg   4140
atggatatct ggcctgtgtt tcagacacca gggagtctct gctcacgttt cctgctattt    4200
gcagcctctc tatcaagact aatacacctc ttcccgcatc ggctgcctgt gagaggcttt    4260
tcagcactgc aggattgctt ttcagcccca aaagagctag gcttgacact aacaattttg    4320
agaatcagct tctactgaag ttaaatctga ggttttacaa ctttgagtag cgtgtactgg    4380
cattagattg tctgtcttat agtttgataa ttaaatacaa acagttctaa agcaggataa    4440
aaccttgtat gcatttcatt taatgttttt tgagattaaa agcttaaaca agaatctcta    4500
gttttctttc ttgcttttac ttttacttcc ttaatactca agtacaattt taatggagta    4560
cttttttact tttactcaag taagattcta gccagatact tttactttta attgagtaaa    4620
atttttccta agtacttgta ctttcacttg agtaaaattt ttgagtactt tttacacctc    4680
tg                                                                   4682
```